(12) United States Patent
Hilgers et al.

(10) Patent No.: US 8,637,659 B2
(45) Date of Patent: *Jan. 28, 2014

(54) MONO-AND DISACCHARIDE DERIVATIVES

(75) Inventors: Lucas Alfonsus T. Hilgers, Utrecht (NL); Anneke Georgine Blom, Lelystad (NL)

(73) Assignee: Protherics Medicines Development Limited, Cheshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/482,110

(22) Filed: May 29, 2012

(65) Prior Publication Data

US 2012/0288528 A1 Nov. 15, 2012

Related U.S. Application Data

(63) Continuation of application No. 13/162,335, filed on Jun. 16, 2011, now abandoned, which is a continuation of application No. 12/386,577, filed on Apr. 20, 2009, now Pat. No. 8,052,981, which is a continuation of application No. 11/185,506, filed on Jul. 20, 2005, now abandoned, which is a continuation of application No. 10/148,441, filed as application No. PCT/NL00/00878 on Nov. 30, 2000, now abandoned.

(30) Foreign Application Priority Data

Nov. 30, 1999 (EP) ..................................... 99204044

(51) Int. Cl.
*C08B 3/00* (2006.01)
(52) U.S. Cl.
USPC ........................................................... 536/59
(58) Field of Classification Search
USPC .......................................... 424/278.1; 536/59
See application file for complete search history.

(56) References Cited

U.S. PATENT DOCUMENTS

| 4,243,663 | A | 1/1981 | Azuma et al. |
| 4,746,742 | A | 5/1988 | Hasegawa et al. |
| 5,965,603 | A | 10/1999 | Johnson et al. |
| 2002/0120133 | A1 | 8/2002 | Obaje |

FOREIGN PATENT DOCUMENTS

| DE | 3941061 A1 | 6/1991 |
| EP | 0192296 A1 | 8/1986 |
| EP | 0775494 A1 | 5/1997 |
| EP | 0781559 A2 | 7/1997 |
| EP | 0689454 B1 | 9/1997 |
| GB | 1572368 | 7/1980 |
| GB | 2220211A A1 | 1/1990 |
| WO | WO8404526 A1 | 11/1984 |
| WO | WO9216231 A1 | 10/1992 |
| WO | WO9620008 A1 | 7/1996 |
| WO | WO9620222 | 7/1996 |

OTHER PUBLICATIONS

Turkstra et al., "Chronic Toxicity and Testosterone Inhibitory Effects of Two Potential GnRH Human Prostate Cancer Vaccines in Young Male Pigs", Chapter 8 in a dissertion published on Sep. 29, 2005, pp. 1-25.
Bodewes, et al., "A Single Immunization with CoVaccine HT-Adjuvanted H5N1 Influenza Virus Vaccine Induces Protective Cellular and Humoral Immune Responses in Ferrets", Journal of Virology, pp. 7943-7952; Aug. 2010.
Opposition to EP1233969, Submissions of the Patentee, pp. 1-22; 2010.
Medical News Today, "Start of Phase 2a Clinical Study of Angiotensin Therapeutic Vaccine in Hypertension", Jun. 26, 2008.
Opposition to EP1233969, Auxiliary Request.
Opposition to EP1233969, Table showing presence or absence of features of claim 1 of the Main Request in prior art documents D1-D20.
Opposition to EP1233969, Main Request.
Opposition to EP1233969, Authorsation.
Opposition to EP1233969, Patentee Letter to EPO dated Oct. 11, 2010.
Jones SD, Vaccines Europe-Informa Conference. Vaccine Scale-up and Manufacturing. Dec. 2-3, 2008, Brussels, Belgium.
"Efficacy and Safety Study of the Therapeutic Vaccine PEP223 in Prostrate Cancer Patients", ClinicalTrials.gov., Oct. 11, 2010.
Health-Taking the Temperature of European Healthcare, FluVac-Increased Immunogenicity of Pandemic Influenza Vaccine, European Commission website on Oct. 11, 2010.
Opposition to EP1233969, Hilgers et al., "Synthetic Sulpholipopolysaccharides: Novel Adjuvants for Humoral Immune Responses", Immunology, vol. 60, pp. 141-146; 1987.
Bazin et al., "Synthesis of Sucrose-Based Surfactants through Regioselective Sulfonation of Acylsucrose and the Nucleophilic Opening of a Sucrose Cyclic Sulfate", Carbohydrate Research, vol. 309(2), pp. 189-205; May 1998.
Cox et al., "Adjuvants-A Classification and Review of their Modes of Action", Vaccine, vol. 15. No. 3, pp. 248-256; 1997.
Gupta et al., "Adjuvants for Human Vaccines-Current Status. Problems and Future Prospects", Vaccine, vol. 13, No. 14 pp. 1263-1276; 1995.
Hilgers et al., "Sufolipo-Cyclodextrin in Squalane-In-Water as a Novel and Safe Vaccine Adjuvant", Vaccine, vol. 17, pp. 219-228; Feb. 1999.

(Continued)

*Primary Examiner* — Elli Peselev
(74) *Attorney, Agent, or Firm* — Hoffmann & Baron, LLP

(57) ABSTRACT

The present invention relates to a novel family of monosaccharide derivatives and disaccharide derivatives and to a method of preparation thereof. A mono- and disaccharide derivatives according to the invention comprises at least one fatty acid ester and may further comprise one or more anionic groups and are useful for, inter alia, medical, pharmaceutical, cosmetic and food applications.

3 Claims, 6 Drawing Sheets

(56) References Cited

OTHER PUBLICATIONS

Kotani et al., "Synthetic Lipid A with Endotoxic and Related Biological Activities Comparable to those of a Natural Lipid A from an *Escherichia coli* Re-Mutant", Infection and Immunity, vol. 49, No. 1, pp. 225-237; Jul. 1985.

Kotani et al., "Immunobiologically Active Lipid A Analogs Synthesized According to a Revised Structural Model of Natural Lipid A", Infection and Immunity, vol. 45, No. 1, pp. 293-296; Jul. 1984.

Kumazawa et al., "Importance of Fatty Acid Substituents of Chemically Synthesized Lipid A-Subunit Analogs in the Expression of Immunopharmacological Activity", Infection and Immunity, vol. 56, No. 1, pp. 149-155; Jan. 1988.

Maeda et al., "Adjuvant Activities of Synthetic Lipid A Subunit Analogues and its Conjugates with Muramyl Dipeptide Derivatives", Vaccine, vol. 7, pp. 275-281; Jun. 1989.

Nigam et al., "Effects of Structural Variations in Synthetic Glycolipids Upon Mitogenicity for Spleen Lymphocytes, Adjuvancy for Humoral Immune Response and on Anti-Tumour Potential", BL J. Cancer, vol. 46, pp. 782-793; 1982.

Nigam et al., "Maltose Tetrapalmitate, a Nontoxic Immunopotentiator with Antitumor Activity", Cancer Research, vol. 38, pp. 3315-3321; Oct. 1978.

Takada et al., "Immunopharmacological Activities of a Synthetic Counterpart of a Biosynthetic Lipid A Precursor Molecule and of Its Analogs", Infection and Immunity, vol. 48, No. 1, pp. 219-227; Apr. 1985.

Bazin et al., "Regiospecific Synthesis of New Methyl Sulfoglucopyranoside-Based Surfactants: Nucleophilic Displacement of a Cyclic Sulfate," Synthesis, vol. 4, pp. 621-624; 1999.

Cao et al., "Lipase-Catalyzed Solid Phase Synthesis of Sugar Fatty Acid Esters," Biocatalysis and Biotransformation, vol. 14, pp. 269-283; 1997.

Redmann et al., "Chemoenzymatic Synthesis of Glucose Fatty Esters," Carbohydrate Research, vol. 300, pp. 103-108; 1997.

Akoh et al., "Emulsification Properties of Polyesters and Sucrose Ester Blends I: Carbohydrate Fatty Acid Polyesters," Journal of the American Oil Chemists Society, vol. 69, pp. 9-13; 1992.

Nishikawa et al., "Chemical and Biochemical Studies on Carbohydrate Esters IX. Antitumor Effects of Selectively Fatty Acylated Products of Maltose", Chem. Pharm. Bull. 29(2): 505-513 (1981).

MONO-AND DISACCHARIDE DERIVATIVES

CROSS REFERENCE TO RELATED APPLICATIONS

This application is a Continuation Application of U.S. application Ser. No. 13/162,335, filed on Jun. 16, 2011, abandoned, which is a Continuation Application of U.S. application Ser. No. 12/386,577, filed on Apr. 20, 2009, now U.S. Pat. No. 8,052,981, which is a Continuation Application of U.S. application Ser. No. 11/185,506, filed on Jul. 20, 2005, abandoned, which is a Continuation Application of U.S. application Ser. No. 10/148,441, filed on Oct. 7, 2002, abandoned, which is the U.S. National Phase of International Application Number PCT/NL00/00878, filed on Nov. 30, 2000, which claims benefit of EP 99204044.4, filed Nov. 30, 1999. All of the aforementioned applications are incorporated herein by reference in their entireties.

BACKGROUND OF THE INVENTION

The invention relates to monosaccharide derivatives and disaccharide derivatives and to methods for the preparation thereof. The invention further relates to the use of said derivatives in, inter alia, medical, pharmaceutical, cosmetic and food applications.

Sugar fatty acid esters are well-known for their emulsifying capacity. They can emulsify a large dispersing phase with a small continuous phase in either the oil-in-water and water-in-oil type. In addition, sugar fatty acid esters are well known for their wide range of HLB value (Hydrophylic-Lipophilic Balance, HLB values of sucrose esters may vary from <1 to 16). The HLB value of sugar fatty acid esters depend on the number of fatty esters per sugar molecule and the length of the carbon chain of the fatty acid ester.

Sugar fatty acid esters are further known for several other applications, such as for their ability to enhance or inhibit the crystallization of fats and oils, their anti-bacterial effects, their wetting and dispersing effects, their possible use in the inhibition of thermal and freezing denaturation of proteins, and for their enhancing effect of non-specific host defense.

Nigam et al. (Br. J. Cancer, 46, pp. 782-793, 1982) disclose the in vitro and in vivo immunostimulatory effects of various fatty acid esters of arabinose, galactose, glucose, mannose, cellobiose, lactose, maltose, and sucrose. Factors of increase in antibody responses varied from 1 to <10.

Nigam et al. (Cancer Res. 38, pp. 3315-3312, 1978) disclose immunopotentiating activity of disaccharide fatty acid esters, especially maltose tetrapalmitate.

Nishikawa et al. (Chem. Pharm. Bull. 29, pp. 505-513, 1981) disclose anti-tumor activity of sucrose fatty acid esters.

Azuma (EP 1,572,368) disclose enhancing effects of sugar fatty acid esters on vaccine efficacy, which is designated herein as 'adjuvant activity' or 'adjuvanticity'.

Disaccharide fatty acid esters combined with a oil-in-water emulsion are well-known for their stimulatory effects on vaccine efficacy.

Nigam et al. (Br. J. Cancer, 46, pp. 782-793, 1982) also disclose a combination of sucrose fatty acid esters and oil-in-water emulsions of squalene and their use as adjuvant. However, of sucrose octaoleate esters it has been demonstrated that they show only weak, if any, stimulating effects on vaccine efficacy (see also Examples hereinbelow). Even combinations of sucrose octaoleate esters and an oil-in-water emulsion of squalane, demonstrated weak enhancing effects on vaccine efficacy which makes them inappropriate for the use(s) as vaccine adjuvant (see also Examples herein below).

Sucrose sulfate esters are also well-known. U.S. Pat. No. 3,432,489 discloses a method for the synthesis of various disaccharide polysulfates and of aluminum complexes therefrom, together with their relative therapeutic utilities. This patent, more specifically, describes the reaction of sucrose with many sulfating agents including chlorosulphonic acid or $SO_3$-pyridine in various solvents including pyridine. In addition, U.S. Pat. No. 3,432,489 discloses the pharmaceutical and medical use(s) of sucrose sulfate esters, especially complexes of sucrose octasulfate ester with aluminum salts also known as sucralfate. The application of sucralfate in the treatment of gastro-intestinal disorders is well-known.

WO 90/02133 discloses a method for the preparation of sucrose sulfate esters and aluminum complexes thereof and formulations thereof for medical use(s).

Bazin et al. (Carbohydrate Res. 309, pp. 189-205, 1998) disclose the regioselective synthesis of sucrose-based surfactants through sulphonation of acylsucrose. The disclosed derivatives contain one acyl-group per sucrose molecule and one sulfate group per sucrose molecule. The disclosed method is a regioselective method for derivatization of certain hydroxyl groups of the sucrose molecule. The method uses dibutylstannylene complexes for the blocking of certain hydroxyl groups. A drawback of this method of preparation is its complexity.

Hilgers et al. (Immunology 60, pp. 141-146, 1986) disclose polysaccharides containing both fatty acid esters and sulfate esters, also known as sulpholipo-polysaccharides, and their use as adjuvants in vaccines. In addition, Hilgers et al. (Immunology 60, pp. 141-146, 1986; WO 96/20222) disclose a method of preparation of sulpholipo-polysaccharides by contacting the polysaccharide with an acoylchloride and then with a sulphonating agent.

Mashihi and Hilgers (EP-A-0-295,749) disclose a combination of sulpholipo-polysaccharides and oil-in-water emulsions, especially hydrophilic sulpholipo-polysaccharides with squalane-in-water emulsions. Mashihi and Hilgers (EP-A-0-295,749) further disclose enhancing effects of combinations of sulpholipo-polysaccharides, especially hydrophilic sulpholipo-polysaccharides and oil-in-water emulsions, especially squalane-in-water emulsion, on non-specific host defense mechanisms.

Hilgers et al. (Vaccine 12, pp. 653-660, 1994; Vaccine 12, pp. 661-665, 1994; WO 96/20008; Vaccine 17, pp. 219-228, 1999) disclose combinations of sulpholipo-polysaccharides, especially hydrophobic sulpholipo-polysaccharides and oil-in-water emulsions, especially squalane-in-water emulsions, mineral oil-in-water emulsions, soya oil-in-water emulsions and hexadecane-in-water. A method for the preparation of stable formulations of combinations of sulpholipo-polysaccharides, especially hydrophobic sulpholipo-polysaccharides and oil-in-water emulsions, especially squalane-in-water emulsions, mineral oil-in-water emulsions, soya oil-in-water emulsions and hexadecane-in-water is also disclosed.

The method for the preparation of sulpholipo-polysaccharides as disclosed in WO 96/20008 includes two steps; (1) first, the polysaccharide is contacted with an acoychloride and then (2) the lipidic polysaccharide derivative is contacted with a sulphonating agent. Both steps are considered to be ad random chemical addition reactions, meaning that the probability of each hydroxyl on the polysaccharide molecule being esterified, is equal and does not change during the process. This method of preparation of sulpholipo-polysaccharides results in the formation of different sulpholipo-polysaccharides derivatives varying in the number of fatty acid esters present per polysaccharide molecule, the number of sulfate esters present per polysaccharide molecule, the number of hydroxyl groups per polysaccharide molecule and the distribution of the fatty acid esters, the sulfate esters and the hydroxyl groups over the polysaccharide molecule. The number of chemically distinct sulpholipo-polysaccharides derivatives in a preparation obtained is determined by the number of distinct polysaccharide molecules in the starting material and by the number of hydroxyl groups per polysaccharide molecule.

To illustrate this point of the many, chemically distinct, sulpholipo-polysaccharide derivatives present in a preparation of sulpholipo-polysaccharide, the following example is included as disclosed by Hilgers et al. (WO 96/20008).

The best chemically-defined sulpholipo-polysaccharide derivative preparation known in the art, is the sulpholipo-polysaccharide preparation obtained from beta-cyclodextrin (also known as sulpholipo-cyclodextrin). This sulpholipo-cyclodextrin preparation is obtained from a polysaccharide with 7 glucose molecules per polysaccharide molecule. This sulpholipo-cyclodextrin preparation is derived from the lowest molecular weight polysaccharide and with the least number of hydroxyl groups disclosed. Beta-cyclodextrin has a molecular weight of 1153 Da and has 21 hydroxyl groups per molecule. These hydroxyl groups may be added chemically by a fatty acid ester or a sulfate ester or may remain unchanged. The derivatives present in a sulpholipo-cyclodextrin preparation vary in the number of fatty acid esters per beta-cyclodextrin molecule, the number of sulfate esters per beta-cyclodextrin molecule, the number of hydroxyl groups per beta-cyclodextrin molecule and the distribution of these fatty acid esters, sulfate esters and hydroxyl groups over the beta-cyclodextrin molecule. The number of chemically distinct derivatives in a sulpholipo-cyclodextrin preparation prepared according to the method known in the art (Vaccine 17, pp. 219-228, 1999; WO 96/20222) is extremely high. When the distribution of the fatty acid esters, the sulfate esters and the hydroxyl groups over the beta-cyclodextrine molecule is not taking into account, the number of chemically distinct derivatives in a sulpholipo-cyclodextrin preparation can be several hundreds (e.g. 210). In addition, when the distribution of the fatty acid esters, the sulfate esters and the hydroxyl groups over the beta-cyclodextrine molecule is taken into account, the number of chemically distinct derivatives in a sulpholipo-cyclodextrin preparation is $$3^3+\{(3^3)^7-3^3\}/7=1,494,336,195.$$

The concentration of the chemically distinct derivatives present in a sulpholipo-cyclodextrin preparation can be modulated by varying the molar ratios or the weight ratios of the starting materials, i.e. beta-cyclodextrin, acoylchloride and sulphonating agent, as disclosed by Hilgers et al. (WO 96/20222). The concentration of the chemically distinct derivatives present in a sulpholipo-cyclodextrin preparation can be estimated mathematically. Provided that both chemical reactions involved in the preparation of the sulphoplipo-polysaccharide derivatives are fully ad random, the maximal concentration of a certain derivative present in a sulpholipo-cyclodextrin preparation is most often less than 5%. A preparation of sulpholipo-polysaccharide obtained from a polysaccharide with even larger numbers of hydroxyl groups per molecule than beta-cyclodextrin, will contain an even higher number of chemically distinct derivatives and contains accordingly lower concentrations of each derivative.

Thus it can be concluded that a sulpholipo-polysaccharide preparation obtained as disclosed by Hilgers et al. (WO 96/20222; WO 96/20008) contains many chemically distinct derivatives, which may be disadvantageous under certain circumstances. Also, the fact that a specific derivative is present only in very small amounts could be disadvantageous.

A drawback of the sulpholipo-polysaccharides is that they have various physical, chemical and physicochemical properties (such as solubility, tensio-activity) which while being appropriate for their intended use (e.g. as detergent or emulsifier), are not appropriate for use with other molecules and/or other uses. For this reason, it is desired to separate the 'inappropriate' sulpholipo-polysaccharide derivatives from 'appropriate' sulpholipo-polysaccharide derivatives. Such separation might be carried out by classical separation techniques well-known in the art. However, as has been mentioned, the concentration of the 'appropriate' derivative(s) in a sulpholipo-polysaccharide preparation are relatively low. Also, the chemical and physical properties of the 'inappropriate' sulpholipo-polysaccharide derivatives and of the 'appropriate' sulpholipo-polysaccharide derivatives may be quite similar. Therefore, the separation procedure may be complicated, costly and time-consuming.

A further drawback of the preparation of sulpholipo-polysaccharides as disclosed by Hilgers et al. (WO 96/20222; WO 96/20008) includes the fact that relatively large quantities of organic solvents are used which need to be removed from the final sulpholipo-polysaccharide preparation. This can often prove difficult and/or involve the use of procedures which are difficult, costly, and even dangerous, especially on an industrial scale.

Accordingly, there remains a clear need for sugar derivatives which possess physicochemical and/or biological and/or biopharmaceutical properties that permit a wide use for various purposes. There further remains a need for an easy, safe and inexpensive method for the preparation of such sugar derivatives on an industrial scale.

It is an object of the present invention to provide sugar derivatives which are capable of forming stable formulations with a wide variety of water-immiscible molecules. The objective sugar derivatives should possess highly advantageous physical and/or physicochemical and/or biological and/or pharmaceutical properties, making them suitable for use in a variety of applications, such as medical applications, for instance in the preparation of vaccines and/or adjuvants for vaccines. It is further an object of the invention to provide a simple, easy, and inexpensive method for the preparation of such sugar derivatives.

SUMMARY OF THE INVENTION

The present invention provides sugar derivatives having highly advantageous chemical, physical, and physicochemical properties. These derivatives are the result of various chemical (and/or enzymatic) modifications to monosaccharide and disaccharide molecules.

The present invention relates to a sugar derivative, wherein at least one of the free hydroxyl groups of the monosaccharide molecule (there being three, four or five free hydroxyl groups on the monosaccharide molecule) or of the disaccharide molecule (there being preferably eight free hydroxyl groups on the disaccharide molecule) has been modified. These modifications are a substitution of either the hydrogen atom of the hydroxyl group or of the entire hydroxyl group itself, with one of a large variety of substituting groups. In this fashion, depending upon the number and the type of substitution(s) performed, mono- or disaccharide derivatives may be obtained which possess the desired properties.

In particular, the invention relates to a novel mono- or disaccharide derivative having between one and N−1 fatty acid ester groups, wherein N is the number of hydroxyl groups of the monosaccharide or disaccharide from which the derivative is derived. In a preferred embodiment a mono- or disaccharide derivative further comprises between one and N−1 anionic groups, and wherein the combined number of fatty acid ester groups and anionic groups does not exceed N. The combined number of anionic groups and fatty acid ester groups will be between 1 and N. Preferably, a mono- or disaccharide derivative has not more than two free hydroxyl groups, the combined number of hydroxyl groups, fatty acid esters and anionic groups not exceeding N.

In a preferred embodiment, a disaccharide derivative has at least 2, more preferably 3, even more preferably 4 or 5, most preferred 6, but no more than N−1 fatty acid esters and at least one but not more than N−2, more preferably N−3, even more preferably N−4 or N−5, most preferred N−6 anionic groups, wherein the total combined number of fatty acid esters and anionic groups does not exceed N, and further wherein N is the number of hydroxyl groups of the disaccharide from which the derivatives are derived.

A monosaccharide derivative according to the invention preferably has at least 2, more preferably 3 or 4, but no more than N−1 fatty acid esters and at least one but not more than N−2, more preferably N−3 anionic groups, wherein the total combined number of fatty acid esters and anionic groups does not exceed N, and further wherein N is the number of hydroxyl groups of the disaccharide from which the derivatives are derived.

Thus a particularly preferred derivatised monosaccharide according to the invention has at least one anionic group and at least two fatty acid esters, wherein the total sum of anionic groups and fatty acid esters is in the range of 3-5 and a particular preferred derivatised disaccharide has at least one anionic group, preferably one or four anionic groups, and at least one fatty acid ester, wherein the total sum of anionic groups and fatty acid esters is in the range of 6-8, preferably 7 or 8.

As used herein, the term "fatty acid ester groups" or "fatty acid group" refers to fatty acid ester groups comprising a linear hydrocarbon chain of at least eight carbon atoms. The term "anionic group" as used herein is a negatively charged moiety (i.e. negatively charged at neutral pH or the pH of the environment in which the derivative is applied). Such an anionic group may for example be a sulfate, a sulfonate or a phosphate. Preferred anionic groups include"sulfate ester groups" i.e. groups having the general formula —$SO_2$—OR, and "phosphate ester groups" i.e. groups having the general formula —$PO_2$—$(OR)_2$, wherein R is selected from the group of atoms and/or molecules that form monovalent cations. The term "hydroxyl group" refers to groups having the formula —OH.

The general term "sugar derivatives" as used herein refers to mono- and disaccharide derivatives.

The present sugar derivatives can advantageously be used as emulsifier for water-immiscible molecules. It is noted that the complexation of a water-immiscible molecule with the present sugar derivatives provide significant advantages with respect to the bioavailability, bio-activity and stability of the formulation of the water-immiscible molecule. Improvements in the association between the sugar derivatives and the target molecule may provide concomitant improvements in the bio-availability, biological and/or pharmaceutical activity, and physical properties (for example stability) of the formulation of the water-immiscible molecule. The physicochemical properties of the mono- and disaccharide derivatives according to the invention depend on the number (and ratio) of anionic groups and the number of (to) fatty acid ester groups (and to a lesser extent the number of hydroxyl groups) which are present, as well as the nature of the counter-ion of the anionic group and the type and nature of the fatty acid ester group. Preferably, the present monosaccharide derivative has at least one but no more than 3 or 4 anionic groups, whereas the disaccharide derivative preferably has at least one but no more than 7 anionic groups.

The present sugar derivatives are furthermore highly suitable for use as adjuvant for vaccines. It is noted that the complexation of an antigenic component with sugar derivative according to the invention may provide significant advantages with respect to improving the bioavailability, bio-activity and stability of the formulation of the antigenic component. Improvements in the association between the sugar derivative and the antigenic component may provide concomitant improvement in the efficacy and/or stability of the vaccine and enhance an immune reaction or activate the immune system. The term antigenenic component as used herein, refers to any component or material that is an antigen itself, such as a virus, a bacterium, mycoplasma, a parasite or a tumour cell, a sub-unit of a micro-organism, an allergen, such as a protein, polysaccharide, peptide, glycoprotein, polysaccharide-protein conjugate, peptide-protein-conjugate, and the like or any other entity against which an immune response is intended to be raised. This antigenic component can for example consist of or contain one or more live organisms, inactivated organisms, or so-called subunits (the latter e.g. prepared synthetically, or by recombinant DNA methods, or isolated from the organisms). The term antigenic component further refers to any component that can induce an antigen, e.g. a DNA or RNA sequence that can be incorporated in (the DNA of) a host cell of the immunized subject, where it can induce the formation of antigenic moieties. A vaccine comprising such a nucleotide sequence is also referred to as a DNA vaccine or a RNA vaccine.

Lane 6 (right): (sulfate)1-(dodecanoyl)7-sucrose Fraction-III of Example #2.

Figure 1A:
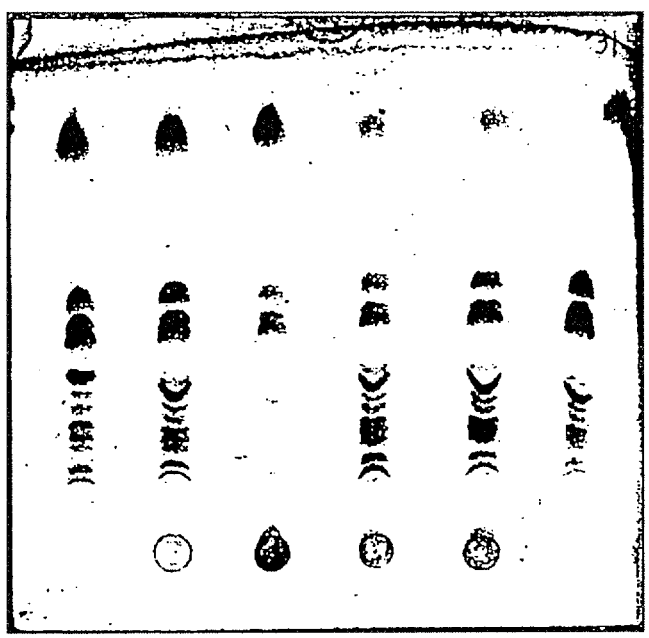
FIG. 1a: Thin layer chromatography of derivatives prepared as described in Example #1.
Lane 1 (left): (sulfate)1-(dodecanoyl)7-sucrose Fraction-III of Example #2;
Lane 2: (dodecanoyl)7-sucrose of Example #1;
Lane 3: (sulfate)1-(dodecanoyl)7-sucrose of Example #1;
Lane 4: (dodecanoyl)-sucrose of Example #1;
Lane 5: (sulfate)1-(dodecanoyl)5-sucrose of Example #1;
Lane 6 (right): (sulfate)1-(dodecanoyl)7-sucrose Fraction-III of Example #2.
Figure 1B:
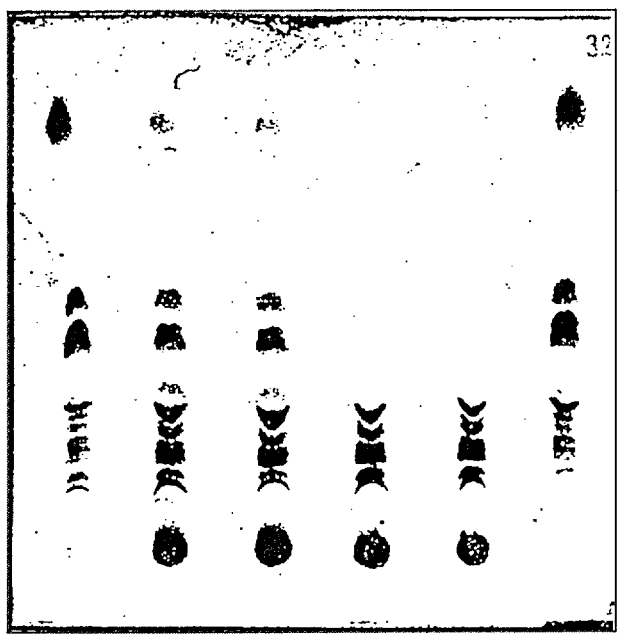
FIG. 1b: Thin layer chromatography of derivatives prepared as described in Example #1.
Lane 1 (left): (sulfate)1-(dodecanoyl)7-sucrose Fraction-III of Example #2;
Lane 2: (dodecanoyl)3-sucrose of Example #1;
Lane 3: (sulfate)1-(dodecanoyl)3-sucrose of Example #1;
Lane 4: (dodecanoyl)1-sucrose of Example #1;
Lane 5: (sulfate)1-(dodecanoyl)1-sucrose of Example #1;
Lane 6 (right): (sulfate)1-(dodecanoyl)7-sucrose Fraction-III of Example #2.
Figure 2A:
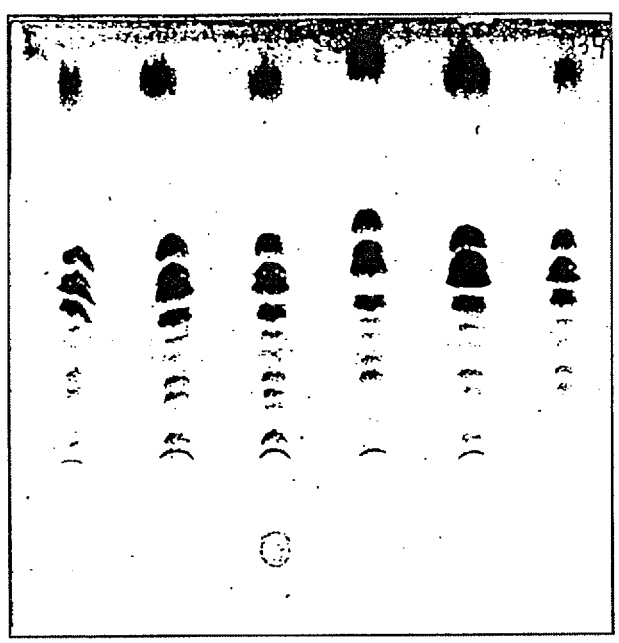
FIG. 2a: Thin layer chromatography of derivatives prepared as described in Example #3.
Lane 1 (left): (sulfate)1-(dodecanoyl)7-sucrose Fraction-III of Example #2;
Lane 2: (dodecanoyl)7-sucrose of Example #3;
Lane 3: (sulfate)1-(dodecanoyl)7-sucrose of Example #3;
Lane 4: (tetradecanoyl)7-sucrose of Example #3;
Lane 5: (sulfate)1-(tetradecanoyl)7-sucrose of Example #3.
Figure 2B:

FIG. 2b: Thin layer chromatography of derivatives prepared as described in Example #3.
Lane 1 (left): (sulfate)1-(dodecanoyl)7-sucrose Fraction-III of Example #2;
Lane 2: (hexadecanoyl)7-sucrose of Example #3;
Lane 3: (sulfate)1-(hexadecanoyl)7-sucrose of Example #3;
Lane 4: (octadecanoyl)7-sucrose of Example #3;
Lane 5: (sulfate)1-(octadecanoyl)7-sucrose of Example #3;
Lane 6 (right): (sulfate)1-(dodecanoyl)7-sucrose Fraction-III of Example #2.

Figure 3A:

FIG. 3a: Thin layer chromatography of derivatives prepared as described in Example #4.
Lane 1 (left): (sulfate)1-(dodecanoyl)7-sucrose Fraction-III of Example #2;
Lane 2: (dodecanoyl)8-sucrose of Example #4;
Lane 3: (sulfate)0.5-(dodecanoyl)7-sucrose of Example #4;
Lane 4: (sulfate)1.0-(dodecanoyl)6-sucrose of Example #4;
Lane 5: (sulfate)1.5-(dodecanoyl)5-sucrose of Example #4;
Lane 6 (right): (sulfate)1-(dodecanoyl)7-sucrose Fraction-III of Example #2.

Figure 3B:
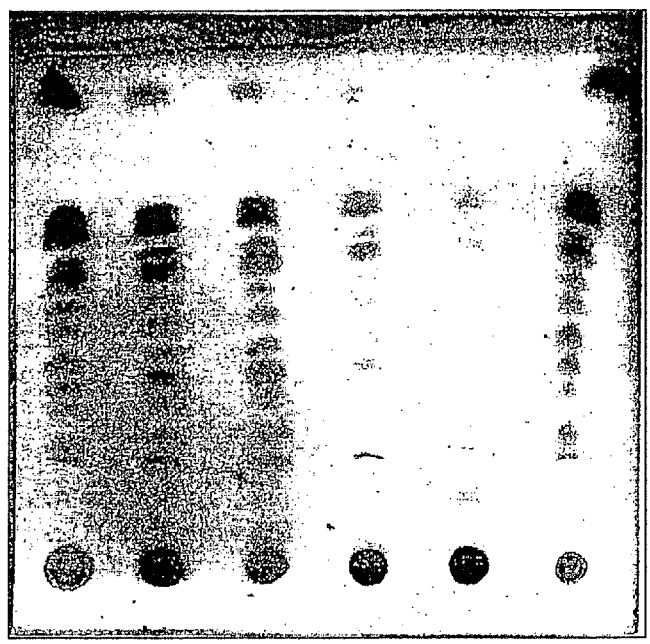

FIG. 3b: Thin layer chromatography of derivatives prepared as described in Example #4.
Lane 1 (left): (sulfate)1-(dodecanoyl)7-sucrose Fraction-III of Example #2;
Lane 2: (sulfate)2.0-(dodecanoyl)4-sucrose of Example #4;
Lane 3: (sulfate)2.5-(dodecanoyl)3-sucrose of Example #4;
Lane 4: (sulfate)3.0-(dodecanoyl)2-sucrose of Example #4;
Lane 5: (sulfate)3.5-(dodecanoyl)1-sucrose of Example #4;
Lane 6 (right): (sulfate)1-(dodecanoyl)7-sucrose Fraction-III of Example #2.

Figure 4A:
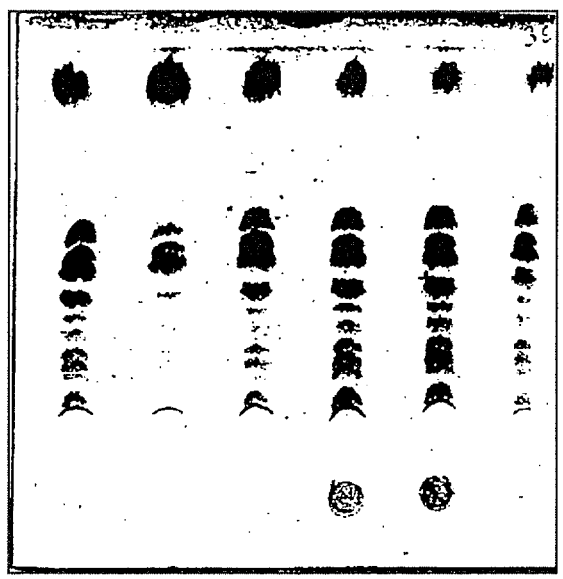

FIG. 4a: Thin layer chromatography of derivatives prepared as described in Example #5.
Lane 1 (left): (sulfate)1-(dodecanoyl)7-sucrose Fraction-III of Example #2;
Lane 2: (dodecanoyl)8-sucrose of Example #5;
Lane 3: (sulfate)1-(dodecanoyl)7-sucrose of Example #5;
Lane 4: (sulfate)2-(dodecanoyl)6-sucrose of Example #5;
Lane 5: (sulfate)3-(dodecanoyl)5-sucrose of Example #5;
Lane 6 (right): (sulfate)1-(dodecanoyl)7-sucrose Fraction-III of Example #2.

Figure 4B:
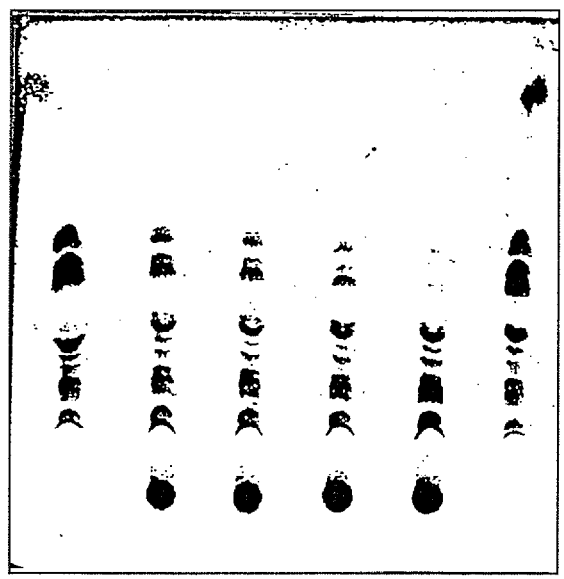

FIG. 4b: Thin layer chromatography of derivatives prepared as described in Example #5.
Lane 1 (left): (sulfate)1-(dodecanoyl)7-sucrose Fraction-III of Example #2;
Lane 2: (sulfate)4-(dodecanoyl)4-sucrose of Example #5;
Lane 3: (sulfate)5-(dodecanoyl)3-sucrose of Example #5;
Lane 4: (sulfate)6-(dodecanoyl)2-sucrose of Example #5;
Lane 5: (sulfate)7-(dodecanoyl)1-sucrose of Example #5;
Lane 6 (right): (sulfate)1-(dodecanoyl)7-sucrose Fraction-III of Example #2.

Figure 5:
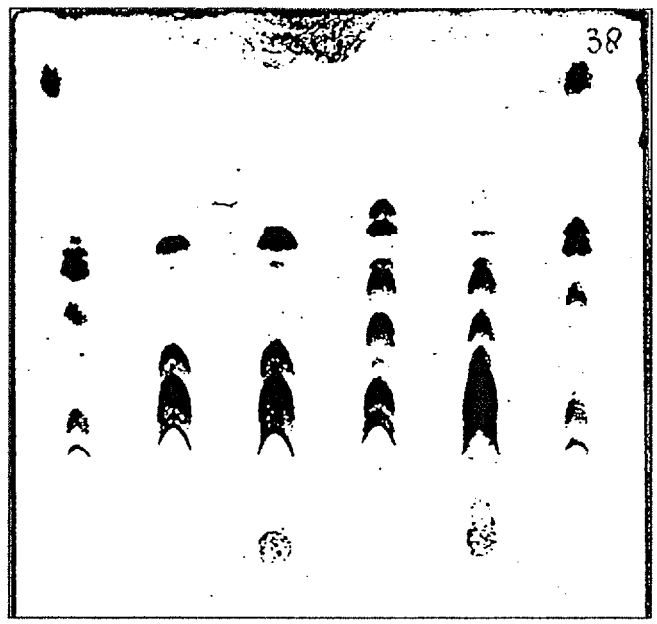

FIG. 5: Thin layer chromatography of derivatives prepared as described in Example #6.
Lane 1 (left): (sulfate)1-(dodecanoyl)7-sucrose Fraction-III of Example #2;
Lane 2: (dodecanoyl)7-maltose of Example #6;
Lane 3: (sulfate)1-(dodecanoyl)7-maltose of Example #6;
Lane 4: (dodecanoyl)7-lactose of Example #6;
Lane 5: (sulfate)1-(dodecanoyl)7-lactose of Example #6;
Lane 6 (right): (sulfate)1-(dodecanoyl)7-sucrose Fraction-III of Example #2.

Figure 6:
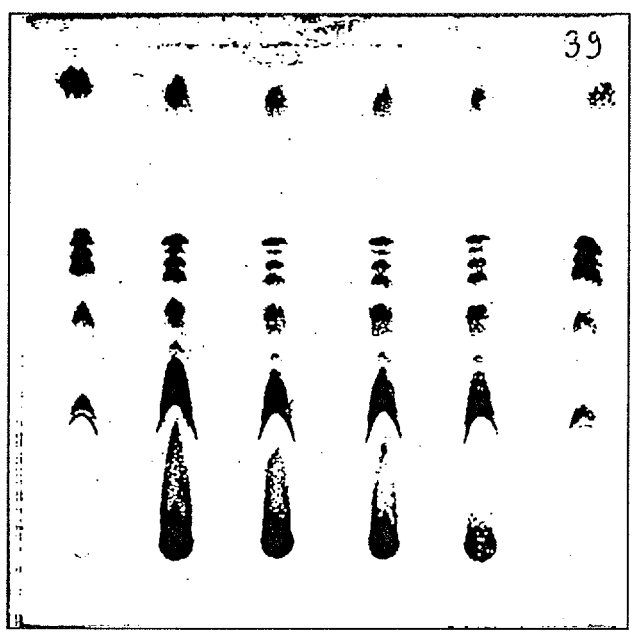

FIG. 6: Thin layer chromatography of derivatives prepared as described in Example #7.
Lane 1 (left): (sulfate)1-(dodecanoyl)7-sucrose Fraction-III of Example #2;
Lane 2: L195 of Example #7;
Lane 3: (sulfate)1-L195 of Example #7;
Lane 4: (sulfate)2-L195 of Example #7;
Lane 5: (sulfate)2.3-L195 of Example #7;
Lane 6 (right): (sulfate)1-(dodecanoyl)7-sucrose Fraction-III of Example #2.

Figure 7:
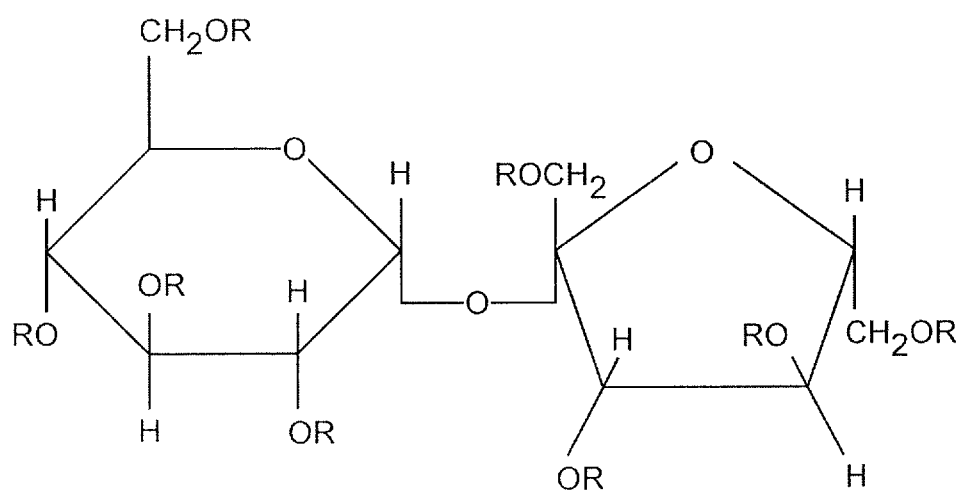

FIG. 7: Chemical structure of sucrose derivative of the present invention wherein R1, R2, R3, R4, R'1, R'2, R'3, and R'4 is H or —O—S(=O)(=O)—OR (wherein R is H, Na, K or $NH_4$) or —O—C(=O)—$(CH_2)_n$—$CH_3$ (wherein n is between 6 to 24).

DETAILED DESCRIPTION OF THE INVENTION

It is preferred that the present monosaccharide derivatives are derived from pentoses with the general formula $C_5H_{10}O_5$ or are from hexoses with the general formula $C_6H_{12}O_6$. Suitable pentoses may be selected from the group consisting of arabinose, ribose, xylose. Suitable hexoses may be selected from the group consisting of allolose, altriose, fructose, galactose, glucose, gulose, inositol, mannose and sorbose. Preferably, the novel monosaccharide derivatives are derived from fructose, galactose or glucose.

The present disaccharide derivatives are preferably derived from disaccharides of the general formula $C_{12}H_{22}O_{11}$ and may suitably be chosen from the group consisting of cellobiose, gentiobiose, lactose, lactulose, maltose, melibiose, sucrose and turanose. Preferably, the novel disaccharide derivatives are derived from lactose, maltose or sucrose. Most preferably, the present sugar derivatives are derived from sucrose.

The fatty acid ester groups are preferably ester groups—having a linear carbon chain—with the general chemical structure of —O—(C=O)—$(CH_2)_x$—$CH_3$ wherein x is between 4 and 24, preferably between 4 and 22, more preferably between 6 and 18 and most preferably between 6 and 14, ester groups with the general structure of —O—(C=O)—$(CH_2)_x$—CH=CH—$(CH_2)_y$—$CH_3$ wherein x+y is between 4 and 24, preferably between 4 and 22 and more preferably between 6 and 14, or groups with the general structure of —O—(C=O)—$(CH_2)_x$—CH=CH—$(CH_2)_y$—CH=CH—$(CH_2)_z$—$CH_3$ wherein x+y+z is between 2 and 20, preferably between 4 and 18 and more preferably between 6 and 14. Combinations of these fatty acid ester groups may also be present.

Particularly preferred fatty acid ester groups with the general structure of —O—(C=O)—$(CH_2)_x$—$CH_3$ are those wherein x is 4 (hexanoic acid), 6 (octanoic acid), 8 (decanoic acid), 10 (dodecanoic acid; also referred to herein as lauric acid), 12 (tetradecanoic acid also known as myristic acid), 14 (hexadecanoic acid also known as palmitic acid), and 16 (octadecanoic acid also known as stearic acid). Preferred fatty acid ester groups with the general structure of —O—(C=O)—$(CH_2)_x$—CH=CH—$(CH_2)_y$—$CH_3$ are those wherein x+y is 14 (for example oleic acid). Preferred fatty acid ester groups with the general structure of —O—(C=O)—$(CH_2)_x$—CH=CH—$(CH_2)_y$—CH=CH—$(CH_2)_z$—$CH_3$ are those wherein x+y+z is 12 (for example linoleic acid).

The anionic group or groups preferably have the general structure —O—SO$_2$—OR or —PO$_2$—(OR)$_2$, wherein R is selected from the group consisting of atoms and/or molecules that form monovalent cations. Examples of members of such a groups include H$^+$, Na$^+$, K$^+$, Li$^+$ or NH$_4^+$. Specific embodiments include sugar derivatives having the sulfate ester groups —O—SO$_2$—OH, —O—SO$_2$—ONa, or —O—SO$_2$—ONH$_4$. Combinations of these sulfate ester groups can also be present.

The invention further relates to an easy, safe and inexpensive method for the preparation of the above mono- and disaccharide derivatives. This method comprises reacting a mono- or disaccharide with an acoylchloride and a sulphonating agent. The mono- or disaccharide may be reacted with said acoylchloride and sulponating agent in any order, or simultaneously.

As will be discussed at length below, it has been found that by either: (1) varying the nature of the monosaccharide or disaccharide used; (2) varying the quantity (ratios) of the various starting materials used; (3) varying the nature of the acoylchloride(s) used; and/or (4) varying the cations(s) employed in the aqueous solution used for purification, different preparations of mono- or disaccharide derivatives may be obtained, which have specific physicochemical properties. Properties of the mono- or disaccharide derivative which may be so adjusted include solubility in aqueous (water) and non-aqueous (non-polar) solvents, the capacity to form micelles and mixed micelles with other molecules, the capacity to adsorb to hydrophobic surfaces, the capacity to adsorb to hydrophilic surfaces, the capacity to adsorb to biologic materials and surface-activity/tensio-activity.

Preferred acoylchlorides are hexanoylchloride, octanoylchloride, decanoylchloride, dodecanoylchloride (lauroylchloride), tetradecanoylchloride (myristoylchloride), hexadecanoylchloride (palmitoylchloride), octadecanoylchloride (stearoylchloride and oleoylchloride), and combinations thereof.

In a specific embodiment, disclosed herein are mono- or disaccharide derivatives having a high water solubility, low solubility in organic solvents, a small capacity to bind hydrophobic molecules and a small capacity to bind to hydrophobic surfaces. In this respect, it is preferred that the acoylchloride is chosen from the group of octanoylchloride, decanoylchloride, dodecanoylchloride, tetradecanoylchloride, and combinations thereof. More preferably in this regard, the acoylchloride is chosen from the group of octanoylchloride, decanoylchloride and/or dodecanoylchloride. Most preferably in this regard, the acoylchloride(s) are decanoylchloride and/or dodecanoylchloride.

In another embodiment, disclosed herein are mono- or disaccharide derivatives having a low water solubility, a high solubility in organic solvents, a large capacity to bind hydrophobic molecules and a large capacity to bind to hydrophobic surfaces. In this respect, it is preferred that the acoylchloride is chosen from the group of dodecanoylchloride, tetradecanoylchloride hexadecanoylchloride, octadecanoylchloride, and combinations thereof. More preferably in this regard, the acoylchloride(s) are tetradecanoylchloride hexadecanoylchloride, and/or octadecanoylchloride. Most preferably in this regard, the acoylchloride(s) are hexadecanoylchloride, and/or octadecanoylchloride.

Preferred sulphonating agents are gaseous SO$_3$, HClSO$_3$ (chlorosulphonic acid), SO$_3$.pyridine, SO$_3$-2-methylpyridine, SO$_3$-2,6-dimethylpyridine, SO$_3$-dimethylformamide, SO$_3$-trimethylamide, SO$_3$-triethylamine, SO$_3$-dimethylanaline, SO$_3$—N-ethylmorpholine, SO$_3$-diethylanaline, SO$_3$-dioxane, and combinations thereof. The sulphonating agent is preferably SO$_3$.pyridine or gaseous SO$_3$.

It is preferred that a mono- or disaccharide is reacted with the acoylchloride(s) in a molar ratio of between 1:1 and 1:N−1, and with the sulphonating agent(s) in a molar ratio of between 1:1 and 1:N−1, wherein the sum of the amount of the acoylchloride(s) ester plus the amount of the sulphonating agent(s) does not exceed N, N being the number of hydroxyl groups of the mono- or disaccharide from which the derivatives are derived. By suitably choosing the molar ratio between the reagents, the skilled person can conveniently prepare a mono- or disaccharide derivative having the desired number of fatty acid ester and sulfate ester groups.

The mono- or disaccharide is preferably reacted with the acoylchloride and sulphonating agent(s) in an anhydrous, aprotic medium. The method is preferably carried out in as small a volume of organic solvent(s) as possible. Preferably, the organic solvent(s) are chosen such that they can easily be removed from the reaction mixture by for instance precipitation, filtration, crystallization or evaporation. Preferred organic solvents are pyridine and N-methylpyrrolidinone. Highly preferred are a mixture of anhydrous dimethylformamide and anhydrous pyridine and a mixture of anhydrous N-methyl-pyrrolidinone and anhydrous pyridine.

If pyridine is used, its amount is preferably less than two times the amount of the acoylchloride used. More preferably, the amount of pyridine used is similar to the amount of acoylchloride.

It is for example possible to react the mono- or disaccharide with the acoylchloride(s), forming a disaccharide fatty acid ester, before it is reacted with the sulphonating agent(s).

The monosaccharide or disaccharide is preferably reacted with the acoylchloride(s) for a period of 4 to 8 hours, preferably about 6 hours, at a temperature of about 60 to 70° C. It may be desired to let the reaction mixture stand hereafter for up to 18 hours at ambient temperature. The reaction with the sulphonating agent(s) is preferably carried out for at least 6 hours at between ambient temperature and 70° C. In a preferred embodiment, the monosaccharide or disaccharide is reacted simultaneously with the acoylchloride(s) and sulphonating agent(s) for at least 6 h at about 60 to 70° C.

It may be desired to let the reaction mixture stand hereafter for up to 18 hours at ambient temperature.

In another preferred embodiment the mono- or disaccharide is first reacted with acoylcholine and with sulphonating agent at ambient temperature and subsequently the temperature is brought to about 50-70° C., preferably 55-70° C. and more preferably to about 60° C.

In this regard, it is noted that the performance of the process at ambient temperature means that the temperature is not critical to the process. Such a feature permits the process to be performed at a wide range of temperatures and under a wide range of conditions with concomitant savings. It is contemplated that an ambient temperature as low as about 10° C. could be acceptable. Preferred ambient temperatures are not lower than about 15° C., more preferably not lower than about 18° C. Further, ambient temperatures are preferably not higher than about 50° C., more preferably not higher than about 40° C., most preferably not higher than about 25° C.

The present mono- or disaccharide derivative is obtained in a two-step reaction of a monosaccharide or disaccharide with an acoylchloride and a sulphonating agent. In a preferred embodiment, this reaction is carried out in one step in simultaneous reaction of the mono- or disaccharide with the acoylchloride and the sulphonating agent. Of course it is also possible to start from a monosaccharide fatty acid ester or disaccharide fatty acid ester, for example the sucrose lauric acid ester L-195 (Mitsubishi, Japan), sucrose lauric acid ester L-595 (Mitsubishi™, Japan), or sucrose stearic acid ester S-195 (Mitsubishi, Japan), and reacting this starting material with one or more sulphonating agent(s) to form the desired mono- or disaccharide derivative.

As has been mentioned, it is preferred that as small an amount of organic solvents as possible is used. In this respect it is preferred that the mono- or disaccharide is dissolved in the organic solvent(s) by heating resulting in a transparent, homogeneous solution. In particular this method of preparing a homogenous solution is suitable for sugars which are relatively poor soluble in the organic solvents or are difficult to dissolve in the organic solvents, for example sucrose and lactose. To dissolve these sugars in the least quantity or volume of organic solvents, the temperature is increased to >80° C. Preferably, the temperature of the organic solvents is increased to >90° C.

In a preferred embodiment, after the reaction is completed, the mono- or disaccharide derivatives in the organic solvents are neutralized with a solution of NaOH, $NH_4OH$, KOH, resulting in mono- or disaccharide derivatives having sulfate ester groups including one of the cations $Na^+$, $K^+$ or $NH_4^+$.

The objective mono- or disaccharide derivatives may be recovered by cooling resulting in the formation of two or three or more distinct phases of which one is rich in the mono- or disaccharide derivatives. This can be recovered by methods well known in the art including filtering, decanting, and the like. Residual organic solvents are removed from this phase by for example evaporating at increased temperature and reduced pressure, or washing with an aqueous phase. The organic solvent(s) and any by-products formed during the reaction will be present, after cooling, in one or two phases, which contain no, or hardly any, of the mono- or disaccharide derivatives. This phase or these phases may be removed by methods well known in the art including filtration, decantation, and the like. The derivatized saccharide may be further purified by other techniques known in the art.

The mono- or disaccharide derivatives can be extracted from the reaction mixture using a liquid immiscible with the organic solvents used for the preparation of the mono- or disaccharide derivatives. Hereby, the mono- or disaccharide derivatives are separated or isolated from the by-products and organic solvent(s) used for the preparation thereof. In this respect, it is preferred that said liquid is a volatile organic solvent or is an ingredient of the final formulation of the sugar derivative. It is further preferred that said liquid is an oil, the final formulation being an emulsion. Most preferably, said liquid is squalane.

The two chemical reactions involved in the synthesis of the monosaccharide derivatives and disaccharide derivatives of the present invention are believed to be ad random reactions, resulting in a collection of different mono- or disaccharide derivatives, which vary in the number of sulfate ester groups per mono- or disaccharide molecule and/or vary in the number of fatty acid ester groups per mono- or disaccharide molecule, and thus vary in the structure and physicochemical properties possessed thereby.

It is however noted that the number of chemically distinct derivatives in a preparation of mono- or disaccharide derivatives is considerably lower than in preparations of sulpholipo-polysaccharide disclosed by Hilgers et al. WO 96/20222, WO 967/20008) as discussed in length above. If the distribution of the fatty acid ester groups, the sulfate ester groups and the hydroxyl groups over the disaccharide molecule is not taken into account, the number of distinct derivatives in a preparation obtained from a disaccharide with 8 hydroxyl groups according to the present invention is 28. If the distribution of the fatty acid ester groups, the sulfate ester groups and the hydroxyl groups over the disaccharide molecule is taken into account, the number of distinct derivatives obtained from a disaccharide with 8 hydroxyl groups according to the present invention is $3^8$=6,561. These lower numbers as compared to those of sulpholipo-cyclodextrin (which were 210 and 1,494, 336,195, respectively) have considerable advantages with respect their use(s) and preparation.

The present method for preparing a mono- or disaccharide derivative accordingly leads to a mixture of such derivatives. These derivatives may be separated by using techniques such as crystallization, precipitation, filtration, evaporation, dialysis or ultrafiltration. It is preferred that removal of the organic solvent(s) used and by-products formed is carried out simultaneously with the separation of the different mono- and disaccharide derivatives obtained. This is preferably accomplished by phase separation, chromatography, precipitation, dissolving, extraction, or a combination of such techniques. More preferably, the mono- or disaccharide derivatives are separated from the organic solvent(s) by lyophilizing whereby a dry mono-derivative or disaccharide derivative preparation is obtained. Preferably, such lyophilization is performed at room temperature, at an internal pressure of less than 10 mbar and a cold trap of less than −25° C.

In particular, disclosed herein is a method for preparing a preparations rich in disaccharide derivatives having specific numbers and types of fatty acid ester groups and anionic groups by the steps of contacting about 1 mole of disaccharide with about 7 moles of acoylchloride(s) for each fatty acid ester group per disaccharide molecule prepared thereby and with about 1 mole of sulphonating agent(s) for each sulfate ester group or about 1 mole of phosphonating agent(s) for each phosphate ester per disaccharide molecule prepared thereby, wherein the total number of moles of acoylchloride(s) and of sulphonating agent(s) do not exceed N, and wherein N is the total number of hydroxyl groups of the disaccharide contacted.

The water solubility of preparations of the present mono- or disaccharide derivatives may be increased by (1) increasing the quantity of sulphonating agent(s) or phosphonating agent(s) employed in the method of the present invention and/or by decreasing the quantity of acoylchloride(s) employed in the method of the present invention, so that mono- or disaccharide derivatives having greater numbers of anionic groups are provided relative to the number of fatty acid ester groups present. A high water solubility may also be achieved by (2) employing acoylchloride(s) with short carbon chains, providing mono- or disaccharide derivatives having fatty acid ester groups with relatively short carbon chains. This may particularly be accomplished by employing octanoylchloride decanoylchloride, dodecanoylchloride (lauroylchloride) and/or tetradecanoylchloride, as the acoylchloride reagent(s).

The water solubility may be decreased, or the solubility in non-polar solvents may be increased by taking the opposite actions. This may particularly be achieved by employing dodecanoylchloride (lauroylchloride), tetradecanoylchloride and/or octanoylchloride, as the acoylchloride reagent(s). The same measures increase the capacity of the mono- or disaccharide derivatives to bind to hydrophobic surfaces.

The capacity of the present mono- or disaccharide derivatives to form micelles may be provided by increasing the quantity of sulphonating or phosphonating agent(s) employed in the method of the present invention and by increasing the quantity of acoylchloride(s). The same measures lead to an increase in surface-activity/tensio-activity.

In this regard it is noted that the present mono- and disaccharide derivatives can form large mixed micelles with other compounds. For example, monosaccharide derivatives with sulfate ester/fatty acid ester-ratio of 1 sulfate ester group and 3 fatty acid ester groups per monosaccharide molecule, or disaccharide derivatives with sulfate ester/fatty acid ester-ratio of 1 sulfate ester group and 7 fatty acid ester groups per disaccharide molecule, have been found to form mixed micelles with polysorbate 80. These micelles do not pass ultrafiltration membranes with a high molecular weight cut-off. The size of the mixed micelles with other compounds depends on the ratio of the hydrophilic groups (i.e. sulfate esters) and the hydrophobic groups (i.e. fatty acid esters) and on the physical features of the molecule to be associated therewith.

Preparations rich in mono- or disaccharide derivatives having specific numbers and types of anionic groups—e.g. sulfate ester groups—and fatty acid ester groups, have been found capable of forming complexes with particular water-immiscible molecules, for example food ingredients, pigments, flavors, oils, drug molecules and antigens, which are capable of modifying the stability, reactivity, mobility and/or bio-availability of the particular molecule.

The present mono- and disaccharide derivatives may be employed in various medical and pharmaceutical applications.

The mono- and disaccharide derivatives according to the invention, when complexed with a molecule (such as a drug molecule or antigenic compound), provide improved bio-availability of the molecule from solid, semi-solid and/or liquid formulations. They also provide enhanced stability and improved shelf-life. Further, they reduce the side-effects (toxicity) of the molecule with which it formed a complex. Finally, they make possible the provision of uniform easy-to-handle injectable solutions (from poorly-soluble drugs).

An example of a medical application wherein the use of the present mono- and disaccharide derivatives (and preparations thereof) leads to great advantages is in vaccine adjuvants. Suitable adjuvants include those commonly referred to as oil-in-water emulsions (including squalane-in-water, mineral-oil-in-water, hexadecane-in-water, soya-oil-in-water, sucrose fatty acid esters-in-water, and the like), water-in-oil emulsions (including water-in-mineral oil, water-in-squalane, water-in-sucrose fatty acid ester, and the like) or water-in-oil-in-water emulsions (including water-in-mineral oil-in-water, water-in-squalane-in-water, water-in-sucrose fatty acid ester-in-water, and the like).

Vaccination is one of the most cost-effective means to prevent and to control infectious diseases in both human and animal health. Vaccination or immunization includes the generation of sufficiently levels and duration of the adequate type (or types) of immune responses against the relevant antigenic component (or components) and/or epitope (or epitopes). The immune response can be determined by for example antibody titres in serum, proliferative responses of lymphocytes, degree protection against an artificial or natural infection, duration of protection, numbers on non-responding animals, and the like.

In many target animal species for example pigs, cattle, poultry, dogs, cats, horses, humans, and the like, diseases caused by viruses, bacteria, parasites or any other infectious agents for example influenza virus, hepatitis virus, measles virus, polio virus, parvovirus, rabiesvirus, *Streptococcus, Meningococcus, Clostridium, Escherichia, Salmonella, Campylobacter, Actinobacillus, Listeria*, malaria, trypanosome, lungworm, protozoa, mycoplasma, *Chlamydia*, and the like, can be prevented or controlled by vaccination.

In most cases, the immune response against inactivated antigens and some cases also against live antigens is too low to establish a sufficient level of protection or a sufficient duration of the protection. Therefore, adjuvants are added to these antigens which stimulate the immune response.

The ideal adjuvant enhances the relevant type(s) of immune response (humoral and/or cellular) against the antigen(s) and/or epitope(s) relevant for protection, without significant side-effects. An adjuvant that stimulates a certain type (or types) of immunity may be appropriate for some use(s) but inappropriate for other use(s). In addition, an adjuvant that stimulates immunity against certain antigens may be appropriate for some use(s) but not for other use(s). A strong adjuvant enhances for example antibody-mediated and cell-mediated immunity against many different antigens. The distinct effects of an adjuvant on different antigens is a clear drawback, especially in relation to combination vaccines containing several different antigens. Adjuvants that exert strong activity with respect to type(s) of antigen, animal species, type(s) of immune responses have important advantages.

In case an adjuvant is used in a DNA or RNA vaccine, that can induce antigens in vivo the adjuvant preferably also assists the successful incorporation of the DNA or RNA sequence in the DNA of the host cell (transfection).

Many different types of adjuvants are known but only a few are applied in commercial human or veterinary vaccines. The type of adjuvant selected for a vaccine is determined by several factors including the target animal species, the efficacy of the adjuvant, the toxicity of the adjuvant, the quality of the adjuvant, the cost price of the adjuvant, and the like. It is well-known that efficacy and toxicity of adjuvants are associated in that high efficacy is accompanied by high toxicity and low toxicity with low efficacy. High toxicity is manifested as local reactions for example inflammation, swelling, abscess formation, granuloma, necrosis, and the like and/or systemic reactions for example pain, fever, hypertension, anaphylaxis, anorexia, weight-loss, and the like. The toxicity of an adjuvant is an important limitation for its use and while it may be acceptable in some animal species it may not be acceptable in another animal species.

In laboratory animals, the standard adjuvant is Freund's complete adjuvant which is a strong adjuvant. Due to its toxicity, especially its local effects, it can not be applied in humans or food animals or companion animals. In food animals such as cattle, sheep and pigs, emulsions of mineral oil are often the adjuvant of choice. Examples include mineral oil-in-water emulsions (O/W), water-in-mineral oil emulsions (W/O) and water-in-mineral oil-in-water emulsions (W/O/W). These adjuvants produce high immune responses (but less than Freund's complete adjuvant). Toxicity including local and systemic side-effects, circumvents their application in companion animals and humans. In companion animals such as cats, dogs and horses, relatively safe adjuvants are applied for example ISCOMs, $Al(OH)_3$ and polyacrylates. In general, these adjuvants induce lower responses than mineral oil emulsions but also less detrimental side-effects. In humans, aluminum salts are the only adjuvants licensed. They evoke lower immune responses than many of the adjuvants used in veterinary vaccines but are considered relatively safe.

Thus, a drawback of strong adjuvants is their relatively high toxicity. A drawback of safe adjuvants is their relatively low efficacy.

In addition to efficacy and toxicity, the quality of the adjuvant and of vaccines containing the adjuvant is crucial. Criteria of quality include viscosity, chemical stability, physical stability, physicochemical stability, and the like. A high viscosity hampers the handling of the product, for example the aspiration of the product into a syringe or the administration of the product to the animal. A low viscosity facilitates the handling of the product. Low chemical, physical or physicochemical stabilities reduce the shelf-live of a vaccine and demand for strict conditions for storage and transport of the product. High chemical, physical and physicochemical stability result in a long shelf-live and facilitates the logistics of the product. It is well-known that vaccines containing emulsions of mineral oil used in food animals, have increased viscosity and are prone to instability.

From the above, it becomes clear that there is still an urgent need for adjuvants that have a high efficacy and low toxicity, are effective against a broad range of antigens and are easy to handle.

The present invention provides for such an adjuvant. It has been found that the above described mono- and disaccharide derivatives are highly suitable for use as an adjuvant in various types of vaccines. The invention thus also relates to an adjuvant in the form of a mono- or disaccharide derivative according to the invention and to a adjuvant formulation for preparing a vaccine comprising one or more of said mono- or disaccharide derivatives. The adjuvant formulation may further comprise a pharmaceutically acceptable carrier. Examples of suitable carriers include physiological salt solutions and oil-in-water emulsions, preferably squalene-in-water emulsions.

A particularly preferred adjuvant formulation according to the invention comprises a a mono- or disaccharide derivative (I) according the invention, a water-immiscible liquid phase or water imiscible solid phase (II), an emulsifier or stabilizer (III) and optionally an aqueous phase (IV).

Any of the sugar derivatives according to the invention may be employed as an adjuvant. The derivative may for example be a pentose with 1-3, preferably 1 or 2 fatty acid groups and 0-3, preferably 1 or 2 anionic groups, wherein the sum of the anionic and fatty acid groups does not exceed 4.

A hexose derivative with 1-4, preferably 1-3, fatty acid groups and 0-4, preferably 1-3 anionic groups wherein the sum of the anionic and fatty acid groups does not exceed 5, is also particularly suitable for use as an adjuvant according to the invention.

A preferred disaccharide derivative as an adjuvant may comprise 1-7, more preferably 3-7, most preferably 4-7 fatty acid groups and 0-7, more preferably 0-6, most preferably 1-5 anionic groups, wherein the sum of the anionic and fatty acid groups does not exceed 8.

Particularly good results have been achieved with a disaccharide derivative having one anionic group, preferably a sulfate ester group and 5-7 fatty acid ester groups. A derivatized disaccharide having four anionic groups, preferably sulfate ester groups, and four fatty acid ester groups also showed very satisfying performance as an adjuvant.

One or more sugar derivatives according to the invention are usually present as an adjuvant in an adjuvant formulation according to the invention in a concentration of 0.1-1000 g/l, preferably of 0.5-500 g/l and more preferably 1-320 g/l.

The water-immiscible liquid phase is preferably an oil. Suitable oils include, for example, soybean oil, peanut oil, canola oil, olive oil, safflower oil, corn oil, mazola oil, cod liver oil, almond oil, cottonseed oil, ethyl oleate, isopropyl myristate, isopropyl palmitate, mineral oil, myristyl alcohol, octyldodecanol, persic oil, sesame oil, myristyl oleate, cetyl oleate, and myristyl palmitate. Other suitable oils include biocompatible oils consisting of saturated, unsaturated, and/or partially hydrogenated fatty acids, silicon-based oils, synthetic oils such as triglycerides composed of saturated and unsaturated chains of $C_{12}$-$C_{24}$ fatty acids, such as for example the glycerol triglyceride ester of oleic acid, terpenes, linolene, squalene, squalane, squalamine, and fluorinated oils including perfluoro-compounds known as FC-40, FC-43, Fc-72, FC-77, FC-70, FC-75, perfluorohexane, perfluorooctylbromide (also known as perfluorobron), perfluorooctyl iodine, or a mixture thereof.

Very good results have been achieved with an adjuvant formulation, wherein the water-immiscible phase (II) is a squalane, squalene, mineral oil, plant oil, hexadecane, fluorocarbon or a silicon oil.

The water-immiscible phase (II) is typically present in an adjuvant formulation in a concentration varying from 0-640 g/l, preferably 0-480 g/l and more preferably 10-320 g/l.

In case the adjuvant formulation comprises a water-immiscible solid phase, such a solid phase is preferably a salt that is insoluble in water. Particularly suitable are insoluble aluminum or calcium salts or mixtures thereof. Preferred salts include aluminumhydroxide, aluminum phosphate, calcium phosphate silica and mixtures thereof.

The stabilizer of emulsifyer (III) may be a detergent. Suitable emulsifying and/or stabilising agents including, for example, cholesterol, diethanolamine, glyceryl monostearate, lanolin alcohols, lecithin, mono- and di-glycerides, mono-ethanolamine, oleic acid, oleyl alcohol, poloxamer, for example, poloxamer 188, poloxamer 184, poloxamer 181, nonionic block polymers (e.g. PLURONICS of BASF), polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic, Triton X-100, saponines, purified saponins (e.g. QS21), polymers (e.g. polyacrylates).

Particularly good results have been achieved with an adjuvant formulation, wherein the emulsifyer or stabilizer (III) is a non-ionic detergent with a hydrophilic-lipophilic balance value of more than 10, a sugar fatty acid ester, or an anionic detergent with a hydrophilic-lipophilic balance value of more than 10.

Preferred emulsifyers or stabilizers (III) include polysorbate 20, polysorbate 80, polysorbate 85, Triton-X 100, saponin, a lecithin, a non ionic block copolymer, a sucrose fatty acid ester, a sugar lauric acid esters e.g. Ryoto sugor ester L1695 of Mitsubishi-Kagaku Food corporation. Particularly preferred are polysorbate 80, and sucrose fatty acid esters.

A mono- or disaccharide according to the invention may also advantageously be used as an emulsifier or stabilizer (III) in an adjuvant formulation. Particularly good results have been obtained with a mono- or disaccharide derivative having at least 3, preferably at least 4, but no more than N−1 anionic groups and at least 1 but no more than N−3, preferably no more than N−4, fatty acid ester groups wherein N is the number of hydroxyl groups of the mono- or disaccharide from which the derivative is derived and wherein the combined number of fatty acids and anionic groups does not exceed N.

One or more emulsifyers or stabilizers are typically present in an adjuvant formulation according to the invention in a total concentration from 0 to 640 g/l, preferably 1-480 g/l and more preferably 1-320 g/l.

Suitable aqueous phases (IV) include, for example, saline, phosphate buffered saline, citrate buffered saline, isotonic ionic solutions, isotonic non-ionic solutions and the like. The amount of aqueous phase may vary widely, and will usually be from 0 an 999.9 g/l, preferably from 10-990 g/l and more preferably from 640-990 g/l.

The invention further relates to a vaccine comprising an antigenic compound and a mono- or disaccharide derivative according to the invention, optionally in an adjuvant formulation according to the invention. Such a vaccine may comprise 0.05-250 g/l, preferably 0.25-125 g/l, and more preferably 1-80 g/l of a mono- or disaccharide derivative as an adjuvant or a mixture of such derivatives. It may further comprise one or more emulsifyers or stabilizers in a total concentration from 0 to 640 g/l, preferably 1-480 g/l and more preferably 1-320 g/l and an water-immiscible liquid phase, preferably an oil, in a concentration varying from 0 to 640 g/l, preferably 1-480 g/l and more preferably 1-320 g/l.

The vaccine may contain any antigenic component as described above. For the preparation of the vaccines the antigenic component is mixed either well before or just prior to use.

A vaccine according to the invention may for example be used for immunization of humans and animals (the latter includes for example mammals, birds, and rodents, for example pigs, cattle, sheep, horses, dogs, cattle, and poultry).

The vaccine, the adjuvant or the adjuvant formulation may be applied by a parenteral or nonparental route for example intramuscular, intradermal, transdermal subcutaneous, intraperitoneal, intracutaneous, intranasal, nasal, oral, intravaginal, intracloacal, and the like.

It is noted that the invention also envisages the use of a combination of a known adjuvant and an adjuvant in the form of the present mono- or disaccharide derivative.

With respect to food animals, the present adjuvant has several advantages over already-applied adjuvants for example less local and systemic side-effects, less discomfort of vaccination to the animals, less economic losses as a result by decreasing the detrimental effects on the body weight gain, less economic losses as a result of loss of meat containing vaccine residues, lower risk of auto-injection to the vaccine applicant, improved easiness of handling of the vaccine, improved stability of the product, and the like.

In companion animals, the present adjuvant has several advantages over already-applied, known adjuvants for example higher levels of the immune response, improved duration of the immune response, increased number of responding animals, a larger number of antigens that can be combined with the adjuvant, and the like.

The invention will now be further elucidated by the following, non-restrictive examples.

EXAMPLES

Some of the experiments described in the examples below were carried out simultaneously. In order to facilitate comparison, results of selected groups are presented per example. The consequence is that results of the control group(s) are presented in several examples.

Example #1

Sucrose derivatives were synthesized as described previously for the so-called sulpholipo-polysaccharides (Hilgers et al., 1986). Briefly, finely-powdered sucrose (Merck) was dried by heating for about 6 h at 90° C. at <50 mbar and anhydrous N-methylpyrrolidinone (NMP; Merck) and anhydrous pyridine (Merck) were added. The mixture was stirred at about 80° C. until a clear solution was obtained. Dodecanoylchloride (Merck) was added and the reaction mixtures were kept for about 6 h at 60° C. $SO_3$.pyridine (Merck) was added and the reaction mixtures were incubated for about 18 h at room temperature. The pH was adjusted at 7.0 (±0.3) with 4 M NaOH. N-methylpyrrolidinone and pyridine were removed by extensive evaporation (>6 h) at increased temperature (<80° C.), reduced pressure (<10 mbar) and condensation at 4° C., until the weight loss of the residue was less than 0.1 g per 30 min. The quantities of the starting materials employed for the different derivatives are set forth in Table #1.1.

TABLE #1.1

| Sucrose derivative | Sucrose (g) | Dodecanoyl-chloride (g) | $SO_3$•pyridine (g) | NMP (g) | Pyridine (g) | Molar ratios | |
|---|---|---|---|---|---|---|---|
| | | | | | | L/sucrose | S/sucrose |
| (dodecanoyl)7-sucrose | 6.8 | 30.7 | 0.0 | 30.1 | 15.8 | 7.0 | 0.0 |
| (sulphate)1-(dodecanoyl)7-sucrose | 6.8 | 30.7 | 3.2 | 30.1 | 15.8 | 7.0 | 1.0 |
| (dodecanoyl)5-sucrose | 6.8 | 21.9 | 0.0 | 30.1 | 15.8 | 5.0 | 0.0 |
| (sulphate)1-(dodecanoyl)5-sucrose | 6.8 | 21.9 | 3.2 | 30.1 | 15.8 | 5.0 | 1.0 |
| (dodecanoyl)3-sucrose | 6.8 | 13.1 | 0.0 | 30.1 | 15.8 | 3.0 | 0.0 |
| (sulphate)1-(dodecanoyl)L3-sucrose | 6.8 | 13.1 | 3.2 | 30.1 | 15.8 | 3.0 | 1.0 |
| (dodecanoyl)1-sucrose | 6.8 | 4.4 | 0.0 | 30.1 | 15.8 | 1.0 | 0.0 |
| (sulphate)1-(dodecanoyl)1-sucrose | 6.8 | 4.4 | 3.2 | 30.1 | 15.8 | 1.0 | 1.0 |

Molar ratio: L/Sucrose: mole dodecanoylchloride per mole sucrose; S/sucrose: mole $SO_3$•pyridine per mole sucrose.

The products obtained were analysed by thin layer chromatography (TLC). Samples of 0.5 g of derivative were dissolved in 4.5 ml NMP and 2 μl of each solution obtained were applied on silicagel TLC plate (HPLC-TLC, normal phase; Analtech, Newark; Del., USA) and eluted with a mixture of 233 ml diethylether+100 ml n-hexane+3.3 ml acetic acid. Spots were visualised by spraying the plate with a solution of 50 v/v % sulphuric acid in methanol and heating the plates for 10-30 min at 120° C. The results are set forth in FIG. #1.

Formulations of the different sucrose derivatives of Table #1.1 were prepared by mixing 10 g of the sucrose derivative with 10 g of polysorbate 80 (ICI) and 40 g of squalane (Merck) and 190 g of a solution of 0.01 w/v % thimerosal (Sigma) phosphate buffered saline (PBS-thimerosal; pH 7.0). Each mixture obtained was emulsified by three passages through a Microfluidizer Model Y110 (Microfluidics Corp., Newton, USA) at an internal pressure of at least 400 bar and at ambient temperature. Each emulsion was inspected under the microscope. The emulsification procedure was repeated if per 10 fields inspected more than 10 oil droplets with a diameter greater than 1 μm were visible under the microscope at 1000 fold magnification. The emulsions obtained were stored at 4° C., until use.

The adjuvant activity of these formulations was determined in pigs. Vaccines were prepared by mixing one volume of either formulation with one volume of an antigen formulation containing 32 μg/ml classical swine fever virus glycoprotein E2 (CSFV-E2; ID-DLO, Lelystad, The Netherlands) produced in insect cells as described by Hulst et al. (1994).

Groups of five pigs (10 weeks of age) were immunised intramuscularly with 2 ml vaccine per animal. Three weeks later the immunisation was repeated with the same vaccine. Three weeks after the second immunisation, the antibody titres against CSFV-E2 in serum were measured by virus neutralisation assay as described by Terpstra et al. (Vet. Microbiol. 9, pp. 113-120, 1984). The geometric mean titre (GMT), the standard deviation (STDEV) of each group and the antilog (2 exponent GMT) were calculated. Results are set forth in Table #1.2.

Sulpholipo-cyclodextrin/squalane-in-water emulsion (SL-CD/squalane/polysorbate 80; Hilgers et al., Vaccine 17, pp. 219-228, 1999) was included in the animal experiment.

TABLE #1.2

| | Vaccine | | 2-log CSFV-neutralising antibody titre in serum 3 weeks post-boost | | |
|---|---|---|---|---|---|
| Group | Antigen | Adjuvant formulation | GMT | STDEV | antilog |
| 1 | CSFV-E2 | No adjuvant | 3.32 | 0.00 | 10 |
| 2 | CSFV-E2 | Squalane/polysorbate 80 [160/40] | 3.84 | 1.12 | 14 |
| 3 | CSFV-E2 | (dodecanoyl)7-sucrose/squalane/polysorbate 80 [40/160/40] | 10.36 | 1.35 | 1,311 |
| 4 | CSFV-E2 | (sulphate)1-(dodecanoyl)7-sucrose/squalane/polysorbate 80 [40/160/40] | 14.47 | 0.78 | 22,739 |
| 5 | CSFV-E2 | (dodecanoyl)5-sucrose/squalane/polysorbate 80 [40/160/40] | 10.24 | 2.29 | 1,208 |
| 6 | CSFV-E2 | (sulphate)1-(dodecanoyl)5-sucrose/squalane/polysorbate 80 [40/160/40] | 11.07 | 1.72 | 2,154 |
| 7 | CSFV-E2 | (dodecanoyl)3-sucrose/squalane/polysorbate 80 [40/160/40] | 11.56 | 1.82 | 3,011 |
| 8 | CSFV-E2 | (sulphate)1-(dodecanoyl)3-sucrose/squalane/polysorbate 80 [40/160/40] | 11.16 | 1.57 | 2,282 |
| 9 | CSFV-E2 | (dodecanoyl)1-sucrose/squalane/polysorbate 80 [40/160/40] | 9.39 | 1.90 | 671 |
| 10 | CSFV-E2 | (sulphate)1-(dodecanoyl)1-sucrose/squalane/polysorbate 80 [40/160/40] | 9.91 | 0.00 | 960 |
| 11 | CSFV-E2 | SL-CD/squalane/polysorbate 80 | 13.36 | 1.56 | 10,484 |

GMT = geometric mean titre, i.e. the mean value of the 2log titres of the individual animals of the same group; STDEV: standard deviation; antilog = 2exponent(GMT).

Example #2

34.2 g (0.1 mole) anhydrous sucrose (Merck), 149 g (1.5 mole) anhydrous N-methyl-pyrrolidinone and 79 g (1 mole) anhydrous pyridine were fed in a round bottom flask which was then connected to a Rotavapor™ (Buchi, Switzerland) and mixed by rotation. The mixture heated to 90° C., until a clear solution was obtained. The temperature was adjusted at 60° C. and 153.3 g (0.7 mole) dodecanoylchloride were fed to the sucrose solution. The reaction mixture in the flask was kept at 60° C. for 6 hours. 15.9 g (0.1 mole) SO3.pyridine were fed to the reaction mixture in the flask and the reaction mixture was kept at 60° C. for 6 hours and then at ambient temperature for 12 hours. The reaction mixture was kept for 24 hours at 4° C., which resulted in the formation of a crystalline precipitate and two liquid phases. The upper phase was collected and solvents were removed by evaporation at increased temperature (<60° C.), reduced pressure (<10 mbar) and condensation at 4° C. on the Rotavapor™, until the weight loss of the residue was less than 0.1 g per 30 min (Fraction-I). To a sample of Fraction-I, n-hexane and N-methylpyrrolidinone was added. The mixture was centrifuged for 10 min at 1000 g resulting in a transparent yellow upper phase (Fraction-II), a white opalescent interphase (Fraction-III) and a transparent lower phase. The solvents of Fraction-II and Fraction-III were removed by evaporation at increased temperature (<60° C.), reduced pressure (<10 mbar) and condensation at 4° C. on the Rotavapor™, until the weight loss of the residue was less than 0.1 g per 30 min.

The products obtained were analysed by TLC as described in Example 1.

Several formulations were prepared and their effects on the antibody response to CSFV-E2 were determined as described hereinabove in Example #1. Results are set forth in Table #2.2.

Formulations of 10 g of each fraction of the sucrose derivative (Fraction-I, Fraction-II and Fraction-III), with 10 g polysorbate 80 (ICI), 40 g squalane (Merck) and 190 g PBS-thimerosal were prepared as described above in Example #1. These formulations were tested in Group 3, 6 and 8, respectively.

A formulation of 10 g (sulphate)1-(dodecanoyl)-7-sucrose of Example #1 with 10 g polysorbate 80, 40 g squalane and 190 g PBS-thimerosal was prepared as described in Example #1. This formulation was tested in Group 2 and 5.

A formulation of 10 g (sulphate)1-(dodecanoyl)-7-sucrose of Table #1.1 with 10 g polysorbate 80, 10 g squalane and 220 g PBS-thimerosal was prepared as described in Example #1. This formulation was tested in Group 4.

A formulation of 10 g sucrose derivative (sulphate)1-(dodecanoyl)-7-sucrose of Table #1.1 with 10 g polysorbate 80 and 230 g PBS-thimerosal without squalane was prepared as described in Example #1. This formulation was tested in Group 7.

A formulation of 10 g polysorbate 80, 40 g squalane (Merck) and 200 g PBS-thimerosal was prepared as described above in Example #1. This formulation was tested in Group 9.

A water-in-mineral oil-in-water CSFV-E2 vaccine (ID-Lelystad, Lelystad, The Netherlands) was included in the experiment as a positive control. This formulation was tested in Group 10.

TABLE #2.2

| | Vaccine | | 2-log CSFV-neutralising antibody titre in serum 3 | | |
| --- | --- | --- | --- | --- | --- |
| | | Adjuvant | weeks post-boost | | |
| Group | Antigen | formulation | GMT | STDEV | antilog |
| 1 | CSFV-E2 | No adjuvant | 4.2 | 0.7 | 18 |
| 2 | CSFV-E2 | (sulphate)1-(dodecanoyl)7-sucrose (Example #1)/squalane/polysorbate 80 [40/160/40] | 11.1 | 0.4 | 2,228 |
| 3 | CSFV-E2 | (sulphate)1-(dodecanoyl)7-sucrose Fraction-I/squalane/polysorbate 80 [40/160/40] | 8.2 | 0.7 | 285 |
| 4 | CSFV-E2 | (sulphate)1-(dodecanoyl)7-sucrose (Example #1)/squalane/polysorbate 80 [40/40/40] | 10.7 | 0.9 | 1,689 |
| 5 | CSFV-E2 | (sulphate)1-(dodecanoyl)7-sucrose (Example #1)/squalane/polysorbate 80 [40/160/40] | ≥11.3 | 0.0 | ≥2,560 |
| 6 | CSFV-E2 | (sulphate)1-(dodecanoyl)7-sucrose Fraction-II/squalane/polysorbate 80 [40/160/40] | 8.4 | 0.9 | 347 |
| 7 | CSFV-E2 | (sulphate)1-(dodecanoyl)7-sucrose(Example #1)/polysorbate 80 [40/40] | 9.3 | 2.1 | 619 |
| 8 | CSFV-E2 | (sulphate)1-(dodecanoyl)7-sucrose Fraction-III/squalane/polysorbate 80 | ≥11.3 | 0.0 | ≥2,560 |
| 9 | CSFV-E2 | squalane/polysorbate 80 [160/40] | 8.3 | 1.3 | 309 |

TABLE #2.2-continued

| | Vaccine | | 2-log CSFV-neutralising antibody titre in serum 3 | | |
| --- | --- | --- | --- | --- | --- |
| | | Adjuvant | weeks post-boost | | |
| Group | Antigen | formulation | GMT | STDEV | antilog |
| 10 | CSFV-E2 | water-in-mineral oil-in-water emulsion | ≥11.3 | 0.0 | ≥2,560 |

The water-in-mineral oil-in-water emulsion was obtained from ID-Lelystad, Lelystad, The Netherlands.

In addition to antibody responses, effects of some of these adjuvants on cell-mediated immune responses were determined by a lymphocyte proliferation assay with peripheral blood mononuclear cells (PBMCs). Six days after the second immunisation, about 5 ml heparin blood was collected from each pig of Group 1, Group 2 and Group 10. The blood samples were diluted with 3 volumes of PBS and layered on 12 ml Ficoll-Paque (Pharmacia, Uppsala, Sweden) in 50-ml polypropylene tubes (Falcon). After centrifugation for 20 min at 1000 g, the interfaces containing the PBMCs were collected and cells were washed two times with PBS thereby centrifuging the suspensions for 10-15 min. at 1000 g. The number of living cells was determined by trypan blue exclusion method at 100× magnification and suspensions were adjusted to $5 \times 10^6$ cells per ml medium [RPMI 1640 medium (Flow 10-601-22) supplemented with 100 IE per ml penicillin, 0.1 mg per ml streptomycin, 4 µl beta-mercaptoethanol per L and 10% normal pig serum]. Of each suspension, 100 µl samples were put in six-fold into the wells of a flat bottom 96-well plate. Three replicates were supplemented with 50 ml RPMI medium (negatively controls) and three replicates were added with 50 µl of a solution of 7.1 µg CSFV-E2 per ml medium. Cells were incubated for 4 days at 37° C. in 5% $CO_2$ in a $CO_2$-incubator. After incubation, 25 µl medium containing 50 µCi methyl 3H-thymidine (Amersham TRA 120; 1 mCi per ml) per ml medium were added to each well. After incubation for 4 hours, DNA of the cells was collected on filters (Wallac) by using a cell harvester (Tomtec Harvester 96 match IIIM). Filters were dried at 70° C. and put in a filterbag (Wallac). Five ml scintillation fluid (Wallac betaplate stint; Wallac, Turku, Finland) was added and bags were sealed and radioactivity of each sample was determined in a beta-counter (Wallac beta-counter Model 1450 Microbeta PLUS, Wallac). Stimulation index of lymphocyte suspensions of individual animals was calculated by subtracting the mean number of counts per min (cpm) of the two or three replicates stimulated with the antigen by the mean number of counts per min of the two or three replicates incubated with medium only. The arithmetic mean stimulation index of animals of each group (AMT) and the standard deviation (STDEV) were calculated. Results are set forth in Table #2.3.

TABLE #2.3

| | Vaccine | | Stimulation index | |
| --- | --- | --- | --- | --- |
| | | Adjuvant | (cpm) | |
| Group | Antigen | formulation | AMT | STDEV |
| 1 | CSFV-E2 | No adjuvant | 1,993 | 448 |
| 2 | CSFV-E2 | (sulphate)1-(dodecanoyl)7-sucrose(Example #1)/squalane/polysorbate 80 [40/160/40] | 27,081 | 16,236 |
| 10 | CSFV-E2 | Water-in-mineral oil/polysorbate 80 | 2,384 | 1,174 |

Example #3

Various sucrose derivatives were synthesized as described in Example #1. Fine-powdered sucrose (Merck) was dried by heating for 6 h at 90° C. at <50 mbar and anhydrous N-methylpyrrolidinone (Merck) and anhydrous pyridine (Merck) were added. The mixture was stirred at 80° C. until a clear solution was obtained. Dodecanoylchloride (Merck), tetradecanoylchloride (Merck), hexadecanoylchloride (Merck) or octadecanoylchloride (Merck) was added and the reaction mixtures were incubated for 6 h at 60° C. $SO_3$.pyridine (Merck) was added and the reaction mixtures were incubated for 18 h at room temperature. The reaction mixtures were kept at 4° C. for 24 h, which caused the formation of two or three phases. The upper phases were collected and N-methylpyrrolidinone and pyridine were removed by evaporation at increased temperature (<60° C.), reduced pressure (<10 mbar) and condensation at 4° C., until the weight loss of the residue was less than 0.1 g per 30 min.

The quantities of the starting materials used are set forth in Table #3.1.

In addition, the antibody titres against CSFV were measured by enzyme-linked immunosorbent assay (ELISA). For this purpose, ELISA-plates were coated by dispensing into each well, 50 μl of carbonate buffer (pH 9.6) containing 2.5 μg immunoaffinity-chromatography purified CSFV-E2 per ml and subsequent incubation for 18 h at 4° C. or 2 h at 37° C. Plates were washed five times with 0.02% Tween 20 and blocked with 200 μl per well of 2% (w/v) skim milk (Difco) in phosphate buffered saline (PBS; pH 7.2; 0.05 M) and incubation for 1 h at 37° C. Serum samples were pre-diluted 10 or 100 fold in PBS containing 2% (w/v) skim milk (PBS/SM) and 50 μl of these pre-dilutions were serially diluted two-fold in PBS/SM in the ELISA-plates. Subsequently, plates were incubated for 1 h at 37° C. After five cycles of washing with 0.02% Tween 20, 50 μl of PBS/SM containing rabbit anti-swine Ig antiserum conjugated to peroxidase (Dako) diluted according to the supplier's instructions were added to the wells and the plates were incubated again for 1 h at 37° C. Plates were washed 10 times with 0.02% Tween 20 and 100 μl of a substrate solution containing 2,2'-azino-di-[3]-ethyl-benzthiazoline sulphonate (ABTS) plus H2O2

TABLE #3.1

| Sucrose derivative | Sucrose (g) | acoylchloride (g) | acoylchloride (type) | $SO_3$•Pyridine (g) | NMP (g) | Pyridine (g) | Molar ratios L/sucrose | Molar ratios S/sucrose |
|---|---|---|---|---|---|---|---|---|
| (dodecanoyl)7-sucrose | 6.8 | 30.7 | dodecanoyl chloride | 0.0 | 30 | 16 | 7.0 | 0.0 |
| (sulphate)0.5-(dodecanoyl)7-sucrose | 6.8 | 30.7 | dodecanoyl chloride | 1.6 | 30 | 16 | 7.0 | 0.5 |
| (sulphate)1-(dodecanoyl)7-sucrose | 6.8 | 34.6 | dodecanoyl chloride | 3.2 | 30 | 16 | 7.0 | 1.0 |
| (tetradecanoyl)7-sucrose | 6.8 | 34.6 | tetradecanoyl-chloride | 0.0 | 30 | 16 | 7.0 | 0.0 |
| (sulphate)0.5-(tetradecanoyl)7-sucrose | 6.8 | 34.6 | tetradecanoyl-chloride | 1.6 | 30 | 16 | 7.0 | 0.5 |
| (sulphate)1-(tetradecanoyl)7-sucrose | 6.8 | 34.6 | tetradecanoyl-chloride | 3.2 | 30 | 16 | 7.0 | 1.0 |
| (hexadecanoyl)7-sucrose | 6.8 | 38.5 | hexadecanoyl-chloride | 0.0 | 30 | 16 | 7.0 | 0.0 |
| (sulphate)0.5-(hexadecanoyl)7-sucrose | 6.8 | 38.5 | hexadecanoyl-chloride | 1.6 | 30 | 16 | 7.0 | 0.5 |
| (sulphate)1-(hexadecanoyl)7-sucrose | 6.8 | 38.5 | hexadecanoyl-chloride | 3.2 | 30 | 16 | 7.0 | 1.0 |
| (octadecanoyl)7-sucrose | 6.8 | 42.4 | octadecanoyl-chloride | 0.0 | 30 | 16 | 1.0 | 0.0 |
| (sulphate)0.5-(octadecanoyl)7-sucrose | 6.8 | 42.4 | octadecanoyl-chloride | 1.6 | 30 | 16 | 1.0 | 0.5 |
| (sulphate)1-(octadecanoyl)7-sucrose | 6.8 | 42.4 | octadecanoyl-chloride | 3.2 | 30 | 16 | 1.0 | 1.0 | molar ratio: L/Sucrose: mole acoylchloride per mole sucrose; S/sucrose: mole $SO_3$•pyridine per mole sucrose.

Some of the products obtained were analysed by TLC as described hereinabove in Example #1.

Formulations of the 10 g sucrose derivatives of Table #3.1 with 10 g polysorbate 80 (ICI), 40 g squalane (Merck) and 190 g PBS-thimerosal were prepared as described above in Example #1.

The effect of several of these formulations on immune responses against CSFV-E2 was determined in pigs as described hereinabove in Example #1. The antibody titres in serum against CSFV were measured by virus neutralisation assay as described hereinabove in Example #1. Results are set forth in Table #3.2.

(Kirkegaard & Perry Labs, Inc., Gaithersburg, Mass.) were added to the wells. Plates were incubated for 1 h at 20° C. and absorbance at 405 nm was measured by a Titertek Multiscan (ICN/Flow, Oxfordshire, United Kingdom). Antibody titres were expressed as the regression coefficient of the linear part of the plot of serum concentration versus absorbance value (linearity was significant between absorbance values of 0.0 and 1.4) which corresponds to the factor of dilution of the serum sample giving an optical density of 1 absorbance-unit above the background in the ELISA. Antibody titres 3 and 12 weeks after the booster immunisation are set forth in Table #3.3 and #3.4, respectively.

The effect of these formulations on cell-mediated immune response against CSFV-E2 was determined as described hereinabove in Example #2. Results are set forth in Table #3.5.

TABLE #3.2

| | Vaccine | | 2-log CSFV-neutralising antibody titre in serum 3 weeks post-boost | | |
|---|---|---|---|---|---|
| Group | Antigen | Adjuvant formulation | GMT | STDEV | antilog |
| 1 | CSFV-E2 | No adjuvant | 3.4 | 1.2 | 11 |
| 2 | CSFV-E2 | (tetradecanoyl)7-sucrose/squalane/polysorbate 80 [40/160/40] | 9.8 | 2.6 | 916 |
| 3 | CSFV-E2 | (sulphate)1-(dodecanoyl)7-sucrose/squalane/polysorbate 80 [40/160/40] | 14.9 | 0.5 | 31,042 |
| 4 | CSFV-E2 | (sulphate)1-(tetradecanoyl)7-sucrose/squalane/polysorbate 80 [40/160/40] | 13.3 | 2.8 | 10,240 |
| 5 | CSFV-E2 | (sulphate)1-(hexadecanoyl)7-sucrose/squalane/polysorbate 80 [40/160/40] | 10.0 | 2.1 | 993 |

TABLE #3.3

| | Vaccine | | 2-log anti-E2 ELISA antibody titre in serum 3 weeks post-boost | | |
|---|---|---|---|---|---|
| Group | Antigen | Adjuvant formulation | GMT | STDEV | antilog |
| 1 | CSFV-E2 | No adjuvant | 5.53 | 1.2 | 46 |
| 2 | CSFV-E2 | (tetradecanoyl)7-sucrose/squalane/polysorbate 80 [40/160/40] | 11.05 | 1.7 | 2,120 |
| 3 | CSFV-E2 | (sulphate)1-(dodecanoyl)7-sucrose/squalane/polysorbate 80 [40/160/40] | 13.78 | 1.2 | 14,067 |
| 4 | CSFV-E2 | (sulphate)1-(tetradecanoyl)7-sucrose/squalane/polysorbate 80 [40/160/40] | 13.05 | 2.1 | 11,585 |
| 5 | CSFV-E2 | (sulphate)1-(hexadecanoyl)7-sucrose/squalane/polysorbate 80 [40/160/40] | 11.24 | 1.2 | 2,419 |

TABLE #3.4

| | Vaccine | | 2-log anti-E2 ELISA antibody titre in serum 12 weeks post-boost | | |
|---|---|---|---|---|---|
| Group | Antigen | Adjuvant formulation | GMT | STDEV | antilog |
| 1 | CSFV-E2 | No adjuvant | 0.89 | 0.8 | 2 |
| 2 | CSFV-E2 | (tetradecanoyl)7-sucrose/squalane/polysorbate 80 [40/160/40] | 4.80 | 1.6 | 28 |
| 3 | CSFV-E2 | (sulphate)1-(dodecanoyl)7-sucrose/squalane/polysorbate 80 [40/160/40] | 7.69 | 1.8 | 207 |
| 4 | CSFV-E2 | (sulphate)1-(tetradecanoyl)7-sucrose/squalane/polysorbate 80 [40/160/40] | 6.51 | 2.0 | 91 |
| 5 | CSFV-E2 | (sulphate)1-(hexadecanoyl)7-sucrose/squalane/polysorbate 80 [40/160/40] | 4.94 | 1.0 | 31 |

TABLE #3.5

| | Vaccine | | Stimulation index 3 weeks after the first vaccination | | Stimulation index 3 weeks after the second vaccination | |
|---|---|---|---|---|---|---|
| Group | Antigen | Adjuvant formulation | AMT | STDEV | AMT | STDEV |
| 1 | CSFV-E2 | No adjuvant | 2,216 | 556 | 3,468 | 2,657 |
| 2 | CSFV-E2 | (tetradecanoyl)7-sucrose/squalane/polysorbate 80 [40/160/40] | 3,872 | 3,336 | 17,195 | 11,664 |
| 3 | CSFV-E2 | (sulphate)1-(dodecanoyl)7-sucrose/squalane/polysorbate 80 [40/160/40] | 8,306 | 5,943 | 22,018 | 28,194 |
| 4 | CSFV-E2 | (sulphate)1-(tetradecanoyl)7-sucrose/squalane/polysorbate 80 [40/160/40] | 4,629 | 5,939 | 10,693 | 9,707 |
| 5 | CSFV-E2 | (sulphate)1-(hexadecanoyl)7-sucrose/squalane/polysorbate 80 [40/160/40] | 3,100 | 4,400 | 15,413 | 22,485 |

The effect of several of these formulations on antibody responses in serum against inactivated influenza virus H1N1 strain A/Swine and H3N2 strain MRC-11 (hereinbelow designated as A/Swine and MRC-11, respectively) and inactivated pseudorabies virus (PRV) in pigs was determined. Animals were injected with 4.4 µg A/Swine, 4 µg MRC-11 and $10^{8.3}$ TCID50 (TCID50 is the dose causing 50% infection of tissue culture in vitro) inactivated PRV of Fort Dodge Animal Health Holland, Weesp, The Netherlands (Hilgers et al. Vaccine 1994) with or without adjuvant at Week 0 and 3. Three weeks after the first immunisation (Week 3) and three weeks after the second immunisation (Week 6), antibody responses against A/Swine and MRC-11 were measured by ELISA. For this purpose, ELISA-plates were coated with sucrose-gradient purified influenza virus by dispensing into each well, 50 µl of carbonate buffer (pH 9.6) containing 5 µg HA per ml and subsequent incubation for 18 h at 4° C. or 2 h at 37° C. Plates were washed five times with 0.02% Tween 20 and blocked with 200 µl per well of 2% (w/v) skim milk (Difco) in phosphate buffered saline (PBS; pH 7.2; 0.05 M) and incubation for 1 h at 37° C. Serum samples were pre-diluted 10 or 100 fold in PBS containing 2% (w/v) skim milk (PBS/SM) and 50 µl of these pre-dilutions were serially diluted two-fold in PBS/SM in the ELISA-plates. Subsequently, plates were incubated for 1 h at 37° C. After five cycles of washing with 0.02% Tween 20, 50 µl of PBS/SM containing mouse anti-swine total IgG monoclonal antibody conjugated to peroxidase (ID-Lelystad) diluted 1/2000 in PBS/SM were added to the wells and the plates were incubated again for 1 h at 37° C. Plates were washed 10 times with 0.02% Tween 20 and 100 µl of a substrate solution containing 2,2'-azino-di-[3-ethyl-benzthiazoline sulphonate (ABTS) plus H2O2 (Kirkegaard & Perry Labs, Inc., Gaithersburg, Mass.) were added to the wells. Plates were incubated for 60 min at 20° C. and absorbance at 405 nm was measured by a Titertek Multiscan (ICN/Flow, Oxfordshire, United Kingdom). Antibody titres were expressed as the regression coefficient of the linear part of the plot of serum concentration versus absorbance value (linearity was significant between absorbance values of 0.0 and 1.4) which corresponds to the factor of dilution of the serum sample giving an optical density of 1 absorbance-unit above the background in the ELISA. Antibody titres 3 after the first (priming) and second (booster) immunisation are set forth in Table #3.6 and #3.7, respectively.

At week 6, antibody responses against iPRV were measured by virus neutralisation assay as described by Hilgers et al. (Vaccine 12, pp. 653-660, 1994). Results are set forth in Table #3.8.

The effect of these formulations on cell-mediated immune response against influenza virus H1N1 strain A/Swine and H3N2 strain MRC-11 was determined in pigs as described hereinabove in Example #2. PBMCs were stimulated with A/Swine and MRC-11 at concentrations of 0.5 and 1.5 µg HA per ml cell culture medium. Results are set forth in Table #3.9 and #3.10, respectively.

TABLE #3.6

| | Vaccine | | 2-log A/Swine ELISA antibody titre in serum 3 weeks post-priming | | | 2-log A/Swine ELISA antibody titre in serum 3 weeks post-booster | | |
|---|---|---|---|---|---|---|---|---|
| Group | Antigen | Adjuvant formulation | GMT | STDEV | antilog | GMT | STDEV | antilog |
| 1 | A/Swine + MRC-11 | No adjuvant | 4.26 | 0.6 | 19 | 7.69 | 1.3 | 207 |
| 2 | A/Swine + MRC-11 | (sulphate)1-(dodecanoyl)7-sucrose/squalane/polysorbate 80 [40/160/40] | 9.14 | 1.4 | 564 | 12.03 | 1.5 | 4,182 |
| 3 | A/Swine + MRC-11 | Mineral oil-in-water emulsion (Suvaxyn; FDAHH) | 8.09 | 1.1 | 272 | 10.44 | 0.8 | 1,389 |

TABLE #3.7

| | Vaccine | | 2-log MRC-11 ELISA antibody titre in serum 3 weeks post-priming | | | 2-log MRC-11 ELISA antibody titre in serum 3 weeks post-boost | | |
|---|---|---|---|---|---|---|---|---|
| Group | Antigen | Adjuvant formulation | GMT | STDEV | antilog | GMT | STDEV | antilog |
| 1 | A/Swine + MRC-11 | No adjuvant | 6.97 | 0.9 | 125 | 10.30 | 1.1 | 1,260 |
| 2 | A/Swine + MRC-11 | (sulphate)1-(dodecanoyl)7-sucrose/squalane/polysorbate 80 [40/160/40] | 11.30 | 1.0 | 2,521 | 14.16 | 1.3 | 18,306 |
| 3 | A/Swine + MRC-11 | Mineral oil-in-water emulsion (Suvaxyn; FDAHH) | 10.55 | 0.8 | 1,499 | 12.93 | 1.1 | 7,806 |

TABLE #3.8

| | Vaccine | | 2-log anti-PRV neutralising antibody titre in serum 3 weeks post-boost | | |
|---|---|---|---|---|---|
| Group | Antigen | Adjuvant formulation | GMT | STDEV | antilog |
| 1 | A/Swine + MRC-11 | No adjuvant | 0.00 | 0.00 | 1 |
| 2 | A/Swine + MRC-11 | (sulphate)1-(dodecanoyl)7-sucrose/squalane/ | 5.03 | 1.4 | 33 |

TABLE #3.8-continued

| | Vaccine | | 2-log anti-PRV neutralising antibody titre in serum 3 weeks post-boost | | |
|---|---|---|---|---|---|
| Group | Antigen | Adjuvant formulation | GMT | STDEV | antilog |
| | | polysorbate 80 [40/160/40] | | | |
| 3 | A/Swine + MRC-11 | Mineral oil-in-water emulsion (Suvaxyn; FDAHH) | 4.07 | 2.0 | 17 |

TABLE #3.9

| | Vaccine | | Stimulation index 3 weeks after the first vaccination | | Stimulation index 3 weeks after the second vaccination | |
|---|---|---|---|---|---|---|
| Group | Antigen | Adjuvant formulation | AMT | STDEV | AMT | STDEV |
| 1 | A/Swine + MRC-11 | No adjuvant | 15,485 | 23,017 | 26,242 | 26,526 |
| 2 | A/Swine + MRC-11 | (sulphate)1-(dodecanoyl)7-sucrose/squalane/polysorbate 80 [40/160/40] | 8,287 | 7,940 | 35,467 | 13,637 |
| 3 | A/Swine + MRC-11 | Mineral oil-in-water emulsion (Suvaxyn; FDAHH) | 4,312 | 3,298 | 21,467 | 14,822 |

TABLE #3.10

| | Vaccine | | Stimulation index 3 weeks after the first vaccination | | Stimulation index 3 weeks after the second vaccination | |
|---|---|---|---|---|---|---|
| Group | Antigen | Adjuvant formulation | AMT | STDEV | AMT | STDEV |
| 1 | A/Swine + MRC-11 | No adjuvant | 12,186 | 15,108 | 27,571 | 27,320 |
| 2 | A/Swine + MRC-11 | (sulphate)1-(dodecanoyl)7-sucrose/squalane/polysorbate 80 [40/160/40] | 15,300 | 18,333 | 48,117 | 40,758 |
| 3 | A/Swine + MRC-11 | Mineral oil-in-water emulsion (Suvaxyn; FDAHH) | 4,527 | 3,287 | 19,882 | 18,894 |

Example #4

Various sucrose derivatives were synthesized as described in Example #3. The quantities of the starting materials used are set forth in Table #4.1.

TABLE #4.1

| Sucrose derivative | Sucrose | acoylchloride | | $SO_3$•Pyridine | NMP | Pyridine | Molar ratios | |
|---|---|---|---|---|---|---|---|---|
| # | (g) | (g) | type | (g) | (g) | (g) | L/sucrose | S/sucrose |
| (dodecanoyl)8-sucrose | 6.8 | 35.0 | dodecanoyl-chloride | 0.0 | 30 | 16 | 8.0 | 0 |
| (sulphate)0.5-(dodecanoyl)7-sucrose | 6.8 | 30.7 | dodecanoyl-chloride | 1.6 | 30 | 16 | 7.0 | 0.5 |
| (sulphate)1-(dodecanoyl)6-sucrose | 6.8 | 26.3 | dodecanoyl-chloride | 3.2 | 30 | 16 | 6.0 | 1.0 |

TABLE #4.1-continued

| Sucrose derivative # | Sucrose (g) | acoylchloride (g) | acoylchloride type | SO$_3$•Pyridine (g) | NMP (g) | Pyridine (g) | Molar ratios L/sucrose | Molar ratios S/sucrose |
|---|---|---|---|---|---|---|---|---|
| (sulphate)1.5-(dodecanoyl)5-sucrose | 6.8 | 21.9 | dodecanoyl-chloride | 4.8 | 30 | 16 | 5.0 | 1.5 |
| (sulphate)2-(dodecanoyl)4-sucrose | 6.8 | 17.5 | dodecanoyl-chloride | 6.4 | 30 | 16 | 4.0 | 2.0 |
| (sulphate)2.5-(dodecanoyl)3-sucrose | 6.8 | 13.1 | dodecanoyl-chloride | 8.0 | 30 | 16 | 3.0 | 2.5 |
| (sulphate)3-(dodecanoyl)2-sucrose | 6.8 | 8.8 | dodecanoyl-chloride | 9.4 | 30 | 16 | 2.0 | 3.0 |
| (sulphate)3.5-(dodecanoyl)1-sucrose | 6.8 | 4.4 | dodecanoyl-chloride | 11.0 | 30 | 16 | 1.0 | 3.5 |
| (sulphate)4-sucrose | 6.8 | 0.0 | dodecanoyl-chloride | 12.6 | 30 | 16 | 0.0 | 4.0 |

Molar ratio: L/Sucrose: mole dodecanoylchloride per mole sucrose; S/sucrose: mole SO$_3$•pyridine per mole sucrose.

The products obtained were analysed by TLC as described in Example #1.

Formulations of 10 g of the different sucrose derivatives of Table #4.1 with 10 g polysorbate 80 (ICI), 40 g squalane (Merck) and 190 PBS-thimerosal were prepared as described above in Example #1.

Example #5

Various sucrose derivatives were synthesized as described in Example #3 and quantities of the starting materials are set forth in Table #5.1.

TABLE #5.1

| Sucrose derivative # | Sucrose (g) | Dodecanoyl-chloride (g) | SO$_3$•Pyridine (g) | NMP (g) | Pyridine (g) | Molar ratios L/sucrose | Molar ratios S/sucrose |
|---|---|---|---|---|---|---|---|
| (dodecanoyl)8-sucrose | 6.8 | 35.0 | 0.0 | 30 | 16 | 8.0 | 0.0 |
| (sulphate)1-(dodecanoyl)7-sucrose | 6.8 | 30.7 | 3.2 | 30 | 16 | 7.0 | 1.0 |
| (sulphate)2-(dodecanoyl)6-sucrose | 6.8 | 26.3 | 6.4 | 30 | 16 | 6.0 | 2.0 |
| (sulphate)3-(dodecanoyl)5-sucrose | 6.8 | 21.9 | 9.5 | 30 | 16 | 5.0 | 3.0 |
| (sulphate)4-(dodecanoyl)4-sucrose | 6.8 | 17.5 | 12.7 | 30 | 16 | 4.0 | 4.0 |
| (sulphate)5-(dodecanoyl)3-sucrose | 6.8 | 13.1 | 15.9 | 30 | 16 | 3.0 | 5.0 |
| (sulphate)6-(dodecanoyl)2-sucrose | 6.8 | 8.8 | 19.1 | 30 | 16 | 2.0 | 6.0 |
| (sulphate)7-(dodecanoyl)1-sucrose | 6.8 | 4.4 | 22.3 | 30 | 16 | 1.0 | 7.0 |
| (sulphate)8-sucrose | 6.8 | 0.0 | 25.4 | 30 | 16 | 0.0 | 8.0 |

Molar ratio: L/Sucrose: mole dodecanoylchloride per mole sucrose; S/sucrose: mole SO$_3$•pyridine per mole sucrose.

The products obtained were analysed by TLC as described in Example #1.

Formulations of the 10 g sucrose derivatives of Table #5.1 with 10 g polysorbate 80 (ICI), 40 g squalane (Merck) and 190 g PBS-thimerosal were prepared as described above in Example #1.

The effect of (several of) these formulations on immune responses against CSFV-E2 was determined in pigs as described hereinabove in Example #1. Vaccines were prepared by simple mixing one volume of adjuvant formulation with one volume of antigen formulation. The antibody titres in serum against CSFV were measured by virus neutralisation assay as described hereinabove in Example #1. Results are set forth in Table #5.2.

Antibody titres were measured 3 and 12 weeks after the second immunisation (post-boost) by ELISA as described hereinabove in Example #3. Results are set forth in Table #5.3 and #5.4.

The cell-mediated response against CSFV was measured by the lymphocyte proliferation assay as described hereinabove in Example #2. Results are set forth in Table #5.5.

TABLE #5.2

| | Vaccine | | 2-log CSFV-neutralising antibody titre in serum 3 weeks post-boost | | |
|---|---|---|---|---|---|
| Group | Antigen | Adjuvant formulation | GMT | STDEV | antilog |
| 1 | CSFV-E2 | No adjuvant | 3.4 | 1.2 | 11 |
| 2 | CSFV-E2 | (sulphate)1-(dodecanoyl)7-sucrose/squalane/polysorbate 80 [40/160/40] | 14.9 | 0.5 | 31,042 |
| 3 | CSFV-E2 | (sulphate)2-(dodecanoyl)6-sucrose/squalane/polysorbate 80 [40/160/40] | 13.7 | 3.0 | 13,512 |
| 4 | CSFV-E2 | (sulphate)3-(dodecanoyl)5-sucrose/squalane/polysorbate 80 [40/160/40] | ≥15.3 | 0.0 | ≥40,960 |
| 5 | CSFV-E2 | (sulphate)4-(dodecanoyl)4-sucrose/squalane/polysorbate 80 [40/160/40] | 15.1 | 0.4 | 35,658 |
| 6 | CSFV-E2 | (sulphate)5-(dodecanoyl)3-sucrose/squalane/polysorbate 80 [40/160/40] | 14.2 | 1.4 | 19,335 |
| 7 | CSFV-E2 | (sulphate)6-(dodecanoyl)2-sucrose/squalane/polysorbate 80 [40/160/40] | 13.5 | 2.4 | 11,332 |

TABLE #5.3

| | Vaccine | | 2-log anti-E2 ELISA antibody titre in serum 3 weeks post-boost | | |
|---|---|---|---|---|---|
| Group | Antigen | Adjuvant formulation | GMT | STDEV | antilog |
| 1 | CSFV-E2 | No adjuvant | 5.53 | 1.2 | 46 |
| 2 | CSFV-E2 | (sulphate)1-(dodecanoyl)7-sucrose/squalane/polysorbate 80 [40/160/40] | 13.78 | 1.2 | 14,067 |
| 3 | CSFV-E2 | (sulphate)2-(dodecanoyl)6-sucrose/squalane/polysorbate 80 [40/160/40] | 12.96 | 1.9 | 7,968 |
| 4 | CSFV-E2 | (sulphate)3-(dodecanoyl)5-sucrose/squalane/polysorbate 80 [40/160/40] | 13.50 | 0.7 | 11,585 |
| 5 | CSFV-E2 | (sulphate)4-(dodecanoyl)4-sucrose/squalane/polysorbate 80 [40/160/40] | 15.02 | 0.4 | 33,225 |
| 6 | CSFV-E2 | (sulphate)5-(dodecanoyl)3-sucrose/squalane/polysorbate 80 [40/160/40] | 14.76 | 0.7 | 27,746 |
| 7 | CSFV-E2 | (sulphate)6-(dodecanoyl)2-sucrose/squalane/polysorbate 80 [40/160/40] | 14.39 | 1.1 | 21,469 |

TABLE #5.4

| | Vaccine | | 2-log anti-E2 ELISA antibody titre in serum 12 weeks post-boost | | |
|---|---|---|---|---|---|
| Group | Antigen | Adjuvant formulation | GMT | STDEV | antilog |
| 1 | CSFV-E2 | No adjuvant | 0.89 | 0.8 | 2 |
| 2 | CSFV-E2 | (sulphate)1-(dodecanoyl)7-sucrose/squalane/polysorbate 80 [40/160/40] | 7.69 | 1.8 | 207 |
| 3 | CSFV-E2 | (sulphate)2-(dodecanoyl)6-sucrose/squalane/polysorbate 80 [40/160/40] | 5.99 | 1.7 | 64 |
| 4 | CSFV-E2 | (sulphate)3-(dodecanoyl)5-sucrose/squalane/polysorbate 80 [40/160/40] | 5.95 | 1.5 | 62 |
| 5 | CSFV-E2 | (sulphate)4-(dodecanoyl)4-sucrose/squalane/polysorbate 80 [40/160/40] | 8.70 | 1.5 | 416 |
| 6 | CSFV-E2 | (sulphate)5-(dodecanoyl)3-sucrose/squalane/polysorbate 80 [40/160/40] | 8.73 | 0.7 | 425 |
| 7 | CSFV-E2 | (sulphate)6-(dodecanoyl)2-sucrose/squalane/polysorbate 80 [40/160/40] | 8.26 | 1.3 | 307 |

TABLE #5.5

| Group | Antigen | Vaccine Adjuvant formulation | Stimulation index 3 weeks after the first vaccination AMT | STDEV | Stimulation index 3 weeks after the second vaccination AMT | STDEV |
|---|---|---|---|---|---|---|
| 1 | CSFV-E2 | No adjuvant | 2,216 | 556 | 3,468 | 2,657

TABLE #6.1-continued

| Sucrose derivative | disaccharide (g) type | Dodecanoylchloride (g) | SO₃•Pyridine (g) | NMP (g) | Pyridine (g) | Molar ratios L/sugar | S/sugar |
|---|---|---|---|---|---|---|---|
| (dodecanoyl)7-lactose | 7.3 lactose | 30.7 | 0.0 | 30 | 16 | 8.0 | 0.0 |
| (sulphate)0.5-(dodecanoyl)7-lactose | 7.3 lactose | 30.7 | 1.6 | 30 | 16 | 8.0 | 0.5 |
| (sulphate)1-(dodecanoyl)7-lactose | 7.3 lactose | 30.7 | 3.2 | 30 | 16 | 8.0 | 1.0 |

Molar ratio: L/sugar: mole dodecanoylchloride per mole disaccharide; S/sugar: mole SO₃•pyridine per mole disaccharide.
Maltose = maltose monohydrate (Merck) and lactose = alpha-lactose monohydrate (Acros).

The products obtained were analysed by TLC as described in Example #1.

Formulations of the different sucrose derivatives of Table #6.1 with polysorbate 80 (ICI), squalane (Merck) and (PBS-thimerosal were prepared as described hereinabove in Example #1.

The effect of (several of) these formulations on immune responses against CSFV-E2 was determined in pigs as described hereinabove in Example #1. Vaccines were prepared by simple mixing one volume of adjuvant formulation with one volume of antigen formulation. The antibody titres in serum against CSFV were measured by virus neutralisation assay as described hereinabove in Example #1. Results are set forth in Table #6.2.

Antibody titres were measured 3 and 12 weeks after the second immunisation (post-boost) by ELISA as described hereinabove in Example #3. Results are set forth in Table #6.3 and #6.4.

The cell-mediated response against CSFV was measured by the lymphocyte proliferation assay as described hereinabove in Example #2. Results are set forth in Table #6.5.

TABLE #6.2

| Vaccine | | 2-log CSFV-neutralising antibody titre in serum 3 weeks post-boost | | |
|---|---|---|---|---|
| Group | Antigen | Adjuvant formulation | GMT | STDEV | antilog |
| 1 | CFSV-E2 | No adjuvant | 3.4 | 1.2 | 11 |
| 2 | CFSV-E2 | (sulphate)1-(dodecanoyl)7-sucrose/squalane/polysorbate 80 [40/160/40] | 14.9 | 0.5 | 31,042 |
| 3 | CFSV-E2 | (sulphate)1-(dodecanoyl)7-maltose/squalane/polysorbate 80 [40/160/40] | 13.2 | 1.7 | 9,176 |
| 4 | CFSV-E2 | (sulphate)1-(dodecanoyl)7-lactose-IV/squalane/polysorbate 80 [40/160/40] | ≥15.3 | 0.0 | ≥40,960 |

TABLE #6.3

| Vaccine | | 2-log anti-E2 ELISA antibody titre in serum 3 weeks post-boost | | |
|---|---|---|---|---|
| Group | Antigen | Adjuvant formulation | GMT | STDEV | antilog |
| 1 | CFSV-E2 | No adjuvant | 5.53 | 1.2 | 46 |
| 2 | CFSV-E2 | (sulphate)1-(dodecanoyl)7-sucrose/squalane/polysorbate 80 [40/160/40] | 13.78 | 1.2 | 14,067 |
| 3 | CFSV-E2 | (sulphate)1-(dodecanoyl)7-maltose/squalane/polysorbate 80 [40/160/40] | 13.08 | 1.0 | 8,659 |
| 4 | CFSV-E2 | (sulphate)1-(dodecanoyl)7-lactose-IV/squalane/polysorbate 80 [40/160/40] | 14.88 | 0.8 | 30,153 |

TABLE #6.4

| Vaccine | | 2-log anti-E2 ELISA antibody titre in serum 12 weeks post-boost | | |
|---|---|---|---|---|
| Group | Antigen | Adjuvant formulation | GMT | STDEV | antilog |
| 1 | CFSV-E2 | No adjuvant | 0.89 | 0.8 | 2 |
| 2 | CFSV-E2 | (sulphate)1-(dodecanoyl)7-sucrose/squalane/polysorbate 80 [40/160/40] | 7.69 | 1.8 | 207 |
| 3 | CFSV-E2 | (sulphate)1-(dodecanoyl)7-maltose/squalane/polysorbate 80 [40/160/40] | 6.96 | 1.1 | 124 |
| 4 | CFSV-E2 | (sulphate)1-(dodecanoyl)7-lactose-IV/squalane/polysorbate 80 [40/160/40] | 8.48 | 1.1 | 357 |

TABLE #6.5

| Group | Antigen | Vaccine Adjuvant formulation | Stimulation index 3 weeks after the first vaccination GMT | STDEV | Stimulation index 3 weeks after the second vaccination GMT | STDEV |
|---|---|---|---|---|---|---|
| 1 | CSFV-E2 | No adjuvant | 2,216 | 556 | 3,468 | 2,657 |
| 2 | CSFV-E2 | (sulphate)1-(dodecanoyl)7-sucrose/squalane/polysorbate 80 [40/160/40] | 8,306 | 5,943 | 22,018 | 28,194 |
| 3 | CSFV-E2 | (sulphate)1-(dodecanoyl)7-maltose/squalane/polysorbate 80 [40/160/40] | 2,602 | 1,508 | 18,130 | 12,111 |
| 4 | CSFV-E2 | (sulphate)1-(dodecanoyl)7-lactose-IV/squalane/polysorbate 80 [40/160/40] | 6,415 | 7,392 | 27,595 | 24,289 |

The effect of various of these formulations on antibody responses in serum against inactivated influenza virus H1N1 strain A/Swine and H3N2 strain MRC-11 in pigs was determined by ELISA as described hereinabove in Example #3. Results are set forth in Table #6.5 and #6.6.

TABLE #6.5

| Group | Antigen | Vaccine Adjuvant formulation | 2-log A/Swine ELISA-antibody titre in serum 3 weeks post-boost GMT | STDEV | antilog |
|---|---|---|---|---|---|
| 1 | A/Swine + MRC-11 | No adjuvant | 7.69 | 1.3 | 207 |
| 2 | A/Swine + MRC-11 | (sulphate)1-(dodecanoyl)7-sucrose/squalane/polysorbate 80 [40/160/40] | 12.02 | 0.8 | 4,153 |
| 3 | A/Swine + MRC-11 | (sulphate)1-(dodecanoyl)7-maltose/squalane/polysorbate 80 [40/160/40] | 10.80 | 1.0 | 1,783 |
| 4 | A/Swine + MRC-11 | (sulphate)1-(dodecanoyl)7-lactose-IV/squalane/polysorbate 80 [40/160/40] | 11.34 | 1.1 | 2,592 |

TABLE #6.6

| Group | Antigen | Vaccine Adjuvant formulation | 2-log MRC-11 ELISA-antibody titre in serum 3 weeks post-boost GMT | STDEV | antilog |
|---|---|---|---|---|---|
| 1 | A/Swine + MRC-11 | No adjuvant | 10.30 | 1.1 | 1,261 |
| 2 | A/Swine + MRC-11 | (sulphate)1-(dodecanoyl)7-sucrose/squalane/polysorbate 80 [40/160/40] | 13.88 | 1.2 | 15,076 |
| 3 | A/Swine + MRC-11 | (sulphate)1-(dodecanoyl)7-maltose/squalane/polysorbate 80 [40/160/40] | 12.93 | 0.9 | 7,804 |
| 4 | A/Swine + MRC-11 | (sulphate)1-(dodecanoyl)7-lactose-IV/squalane/polysorbate 80 [40/160/40] | 13.29 | 1.2 | 10,016 |

Example #7

Various disaccharide derivatives were synthesized by contacting sucrose fatty acid ester L195 (Mitsubishi-Kagaku Foods Corp., Tokyo, Japan) with $SO_3$·pyridine for about 6 hours at 60° C. The quantities of the starting materials are set forth in Table #7.1.

TABLE #7.1

| Sucrose derivative | Sucrose fatty acid ester L195 (g) | $SO_3$·Pyridine (g) | NMP (g) | Pyridine (g) | Molar ratios L/sugar* | S/sugar |
|---|---|---|---|---|---|---|
| L195 | 27.8 | 0 | 20 | 0 | 5.7 | 0.0 |
| (sulphate)1-L195 | 27.8 | 3.2 | 20 | 0 | 5.7 | 1.0 |
| (sulphate)2-L195 | 27.8 | 6.4 | 20 | 0 | 5.7 | 2.0 |
| (sulphate)2.3-L195 | 27.8 | 7.3 | 20 | 0 | 5.7 | 2.3 | molar ratio: L/sugar = mole dodecanoylchloride per mole L195; S/sugar = mole $SO_3$·pyridine per mole L195.
*According to the supplier of L195.

The products obtained were analysed by TLC as described in Example #1.

Formulations of 10 g of the sucrose derivatives of Table #7.1, 10 g polysorbate 80 (ICI), 40 g squalane (Merck) and 190 g PBS-thimerosal were prepared as described above in Example #1.

The effect of (several of) these formulations on immune responses against CSFV-E2 was determined in pigs as described hereinabove in Example #1. Vaccines were prepared by simple mixing one volume of adjuvant formulation with one volume of antigen formulation. The antibody titres in serum against CSFV were measured by virus neutralisation assay as described hereinabove in Example #1. Results are set forth in Table #7.2.

Antibody titres were measured 3 and 12 weeks after the second immunisation (post-boost) by ELISA as described hereinabove in Example #3. Results are set forth in Table #7.3 and #7.4.

The cell-mediated response against CSFV was measured by the lymphocyte proliferation assay as described hereinabove in Example #2. Results are set forth in Table #7.5.

TABLE #7.2

| Group | Vaccine Antigen | Adjuvant formulation | 2log CSFV neutralising antibody titre 3 weeks after the second vaccination | | |
|---|---|---|---|---|---|
| | | | GMT | STDEV | antilog |
| 1 | CSFV-E2 | No adjuvant | 3.4 | 1.2 | 11 |
| 2 | CSFV-E2 | L195/squalane/polysorbate 80 [40/160/40] | | | |
| 3 | CSFV-E2 | (sulphate)1-L195/squalane/polysorbate 80 [40/160/40] | 14.5 | 1.1 | 23,525 |
| 4 | CSFV-E2 | (sulphate)2-L195/squalane/polysorbate 80 [40/160/40] | 13.8 | 1.3 | 13,834 |
| 5 | CSFV-E2 | (sulphate)2.3-L195/squalane/polysorbate 80 [40/160/40] | 14.6 | 0.9 | 25,631 |

TABLE #7.3

| Group | Vaccine Antigen | Adjuvant formulation | 2log anti-E2 ELISA antibody titre 3 weeks after the second vaccination | | |
|---|---|---|---|---|---|
| | | | GMT | STDEV | antilog |
| 1 | CSFV-E2 | No adjuvant | 5.53 | 1.2 | 46 |
| 2 | CSFV-E2 | L195/squalane/polysorbate 80 [40/160/40] | 12.20 | 1.2 | 4,705 |
| 3 | CSFV-E2 | (sulphate)1-L195/squalane/polysorbate 80 [40/160/40] | 13.79 | 1.4 | 14,165 |
| 4 | CSFV-E2 | (sulphate)2-L195/squalane/polysorbate 80 [40/160/40] | 14.18 | 1.6 | 18,561 |
| 5 | CSFV-E2 | (sulphate)2.3-L195/squalane/polysorbate 80 [40/160/40] | 14.22 | 1.0 | 19,083 |

TABLE #7.4

| Group | Vaccine Antigen | Adjuvant formulation | 2-log anti-E2 ELISA antibody titre 12 weeks after the second vaccination | | |
|---|---|---|---|---|---|
| | | | GMT | STDEV | antilog |
| 1 | CSFV-E2 | No adjuvant | 0.89 | 0.8 | 2 |
| 2 | CSFV-E2 | L195/squalane/polysorbate 80 [40/160/40] | 5.89 | 0.6 | 59 |
| 3 | CSFV-E2 | (sulphate)1-L195/squalane/polysorbate 80 [40/160/40] | 7.13 | 0.9 | 140 |
| 4 | CSFV-E2 | (sulphate)2-L195/squalane/polysorbate 80 [40/160/40] | 7.37 | 1.7 | 165 |
| 5 | CSFV-E2 | (sulphate)2.3-L195/squalane/polysorbate 80 [40/160/40] | 8.41 | 1.0 | 340 |

TABLE #7.5

| Group | Vaccine Antigen | Adjuvant formulation | Stimulation index 3 weeks after the first vaccination | | Stimulation index 3 weeks after the second vaccination | |
|---|---|---|---|---|---|---|
| | | | AMT | STDEV | AMT | STDEV |
| 1 | CSFV-E2 | No adjuvant | 2,216 | 556 | 3,468 | 2,657 |
| 2 | CSFV-E2 | L195/squalane/polysorbate 80 [40/160/40] | 7,157 | 8,943 | 18,807 | 20,879 |
| 3 | CSFV-E2 | (sulphate)1-L195/squalane/polysorbate 80 [40/160/40] | 3,104 | 2,062 | 18,710 | 26,432 |
| 4 | CSFV-E2 | (sulphate)2-L195/squalane/polysorbate 80 [40/160/40] | 8,310 | 9,680 | 29,835 | 36,351 |
| 5 | CSFV-E2 | (sulphate)2.3-L195/squalane/polysorbate 80 [40/160/40] | 513 | 932 | 6,515 | 5,337 |

The effect of various of these formulations on antibody responses in serum against inactivated influenza virus H1N1 strain A/Swine and H3N2 strain MRC-11 in pigs was determined by ELISA as described hereinabove in Example #3. Results are set forth in Table #7.6 and #7.7

TABLE #7.6

| Group | Vaccine Antigen | Adjuvant formulation | 2log anti-A/Swine ELISA antibody titre 3 weeks after the second vaccination | | |
|---|---|---|---|---|---|
| | | | GMT | STDEV | antilog |
| 1 | A/Swine + MRC-11 | No adjuvant | 7.69 | 1.3 | 207 |
| 2 | A/Swine + MRC-11 | L195/squalane/polysorbate 80 [40/160/40] | 12.76 | 1.3 | 6,937 |
| 3 | A/Swine + MRC-11 | (sulphate)1-L195/squalane/polysorbate 80 [40/160/40] | 12.78 | 1.0 | 7,033 |
| 4 | A/Swine + MRC-11 | (sulphate)2-L195/squalane/polysorbate 80 [40/160/40] | 12.69 | 0.5 | 6,608 |
| 5 | A/Swine + MRC-11 | (sulphate)2.3-L195/squalane/polysorbate 80 [40/160/40] | 12.47 | 1.1 | 5,673 |

TABLE #7.7

| Group | Vaccine Antigen | Adjuvant formulation | 2log anti-MRC-11 ELISA antibody titre 3 weeks after the second vaccination | | |
|---|---|---|---|---|---|
| | | | GMT | STDEV | antilog |
| 1 | A/Swine + MRC-11 | No adjuvant | 10.30 | 1.1 | 1,261 |
| 2 | A/Swine + MRC-11 | L195/squalane/polysorbate 80 [40/160/40] | 14.76 | 1.4 | 27,746 |
| 3 | A/Swine + MRC-11 | (sulphate)1-L195/squalane/polysorbate 80 [40/160/40] | 14.54 | 1.4 | 23,822 |
| 4 | A/Swine + MRC-11 | (sulphate)2-L195/squalane/polysorbate 80 [40/160/40] | 14.39 | 0.7 | 21,469 |
| 5 | A/Swine + MRC-11 | (sulphate)2.3-L195/squalane/polysorbate 80 [40/160/40] | 14.59 | 0.7 | 24,662 |

Example #8

A formulation of 40 g L195 (Mitshubishi-Kagaku Foods Corp., Tokyo, Japan), 10 g polysorbate 80 (ICI) and 200 g PBS-thimerosal was prepared as described above in Example #1.

A formulation of 10 g (sulphate)1-(dodecanoyl)-7-sucrose of Example #5 with 10 g polysorbate 80 (ICI), 40 g L195 (Merck) and 190 g PBS-thimerosal as prepared as described hereinabove in Example #1.

The effect of (several of) these formulations on immune responses against CSFV-E2 was determined in pigs as described hereinabove in Example #1. Vaccines were prepared by simple mixing one volume of adjuvant formulation with one volume of antigen formulation. The antibody titres in serum against CSFV were measured by virus neutralisation assay as described hereinabove in Example #1. Results are set forth in Table #8.2.

Antibody titres were measured 3 and 12 weeks after the second immunisation (post-boost) by ELISA as described hereinabove in Example #3. Results are set forth in Table #8.3 and #8.4.

The cell-mediated response against CSFV was measured by the lymphocyte proliferation assay as described hereinabove in Example #2. Results are set forth in Table #8.5.

TABLE #8.2

| Group | Vaccine Antigen | Adjuvant | 2log CSFV neutralising antibody titre 3 weeks after the second vaccination | | |
|---|---|---|---|---|---|
| | | | GMT | STDEV | antilog |
| 1 | CSFV-E2 | No adjuvant | 3.4 | 1.2 | 11 |
| 2 | CSFV-E2 | L195/polysorbate 80 [160/40] | 8.7 | 1.5 | 403 |
| 3 | CSFV-E2 | (sulphate)1-(dodecanoyl)7-sucrose/L195 (Example #5)/polysorbate 80 [40/160/40] | 11.0 | 3.3 | 2,104 |

TABLE #8.3

| Group | Vaccine Antigen | Adjuvant | 2log anti-E2 ELISA antibody titre 3 weeks after the second vaccination | | |
|---|---|---|---|---|---|
| | | | GMT | STDEV | antilog |
| 1 | CSFV-E2 | No adjuvant | 5.53 | 1.2 | 46 |
| 2 | CSFV-E2 | L195/polysorbate 80 [160/40] | 10.32 | 1.0 | 1,278 |
| 3 | CSFV-E2 | (sulphate)1-(dodecanoyl)7-sucrose (Example #5)/L195/polysorbate 80 [40/160/40] | 15.21 | 0.7 | 37,902 |

TABLE #8.4

| Group | Vaccine Antigen | Adjuvant | 2log anti-E2 ELISA antibody titre 12 weeks after the second vaccination | | |
|---|---|---|---|---|---|
| | | | GMT | STDEV | antilog |
| 1 | CSFV-E2 | No adjuvant | 0.89 | 0.8 | 2 |
| 2 | CSFV-E2 | L195/polysorbate 80 [160/40] | 4.84 | 0.9 | 29 |
| 3 | CSFV-E2 | (sulphate)1-(dodecanoyl)7-sucrose (Example #5)/L195/polysorbate 80 [40/160/40] | 8.41 | 1.0 | 340 |

TABLE #8.5

| Group | Vaccine Antigen | Adjuvant | Stimulation index 3 weeks after the first vaccination | | Stimulation index 3 weeks after the second vaccination | |
|---|---|---|---|---|---|---|
| | | | AMT | STDEV | AMT | STDEV |
| 1 | CSFV-E2 | No adjuvant | 2,216 | 556 | 3,468 | 2,657 |
| 2 | CSFV-E2 | L195/polysorbate 80 | 8,306 | 5,943 | 22,018 | 28,194 |
| 3 | CSFV-E2 | (sulphate)1-(dodecanoyl)7-sucrose (Example #5)//L195/polysorbate 80 | 3,801 | 4,775 | 4,605 | 2,490 |

Example #9

A (oleoyl)8-sucrose was synthesized by contacting 0.02 mole of sucrose with 0.15 mole of oleoylchloride (Merck) for about 6 hours at 60° C. The sucrose derivative was extracted with n-hexane. N-hexane was removed by evaporation at increased temperature and decreased pressure as described hereinabove in Example #2. The products obtained were analysed by TLC as described in Example #1.

Three different emulsions of the sucrose octaoleate ester were prepared. (oleoyl)-8-sucrose, squalane, polysorbate 80 and PBS-thimerosal were mixed at quantities indicated in Table #9.1 and emulsified as described hereinabove in Example #1. In addition, an emulsion of squalane/polysorbate 80 without sucrose octaoleate was prepared by mixing the quantities squalane, polysorbate 80 and PBS-thimerosal as indicated in Table #9.1.

TABLE #9.1

| Emulsion | (oleoyl)8-sucrose (g) | Squalane (g) | Polysorbate 80 (g) | PBS-thimerosal (g) |
|---|---|---|---|---|
| squalane/polysorbate 80 [160/40] | 0 | 40 | 10 | 200 |
| (oleoyl)8-sucrose/polysorbate 80 [160/40] | 40 | 0 | 10 | 200 |
| (oleoyl)8-sucrose/squalane/polysorbate 80 [40/160/40] | 10 | 40 | 10 | 190 |
| (oleoyl)8-sucrose/squalane/polysorbate 80 [80/160/40] | 20 | 20 | 10 | 200 |

The effect of the emulsions of Table #9.1 on the virus neutralising antibody response against CSFV-E2 was determined as described in Example #1. SL-CD/squalane-in-water (Fort Dodge Animal Health Holland, The Netherlands) was included as a reference. Results are set forth in Table #9.2.

TABLE #9.2

| | | | 2-log CSFV-neutralising antibody titre in serum 3 weeks post-boost | | |
|---|---|---|---|---|---|
| Group | Antigen | Adjuvant | GMT | STDEV | antilog |
| 1 | CSFV-E2 | No adjuvant | 3.64 | 0.00 | 13 |
| 2 | CSFV-E2 | squalane/polysorbate 80 [160/40] | 5.36 | 1.48 | 41 |
| 3 | CSFV-E2 | (oleoyl)8-sucrose/polysorbate 80 [160/40] | 4.88 | 1.14 | 29 |
| 4 | CSFV-E2 | (oleoyl)8-sucrose/squalane/polysorbate 80 [40/160/40] | 6.27 | 1.05 | 77 |
| 5 | CSFV-E2 | (oleoyl)8-sucrose/squalane/polysorbate 80 [80/160/40] | 5.68 | 2.00 | 51 |
| 6 | CSFV-E2 | SL-CD/squalane-in-water (Fort Dodge Animal Health) | 10.44 | 0.45 | 1,393 |

The preparation of the different adjuvants is indicated in Table #9.1. The dose of CSFV-E2 was 32 μg per animal.

Example #10

A commercially available pseudorabies/influenza virus vaccine (Suvaxyn O/W of Fort Dodge Animal Health Holland, Weesp, The Netherlands) containing inactivated influenza virus strains MRC-11 and A/Swine at 4.0 and 4.4 μg HA per dose and inactivated pseudorabies virus at $10^{8.3}$ $TCID_{50}$ per dose was mixed with the adjuvant formulation (sulphate)-(dodecanoyl)-7-sucrose/squalane/polysorbate 80 of Example #1 at volume ratios 100/0, 33/66, 20/80 and 10/90. Groups of pigs were immunised twice and antibody responses against pseudorabies virus by virus neutralising antibody assay as Hilgers et al. (Vaccine 12, pp 653-660, 1994). Results are set forth in Table #10.1. Antibody responses against influenza virus strains A/Swine and MRC-11 were measured by EILSA as described in Examples #3. Results are set forth in Table #10.2 and #10.3, respectively.

TABLE #10.1

| | Vaccine composition (volume %) | | 2-log PRV neutralising antibody titre in serum 3 weeks post-boost | | |
|---|---|---|---|---|---|
| Group | Suvaxyn O/W | (sulphate)1-(dodecanoyl)7-sucrose/squalane/polysorbate 80 [40/160/40] | GMT | STDEV | antilog |
| 1 | 100 | 0 | 4.07 | 2.0 | 17 |
| 2 | 33 | 66 | 5.54 | 1.8 | 47 |
| 3 | 20 | 80 | 1.95 | 2.1 | 4 |
| 4 | 10 | 90 | 0.80 | 1.1 | 1 |

TABLE #10.2

| | Vaccine composition (volume %) | | 2-log A/Swine ELISA antibody titre in serum 3 weeks post-boost | | |
|---|---|---|---|---|---|
| Group | Suvaxyn O/W | (sulphate)1-(dodecanoyl)7-sucrose/squalane/polysorbate 80 [40/160/40] | GMT | STDEV | antilog |
| 1 | 100 | 0 | 10.44 | 0.8 | 1,389 |
| 2 | 33 | 66 | 12.44 | 0.7 | 5,557 |
| 3 | 20 | 80 | 11.43 | 1.2 | 2,759 |
| 4 | 10 | 90 | 11.51 | 1.1 | 2,916 |

TABLE #10.3

| | Vaccine composition (volume ratio in %) | | 2-log MRC-11 ELISA antibody titre in serum 3 weeks post-boost | | |
|---|---|---|---|---|---|
| Group | Suvaxyn O/W | (sulphate)1-(dodecanoyl)7-sucrose/squalane/polysorbate 80 [40/160/40] | GMT | STDEV | antilog |
| 1 | 100 | 0 | 12.93 | 1.1 | 7,804 |
| 2 | 33 | 66 | 15.01 | 0.8 | 32,996 |
| 3 | 20 | 80 | 14.73 | 0.8 | 27,175 |
| 4 | 10 | 90 | 14.74 | 1.2 | 27,364 |

Example #11

A sucrose derivative was synthesized as described in Example #1. The quantities of the starting materials used are set forth in Table #11.1

TABLE #11.1

| Sucrose derivative | Sucrose (g) | acoylchloride (g) | acoylchloride (type) | SO$_3$•Pyridine (g) | NMP (g) | Pyridine (g) | Molar ratios L/sucrose | Molar ratios S/sucrose |
|---|---|---|---|---|---|---|---|---|
| (sulphate)1-(dodecanoyl)7-sucrose | 17.1 | 76.7 | dodecanoyl-chloride | 8 | 74 | 40 | 7.0 | 1.0 |

Molar ratio: L/Sucrose: mole acoylchloride per mole sucrose; S/sucrose: mole SO$_3$•pyridine per mole sucrose.

The products obtained were analysed by TLC as described in Example #1.

Formulations of the sucrose derivatives of Table #10.1 with polysorbate 80 (ICI), squalane (Merck) and PBS-thimerosal were prepared as described hereinabove in Example #1.

The effect of (several of) these formulations on immune responses against CSFV-E2 was determined in pigs as described hereinabove in Example #1. Vaccines were prepared by simple mixing one volume of adjuvant formulation with one volume of antigen formulation. The antibody titres in serum against CSFV were measured by virus neutralisation assay as described hereinabove in Example #1. Results are set forth in Table #11.2.

Antibody titres were measured by ELISA as described hereinabove in Example #3. Results are set forth in Table #11.3.

The cell-mediated response against CSFV was measured by the lymphocyte proliferation assay as described hereinabove in Example #2. Results are set forth in Table #11.4.

TABLE #11.2

| | Vaccine | | 2-log CSFV neutralising antibody titre in serum 3 week post-boost | | |
|---|---|---|---|---|---|
| Group | Antigen | Adjuvant formulation | GMT | STDEV | antilog |
| 1 | CSFV-E2 | No adjuvant | 3.7 | 0.3 | 13 |
| 3 | CSFV-E2 | (sulphate)1-(dodecanoyl)7-sucrose/polysorbate 80 [40/40] | 7.4 | 3.0 | 675 |
| 4 | CSFV-E2 | squalane/polysorbate 80 [160/40] | 5.8 | 1.7 | 89 |
| 5 | CSFV-E2 | (sulphate)1-(dodecanoyl)7-sucrose/squalane/polysorbate 80 [40/160/40] | 12.0 | 1.8 | 7,424 |
| 6 | CSFV-E2 | (sulphate)1-(dodecanoyl)7-sucrose/squalane/polysorbate 80 [40/160/40] injected separately from the antigen | 10.2 | 3.0 | 3,787 |

TABLE #11.3

| | Vaccine | | 2-log anti-E2 ELISA antibody titre in serum 3 week post-boost | | |
|---|---|---|---|---|---|
| Group | Antigen | Adjuvant formulation | GMT | STDEV | antilog |
| 1 | CSFV-E2 | No adjuvant | 2.5 | 0.7 | 6 |
| 2 | CSFV-E2 | (sulphate)1-(dodecanoyl)7-sucrose/polysorbate 80 [40/40] | 6.3 | 1.8 | 80 |
| 3 | CSFV-E2 | squalane/polysorbate 80 [160/40] | 3.1 | 2.4 | 8.7 |
| 4 | CSFV-E2 | (sulphate)1-(dodecanoyl)7-sucrose/squalane/polysorbate 80 [40/160/40] | 9.1 | 1.4 | 555 |
| 5 | CSFV-E2 | (sulphate)1-(dodecanoyl)7-sucrose/squalane/polysorbate 80 | 7.9 | 0.9 | 241 |

TABLE #11.3-continued

| | | Vaccine | 2-log anti-E2 ELISA antibody titre in serum 3 week post-boost | | |
|---|---|---|---|---|---|
| Group | Antigen | Adjuvant formulation | GMT | STDEV | antilog |
| | | [40/160/40] injected separately from the antigen | | | |

TABLE #11.4

| | | Vaccine | Stimulation index 3 weeks after the first vaccination | | Stimulation index 3 weeks after the second vaccination | |
|---|---|---|---|---|---|---|
| Group | Antigen | Adjuvant formulation | AMT | STDEV | AMT | STDEV |
| 1 | CSFV-E2 | No adjuvant | 184 | 196 | 325 | 543 |
| 2 | CSFV-E2 | (sulphate)1-(dodecanoyl)7-sucrose/polysorbate 80 [40/40] | 2,257 | 1,389 | 7,601 | 7,186 |
| 3 | CSFV-E2 | squalane/polysorbate 80 [160/40] | 1,298 | 1,324 | 516 | 789 |
| 4 | CSFV-E2 | (sulphate)1-(dodecanoyl)7-sucrose/squalane/polysorbate 80 [40/160/40] | 1,654 | 760 | 37,204 | 28,026 |
| 5 | CSFV-E2 | (sulphate)1-(dodecanoyl)7-sucrose/squalane/polysorbate 80 [40/160/40] injected separately from the antigen | 5,195 | 5,134 | 14,210 | 12,003 |

Example #12

Several sucrose derivatives were synthesized as described in Example #1. Sucrose was contacted with dodecanoylchloride (dodecanoylchloride; Merck), decanoylchloride (Merck), octanoylchloride (Merck) or hexanoylchloride (Merck) and with $SO_3$·pyridine. The quantities of the starting materials used are set forth in Table #12.1

The products obtained were analysed by TLC as described in Example #1.

Formulations of the sucrose derivatives of Table #12.1 with polysorbate 80 (ICI), squalane (Merck) and PBS-thimerosal were prepared as described hereinabove in Example #1.

The effect of these formulations on immune responses against CSFV-E2 was determined in pigs as described hereinabove in Example #1. Results are set forth in Table #12.2.

Antibody titres were measured by ELISA as described hereinabove in Example #3. Results are set forth in Table #12.3.

The cell-mediated response against CSFV was measured by the lymphocyte proliferation assay as described hereinabove in Example #2. Results are set forth in Table #12.4.

TABLE #12.1

| Sucrose derivative | Sucrose (g) | acoylchloride (g) | (type) | $SO_3$·Pyridine (g) | NMP (g) | Pyridine (g) | Molar ratios L/sucrose | S/sucrose |
|---|---|---|---|---|---|---|---|---|
| (sulphate)1-(dodecanoyl)7-sucrose | 17.1 | 76.7 | dodecanoyl-chloride | 8 | 74 | 40 | 7.0 | 1.0 |
| (sulphate)1-(decanoyl)7-sucrose | 17.1 | 66.8 | decanoyl-chloride | 8 | 74 | 40 | 7.0 | 1.0 |
| (sulphate)1-(octanoyl)7-sucrose | 17.1 | 56.9 | octanoyl-chloride | 8 | 74 | 40 | 7.0 | 1.0 |
| (sulphate)1-(hexanoyl)7-sucrose | 17.7 | 47.1 | hexanoyl-chloride | 8 | 74 | 40 | 7.0 | 1.0 |

Molar ratio: L/Sucrose: mole acoylchloride per mole sucrose; S/sucrose: mole $SO_3$·pyridine per mole sucrose.

TABLE #12.2

| Group | Vaccine Antigen | Adjuvant formulation | 2-log CSFV neutralising antibody titre in serum 3 week post-boost | | |
|---|---|---|---|---|---|
| | | | GMT | STDEV | antilog |
| 1 | CSFV-E2 | No adjuvant | 3.7 | 0.3 | 13 |
| 3 | CSFV-E2 | (sulphate)1-(dodecanoyl)7-sucrose/squalane/polysorbate 80 [40/160/40] | 12.0 | 1.8 | 7,424 |
| 4 | CSFV-E2 | (sulphate)1-(decanoyl)7-sucrose/squalane/polysorbate 80 [40/160/40] | 14.1 | 1.6 | 25,088 |
| 5 | CSFV-E2 | (sulphate)1-(octanoyl)7-sucrose/squalane/polysorbate 80 [40/160/40] | 13.4 | 1.9 | 17,152 |
| 6 | CSFV-E2 | (sulphate)1-(hexanoyl)7-sucrose/squalane/polysorbate 80 [40/160/40] | 9.7 | 2.3 | 2,280 |

TABLE #12.3

| Group | Vaccine Antigen | Adjuvant formulation | 2-log anti-E2 ELISA antibody titre in serum 3 week post-boost | | |
|---|---|---|---|---|---|
| | | | GMT | STDEV | antilog |
| 1 | CSFV-E2 | No adjuvant | 2.5 | 0.7 | 6 |
| 2 | CSFV-E2 | (sulphate)1-(dodecanoyl)7-sucrose/squalane/polysorbate 80 [40/160/40] | 9.1 | 1.4 | 555 |
| 3 | CSFV-E2 | (sulphate)1-(decanoyl)7-sucrose/squalane/polysorbate 80 [40/160/40] | 11.0 | 2.0 | 2,062 |
| 4 | CSFV-E2 | (sulphate)1-(octanoyl)7-sucrose/squalane/polysorbate 80 [40/160/40] | 10.1 | 1.2 | 1,113 |
| 5 | CSFV-E2 | (sulphate)1-(hexanoyl)7-sucrose/squalane/polysorbate 80 [40/160/40] | 7.9 | 1.3 | 243 |

TABLE #12.4

| | Vaccine | | Stimulation index 3 weeks after the first vaccination | | Stimulation index 3 weeks after the second vaccination | |
|---|---|---|---|---|---|---|
| Group | Antigen | Adjuvant formulation | AMT | STDEV | AMT | STDEV |
| 1 | CSFV-E2 | No adjuvant | 184 | 196 | 325 | 543 |
| 2 | CSFV-E2 | (sulphate)1-(dodecanoyl)7-sucrose/squalane/polysorbate 80 [40/160/40] | 1,654 | 760 | 37,204 | 28,026 |
| 3 | CSFV-E2 | (sulphate)1-(decanoyl)7-sucrose/squalane/polysorbate 80 [40/160/40] | 8,627 | 7,816 | 52,791 | 24,632 |
| 4 | CSFV-E2 | (sulphate)1-(octanoyl)7-sucrose/squalane/polysorbate 80 [40/160/40] | 2,995 | 1,899 | 33,172 | 27,272 |
| 5 | CSFV-E2 | (sulphate)1-(hexanoyl)7-sucrose/squalane/polysorbate 80 [40/160/40] | 1,310 | 547 | 34,809 | 31,555 |

Example #13

Formulations of sucrose ester L195 (Mitsubishi-Kagaku Foods Corp., Tokyo, Japan), polysorbate 80 (Merck), squalane (Merck), (oleoyl)-8-sucrose of Example #9, dimethyldioctadecylammonium bromide (DDA; Eastman Kodak Company, Rochester, N.Y.), Carbopol 934 PH (BFGoodrich, Cleveland Ohio) were prepared as described in Example #. The quantities of the starting materials used are set forth in Table #13.1

The effect of (several of) these formulations on immune responses against CSFV-E2 was determined in pigs as described hereinabove in Example #1. Results are set forth in Table #13.2.

Antibody titres were measured by ELISA as described hereinabove in Example #3. Results are set forth in Table #13.3.

The cell-mediated response against CSFV was measured by the lymphocyte proliferation assay as described hereinabove in Example #2. Results are set forth in Table #13.4.

TABLE #13.1

| Emulsion | Composition |
| --- | --- |
| squalane/polysorbate 80 [160/40] | 40 g squalane + 10 g polysorbate 80 + 190 g PBS-thimerosal |
| L195/squalane/polysorbate 80 [40/160/40] | 10 g sucrose ester L195 + 40 g squalane + 10 g polysorbate 80 + 190 g PBS-thimerosal |
| L195/(oleoyl)8-sucrose/polysorbate 80 [40/160/40] | 10 g sucrose ester L195 + 40 g (oleoyl)8-sucrose + 10 g polysorbate 80 + 190 g PBS-thimerosal |
| L195/DDA/squalane/polysorbate 80 [40/40/160/40] | 10 g sucrose ester L195 + 10 g DDA + 40 g squalane + 10 g polysorbate 80 + 180 g PBS-thimerosal |
| L195/Carbopol/squalane/polysorbate 80 [40/4/160/40] | 10 g sucrose ester L195 + 1 g Carbopol + 40 g squalane + 10 g polysorbate 80 + 189 g PBS-thimerosal |

TABLE #13.2

| | Vaccine | | 2-log CSFV neutralising antibody titre in serum 3 week post-boost | | |
| --- | --- | --- | --- | --- | --- |
| Group | Antigen | Adjuvant formulation | GMT | STDEV | antilog |
| 1 | CSFV-E2 | No adjuvant | 3.7 | 0.3 | 13 |
| 2 | CSFV-E2 | squalane/polysorbate 80 [160/40] | 5.8 | 1.7 | 89 |
| 3 | CSFV-E2 | L195/squalane/polysorbate 80 [40/160/40] | 13.0 | 2.1 | 18,176 |
| 4 | CSFV-E2 | L195/(oleoyl)8-sucrose/polysorbate 80 [40/160/40] | 8.1 | 0.9 | 312 |
| 5 | CSFV-E2 | L195/DDA/squalane/polysorbate 80 [40/40/160/40] | 11.0 | 1.7 | 3,488 |
| 6 | CSFV-E2 | L195/Carbopol/squalane/polysorbate 80 [40/4/160/40] | 12.8 | 0.6 | 7,424 |

TABLE #13.3

| | Vaccine | | 2-log anti-E2 ELISA antibody titre in serum 3 week post-boost | | |
| --- | --- | --- | --- | --- | --- |
| Group | Antigen | Adjuvant formulation | GMT | STDEV | antilog |
| 1 | CSFV-E2 | No adjuvant | 2.5 | 0.7 | 6 |
| 2 | CSFV-E2 | squalane/polysorbate 80 [160/40] | 3.1 | 2.4 | 9 |
| 3 | CSFV-E2 | L195/squalane/polysorbate 80 [40/160/40] | 9.0 | 1.4 | 495 |
| 4 | CSFV-E2 | L195/(oleoyl)8-sucrose/polysorbate 80 [40/160/40] | 6.4 | 0.6 | 84 |
| 5 | CSFV-E2 | L195/DDA/squalane/polysorbate 80 [40/40/160/40] | 9.3 | 1.3 | 609 |
| 6 | CSFV-E2 | L195/Carbopol/squalane/polysorbate 80 [40/4/160/40] | 9.0 | 0.7 | 510 |

TABLE #13.4

| | Vaccine | | Stimulation index 3 weeks after the first vaccination | | Stimulation index 3 weeks after the second vaccination | |
| --- | --- | --- | --- | --- | --- | --- |
| Group | Antigen | Adjuvant formulation | AMT | STDEV | AMT | STDEV |
| 1 | CSFV-E2 | No adjuvant | 184 | 196 | 325 | 543 |
| 2 | CSFV-E2 | squalane/polysorbate 80 [160/40] | 1,298 | 1,324 | 516 | 789 |
| 3 | CSFV-E2 | L195/squalane/polysorbate 80 [40/160/40] | 3,363 | 2,077 | 15,626 | 9,599 |
| 4 | CSFV-E2 | L195/(oleoyl)8-sucrose/polysorbate 80 [40/160/40] | NT | | 1,629 | 1,226 |
| 5 | CSFV-E2 | L195/DDA/squalane/polysorbate 80 [40/40/160/40] | 17,145 | 20,804 | 34,536 | 30,990 |
| 6 | CSFV-E2 | L195/Carbopol/squalane/polysorbate 80 [40/4/160/40] | NT | | 46,345 | 31,655 |

NT = not tested

Example #14

A mannose derivative was synthesized as described in Example #1. The quantities of the starting materials used are set forth in Table #4.1

TABLE #14.1

| Sucrose derivative | mannose (g) | acoylchloride (g) (type) | SO$_3$•Pyridine (g) | NMP (g) | Pyridine (g) | Molar ratios L/mannose | S/mannose |
| --- | --- | --- | --- | --- | --- | --- | --- |
| (sulphate)1-(dodecanoyl)4-mannose | 9.0 | 43.8 dodecanoyl-chloride | 8.0 | 74 | 40 | 4.0 | 1.0 |

Molar ratio: L/mannose: mole acoylchloride per mole mannose; S/mannose: mole SO$_3$•pyridine per mole mannose.

The products obtained were analysed by TLC as described in Example #1.

A formulation of the 10 g mannose derivative of Table #14.1 with 10 g polysorbate 80 (ICI), 40 g squalane (Merck) and 190 g PBS-thimerosal was prepared as described above in Example #1.

The effect of (several of) these formulations on immune responses against CSFV-E2 was determined in pigs as described hereinabove in Example #1. Results are set forth in Table #14.2.

Antibody titres were measured by ELISA as described hereinabove in Example #3. Results are set forth in Table #14.3.

The cell-mediated response against CSFV was measured by the lymphocyte proliferation assay as described hereinabove in Example #2. Results are set forth in Table #14.4.

TABLE #14.2

| | Vaccine | | 2-log CSFV neutralising antibody titre in serum 3 week post-boost | | |
|---|---|---|---|---|---|
| Group | Antigen | Adjuvant formulation | GMT | STDEV | antilog |
| 1 | CSFV-E2 | No adjuvant | 3.7 | 0.3 | 13 |
| 3 | CSFV-E2 | (sulphate)1-(dodecanoyl)4-mannose/squalane/polysorbate 80 [40/160/40] | 11.8 | 1.1 | 4,352 |

TABLE #14.3

| | Vaccine | | 2-log anti-E2 ELISA antibody titre in serum 3 week post-boost | | |
|---|---|---|---|---|---|
| Group | Antigen | Adjuvant formulation | GMT | STDEV | antilog |
| 1 | CSFV-E2 | No adjuvant | 2.5 | 0.7 | 6 |
| 2 | CSFV-E2 | (sulphate)1-(dodecanoyl)4-mannose/squalane/polysorbate 80 [40/160/40] | 8.7 | 0.9 | 411 |

TABLE #14.4

| | Vaccine | | Stimulation index 3 weeks after the first vaccination | | Stimulation index 3 weeks after the second vaccination | |
|---|---|---|---|---|---|---|
| Group | Antigen | Adjuvant formulation | AMT | STDEV | AMT | STDEV |
| 1 | CSFV-E2 | No adjuvant | 184 | 196 | 325 | 543 |
| 2 | CSFV-E2 | (sulphate)1-(dodecanoyl)4-mannose/squalane/polysorbate 80 [40/160/40] | 4,292 | 2,503 | 30,146 | 26,889 |

Example #15

A (sulphate)1-(dodecanoyl)-2-glycerol was synthesized as described in Example #1. 4.6 g anhydrous glycerol (Merck) was dissolved in anhydrous N-methylpyrrolidinone (Merck) and anhydrous pyridine (Merck). 21.9 g dodecanoylchloride (Merck) was added and the reaction mixture was incubated for 6 h at 60° C. 8.0 g $SO_3$.pyridine (Merck) was added and the reaction mixture was incubated for 18 h at room temperature. The reaction mixture was kept at 4° C. for 24 h, which caused the formation of two phases. The upper phases were collected and N-methylpyrrolidinone and pyridine were removed by evaporation at increased temperature (<60° C.), reduced pressure (<10 mbar) and condensation at 4° C., until the weight loss of the residue was less than 0.1 g per 30 min.

The (sulphate)1-(dodecanoyl)-2-glycerol obtained was analysed by TLC as described in Example #1.

A formulation of the 10 g glycerol derivative, 10 g polysorbate 80 (ICI), 40 g squalane (Merck) and 190 g PBS-thimerosal was prepared as described above in Example #1.

The effect of (several of) these formulations on immune responses against CSFV-E2 was determined in pigs as described hereinabove in Example #1. Results are set forth in Table #15.1.

Antibody titres were measured by ELISA as described hereinabove in Example #3. Results are set forth in Table #15.2.

The cell-mediated response against CSFV was measured by the lymphocyte proliferation assay as described hereinabove in Example #2. Results are set forth in Table #15.3.

TABLE #15.1

| | Vaccine | | 2-log CSFV-neutralising antibody titre in serum 3 week post-boost | | |
|---|---|---|---|---|---|
| Group | Antigen | Adjuvant formulation | GMT | STDEV | antilog |
| 1 | CSFV-E2 | No adjuvant | 3.7 | 0.3 | 13 |
| 3 | CSFV-E2 | (sulphate)1-(dodecanoyl)2-glycerol/squalane/polysorbate 80 [40/160/40] | 4.8 | 2.0 | 51 |

TABLE #15.2

| | Vaccine | | 2-log anti-E2 ELSIA antibody titre in serum 3 week post-boost | | |
|---|---|---|---|---|---|
| Group | Antigen | Adjuvant formulation | GMT | STDEV | antilog |
| 1 | CSFV-E2 | No adjuvant | 2.5 | 0.7 | 6 |
| 2 | CSFV-E2 | (sulphate)1-(dodecanoyl)2-glycerol/squalane/polysorbate 80 [40/160/40] | 3.9 | 2.0 | 15 |

TABLE #15.3

| | Vaccine | | Stimulation index 3 weeks after the first vaccination | | Stimulation index 3 weeks after the second vaccination | |
|---|---|---|---|---|---|---|
| Group | Antigen | Adjuvant formulation | AMT | STDEV | AMT | STDEV |
| 1 | CSFV-E2 | No adjuvant | 184 | 196 | 325 | 543 |

TABLE #15.3-continued

| | | | Vaccine | Stimulation index 3 weeks after the first vaccination | | Stimulation index 3 weeks after the second vaccination | |
|---|---|---|---|---|---|---|---|
| Group | Antigen | Adjuvant formulation | | AMT | STDEV | AMT | STDEV |
| 2 | CSFV-E2 | (sulphate)1-(dodecanoyl)2-glycerol/squalane-in-water | | NT | | 2,842 | 853 |

NT = not tested

Example #16

A formulation of 1.3 g sucrose ester L195 (Mitsubishi-Kagaku Foods Corp., Tokyo, Japan), 1.3 g polysorbate 80 (Merck), 10.8 g squalene (Merck) 237.7 g PBS-thimerosal was prepared as described in Example #1. A formulation of 1.3 g (sulphate)1-(dodecanoyl)-7-sucrose of Example #12, 1.3 g polysorbate 80 (Merck), 10.8 g squalene (Merck) and 238.1 g PBS-thimerosal was prepared as described in Example #1.

The effect of several of these formulations on ELISA antibody response in serum against inactivated human influenza virus strains A/Panama, A/New Calcdonia and B/Yamanashi was determined in pigs. For this purpose, One dose (0.5 ml) commercially available influenza virus vaccine INFLUVAC™ of Solvay Pharmaceuticals (Weesp, The Netherlands) was mixed with 1 ml of either adjuvant formulation and groups of five pigs were immunised. Three weeks after the first immunisation, antibody responses were measured by ELISA as described in Example #3. The induction of immunological memory was determined by measuring the antibody response after a second immunisation with INFLUVAC™ of Solvay Pharmaceuticals without adjuvant. Results of antibody titres against A/Panama, A/New Caledonia and B/Yamanashi after the first immunisation are set forth in Table #16.1, #16.2 and 16.3, respectively. Results of antibody titres against A/Panama, A/New Caledonia and B/Yamanashi one week after the second immunisation without adjuvant are set forth in Table #16.4, #16.5 and #16.6, respectively. Results of antibody titres against A/Panama, A/New Calcdonia and B/Yamanashi three weeks after the second immunisation without adjuvant are set forth in Table #16.7, #16.8 and #16.9, respectively.

TABLE #16.1

| | Vaccine | | 2-log anti-A/Panama ELISA antibody titre in serum 3 week after the first immunisation | | |
|---|---|---|---|---|---|
| Group | Antigen | Adjuvant formulation | GMT | STDEV | antilog |
| 1 | INFLUVAC | No adjuvant | 4.4 | 0.8 | 22 |
| 2 | INFLUVAC | L195/squalene/polysorbate 80 [5/43/5] | 8.3 | 0.8 | 322 |
| 3 | INFLUVAC | (sulphate)1-(dodecanoyl)7-sucrose/squalene/polysorbate 80 [5/43/5] | 7.9 | 0.8 | 241 |

TABLE #16.2

| | Vaccine | | 2-log anti-A/New Caledonia ELISA antibody titre in serum 3 week after the first immunisation | | |
|---|---|---|---|---|---|
| Group | Antigen | Adjuvant formulation | GMT | STDEV | antilog |
| 1 | INFLUVAC | No adjuvant | 4.3 | 0.8 | 19 |
| 2 | INFLUVAC | L195/squalene/polysorbate 80 [5/43/5] | 8.0 | 0.5 | 259 |
| 3 | INFLUVAC | (sulphate)1-(dodecanoyl)7-sucrose/squalene/polysorbate 80 [5/43/5] | 8.0 | 1.0 | 247 |

TABLE #16.3

| | Vaccine | | 2-log anti-B/Yamanashi ELISA antibody titre in serum 3 week after the first immunisation | | |
|---|---|---|---|---|---|
| Group | Antigen | Adjuvant formulation | GMT | STDEV | antilog |
| 1 | INFLUVAC | No adjuvant | 4.9 | 0.9 | 29 |
| 2 | INFLUVAC | L195/squalene/polysorbate 80 [5/43/5] | 9.0 | 0.5 | 503 |
| 3 | INFLUVAC | (sulphate)1-(dodecanoyl)7-sucrose/squalene/polysorbate 80 [5/43/5] | 8.7 | 1.0 | 411 |

TABLE #16.4

| | Vaccine | | 2-log anti-A/Panama ELISA antibody titre in serum 3 week after the second immunisation | | |
|---|---|---|---|---|---|
| Group | Antigen | Adjuvant formulation | GMT | STDEV | antilog |
| 1 | INFLUVAC | No adjuvant | 5.8 | 1.4 | 56 |
| 2 | INFLUVAC | L195/squalene/polysorbate 80 [5/43/5] | 10.6 | 1.6 | 1,513 |
| 3 | INFLUVAC | (sulphate)1-(dodecanoyl)7-sucrose/squalene/polysorbate 80 [5/43/5] | 10.1 | 1.1 | 1,061 |

TABLE #16.5

| | | | 2-log anti-A/New Caledonia ELISA antibody titre in serum 3 week after the second immunisation | | |
|---|---|---|---|---|---|
| Group | Antigen | Vaccine Adjuvant formulation | GMT | STDEV | antilog |
| 1 | INFLUVAC | No adjuvant | 5.8 | 1.3 | 57 |
| 2 | INFLUVAC | L195/squalene/polysorbate 80 [5/43/5] | 10.9 | 1.0 | 1,898 |
| 3 | INFLUVAC | (sulphate)1-(dodecanoyl)7-sucrose/squalene/polysorbate 80 [5/43/5] | 10.4 | 1.2 | 1,313 |

TABLE #16.6

| | | | 2-log anti-B/Yamanashi ELISA antibody titre in serum 3 week after the second immunisation | | |
|---|---|---|---|---|---|
| Group | Antigen | Vaccine Adjuvant formulation | GMT | STDEV | antilog |
| 1 | INFLUVAC | No adjuvant | 6.3 | 1.3 | 81 |
| 2 | INFLUVAC | L195/squalene/polysorbate 80 [5/43/5] | 11.1 | 1.0 | 2,260 |
| 3 | INFLUVAC | (sulphate)1-(dodecanoyl)7-sucrose/squalene/polysorbate 80 [5/43/5] | 11.9 | 1 | 1,868 |

TABLE #16.7

| | | | 2-log anti-A/Panama ELISA antibody titre in serum 3 week after the second immunisation | | |
|---|---|---|---|---|---|
| Group | Antigen | Vaccine Adjuvant formulation | GMT | STDEV | antilog |
| 1 | INFLUVAC | No adjuvant | 5.8 | 1.8 | 54 |
| 2 | INFLUVAC | L195/squalene/polysorbate 80 [5/43/5] | 9.2 | 1.6 | 573 |
| 3 | INFLUVAC | (sulphate)1-(dodecanoyl)7-sucrose/squalene/polysorbate 80 [5/43/5] | 8.6 | 1.0 | 383 |

TABLE #16.8

| | | | 2-log anti-A/New Caledonia ELISA antibody titre in serum 3 week after the second immunisation | | |
|---|---|---|---|---|---|
| Group | Antigen | Vaccine Adjuvant formulation | GMT | STDEV | antilog |
| 1 | INFLUVAC | No adjuvant | 6.1 | 2.0 | 70 |
| 2 | INFLUVAC | L195/squalene/polysorbate 80 [5/43/5] | 9.0 | 0.9 | 496 |
| 3 | INFLUVAC | (sulphate)1-(dodecanoyl)7-sucrose/squalene/polysorbate 80 [5/43/5] | 8.7 | 1.2 | 419 |

TABLE #16.9

| | | | 2-log anti-B/Yamanashi ELISA antibody titre in serum 3 week after the second immunisation | | |
|---|---|---|---|---|---|
| Group | Antigen | Vaccine Adjuvant formulation | GMT | STDEV | antilog |
| 1 | INFLUVAC | No adjuvant | 6.1 | 1.6 | 68 |
| 2 | INFLUVAC | L195/squalene/polysorbate 80 [5/43/5] | 9.3 | 1.1 | 613 |
| 3 | INFLUVAC | (sulphate)1-(dodecanoyl)7-sucrose/squalene/polysorbate 80 [5/43/5] | 8.9 | 0.9 | 472 |

Example #17

A (sulphate)1-(dodecanoyl)-7-sucrose ester was synthesized by contacting 205.2 g sucrose with 918 g dodecanoyl-chloride and 98 g $SO_3$.pyridine as described in Example #1. The sucrose ester was extracted with n-hexane as described hereinabove in Example #2.

A (sulphate)-4-(dodecanoyl)-4-sucrose ester was synthesized by contacting 23.9 g sucrose with 67.5 g dodecanoyl-chloride and 45.6 g $SO_3$.pyridine as described in Example #1.

The products obtained were analysed by TLC as described in Example #1.

Adjuvant formulations of (sulphate)1-(dodecanoyl)-7-sucrose were prepared with squalane (Merck), squalene (Merck), hexadecane (Acros, Geel, Belgium), triolein (Sigma, St. Louis, Mich.) Markol 52 (Esso), perfluorooctyl-bromide (Acros), or silicon oil (Acros) as oil, Polysorbate 80 (Merck), Polysorbate 20 (Baker), L1695 (Mitsubishi-Kagaku), Triton X-100 (Sigma), Saponin (Fluka, Zwijndrecht, The Netherlands) or (sulphate)-4-(dodecanoyl)-4-sucrose as emulsifiers and PBS-thimerosal or WFI (water-for-injections of ID-Lelystad, Lelystad, The Netherlands) as aqueous phase at quantities indicated hereinbelow in Table #17.1.

These formulations were emulsified as described above in Example #1.

TABLE #17.1

| | Composition | | | |
|---|---|---|---|---|
| Emulsion | Sucrose ester | Oil | Emulsifier/ stabilizer | Aqueous phase |
| (sulphate)1-(dodecanoyl)7-sucrose/squalane/polysorbate 80 [40/160/40] | 10 g (sulphate)1-(dodecanoyl)7-sucrose | 40 g squalane | 10 g Polysorbate 80 | 190 g PBS-thimerosal |
| (sulphate)1-(dodecanoyl)7-sucrose/squalene/polysorbate 80 [40/160/40] | 10 g (sulphate)1-(dodecanoyl)7-sucrose | 40 g squalene | 10 g Polysorbate 80 | 190 g PBS-thimerosal |
| (sulphate)1-(dodecanoyl)7-sucrose/hexadecane/polysorbate 80 [40/160/40] | 10 g (sulphate)1-(dodecanoyl)7-sucrose | 40 g hexadecane | 10 g Polysorbate 80 | 190 g PBS-thimerosal |
| (sulphate)1-(dodecanoyl)7-sucrose/hexadecane/polysorbate 80 [40/160/40] | 10 g (sulphate)1-(dodecanoyl)7-sucrose | 40 g triolein | 10 g Polysorbate 80 | 190 g PBS-thimerosal |
| (sulphate)1-(dodecanoyl)7-sucrose/Markol/polysorbate 80 [40/160/40] | 10 g (sulphate)1-(dodecanoyl)7-sucrose | 40 g Markol 52 | 10 g Polysorbate 80 | 190 g PBS-thimerosal |
| (sulphate)1-(dodecanoyl)7-sucrose/silicon oil/polysorbate 80 [40/160/40] | 10 g (sulphate)1-(dodecanoyl)7-sucrose | 40 g silicon oil | 10 g Polysorbate 80 | 190 g PBS-thimerosal |
| (sulphate)1-(dodecanoyl)7-sucrose/fluorbron/polysorbate 80 [40/160/40] | 5 g (sulphate)1-(dodecanoyl)7-sucrose | 20 g perfluoro-octylbromide | 5 g Polysorbate 80 | 95 g PBS-thimerosal |
| (sulphate)1-(dodecanoyl)7-sucrose/squalene/L1695 [40/160/40] | 10 g (sulphate)1-(dodecanoyl)7-sucrose | 40 g squalene | 10 g L1695 | 190 g PBS-thimerosal |
| (sulphate)1-(dodecanoyl)7-sucrose/squalene/(sulphate)4-(dodecanoyl)4-sucrose [40/160/40] | 10 g (sulphate)1-(dodecanoyl)7-sucrose | 40 g squalene | 10 g (sulphate)4-(dodecanoyl)4-sucrose | 190 g PBS-thimerosal |
| (sulphate)1-(dodecanoyl)7-sucrose/squalene/polysorbate 20 [40/160/40] | 10 g (sulphate)1-(dodecanoyl)7-sucrose | 40 g squalene | 10 g Polysorbate 20 | 190 g PBS-thimerosal |
| (sulphate)1-(dodecanoyl)7-sucrose/squalene/Triton X-100 [40/160/40] | 10 g (sulphate)1-(dodecanoyl)7-sucrose | 40 g squalene | 10 g Triton X-100 | 190 g PBS-thimerosal |
| (sulphate)1-(dodecanoyl)7-sucrose/squalene/saponin [40/160/40] | 10 g (sulphate)1-(dodecanoyl)7-sucrose | 40 g squalene | 10 g saponin | 190 g PBS-thimerosal |
| (sulphate)1-(dodecanoyl)7-sucrose/squalane/polysorbate 80 (80/320/80]] | 20 g (sulphate)1-(dodecanoyl)7-sucrose | 80 g squalane | 20 g Polysorbate 80 | 130 g PBS-thimerosal |
| (sulphate)1-(dodecanoyl)7-sucrose/squalane/polysorbate 80 [120/480/120] | 30 g (sulphate)1-(dodecanoyl)7-sucrose | 120 g squalane | 30 g Polysorbate 80 | 70 g PBS-thimerosal |
| (sulphate)1-(dodecanoyl)7-sucrose/squalane/polysorbate 80 [160/640/160] | 40 g (sulphate)1-(dodecanoyl)7-sucrose | 160 g squalane | 40 g Polysorbate 80 | 10 g WFI |

The effect of (several of) these formulations on immune responses against CSFV-E2 was determined in pigs as described hereinabove in Example #1. Group 1 and 2 consisted of 5 pigs per group and Groups 3 to 10 consisted of 4 pigs per group. Vaccines were prepared by simple mixing one volume of adjuvant formulation with one volume of antigen formulation. The antibody titres in serum against CSFV were measured by ELISA as described hereinabove in Example #3. Results are set forth in Table #17.2.

The cell-mediated response against CSFV was measured by the lymphocyte proliferation assay as described hereinabove in Example #2. Results are set forth in Table #17.3.

TABLE #17.2

| | | Vaccine | 2-log anti-E2 ELSIA antibody titre in serum | | |
|---|---|---|---|---|---|
| | | Adjuvant | 1 week post-boost | | |
| Group | Antigen | formulation | GMT | STDEV | antilog |
| 1 | CSFV-E2 | No adjuvant | 6.4 | 2.0 | 86 |
| 2 | CSFV-E2 | (sulphate)1-(dodecanoyl)7-sucrose/squalane/ | 15.9 | 0.9 | 60,720 |

TABLE #17.2-continued

| Group | Vaccine Antigen | Adjuvant formulation | 2-log anti-E2 ELSIA antibody titre in serum 1 week post-boost | | |
|---|---|---|---|---|---|
| | | | GMT | STDEV | antilog |
| 3 | CSFV-E2 | (sulphate)1-(dodecanoyl)7-sucrose/squalane/polysorbate 80 [40/160/40] | 16.2 | 0.8 | 72,977 |
| 4 | CSFV-E2 | (sulphate)1-(dodecanoyl)7-sucrose/squalane/polysorbate 80 [80/320/80] | 14.2 | 0.8 | 18,940 |
| 5 | CSFV-E2 | (sulphate)1-(dodecanoyl)7-sucrose/squalene/polysorbate 80 [40/160/40] | 14.7 | 1.1 | 26,489 |
| 6 | CSFV-E2 | (sulphate)1-(dodecanoyl)7-sucrose/squalene/L1695 [40/160/40] | 12.3 | 1.1 | 4,897 |
| 7 | CSFV-E2 | (sulphate)1-(dodecanoyl)7-sucrose/squalane/(sulphate)4-(dodecanoyl)4-sucrose [40/160/40] | 13.4 | 1.6 | 10,925 |
| 8 | CSFV-E2 | (sulphate)1-(dodecanoyl)7-sucrose/squalane/(sulphate)4-(dodecanoyl)4-sucrose [80/320/80] | 15.6 | 1.2 | 49,123 |
| 9 | CSPV-E2 | (sulphate)1-(dodecanoyl)7-sucrose/Markol/polysorbate 80 [40/160/40] | 13.5 | 1.5 | 11,281 |
| 10 | CSFV-E2 | (sulphate)1-(dodecanoyl)7-sucrose/silicon oil/polysorbate 80 [40/160/40] | 13.4 | 1.2 | 11,059 |
| | CSFV-E2 | (sulphate)1-(dodecanoyl)7-sucrose/perfluorooctylbromide/polysorbate 80 [40/160/40] | | | |

TABLE #17.3

| Group | Vaccine Antigen | Adjuvant formulation | Stimulation index 1 week post-boost | |
|---|---|---|---|---|
| | | | AMT | STDEV |
| 1 | CSFV-E2 | No adjuvant | 176 | 95 |
| 2 | CSFV-E2 | (sulphate)1-(dodecanoyl)7-sucrose/squalane/polysorbate 80 [40/160/40] | 11,719 | 13,401 |
| 3 | CSFV-E2 | (sulphate)1-(dodecanoyl)7-sucrose/squalane/polysorbate 80 [80/320/80] | 7,112 | 3,247 |
| 4 | CSFV-E2 | (sulphate)1-(dodecanoyl)7-sucrose/squalene/polysorbate 80 [40/160/40] | 5,557 | 3,933 |
| 5 | CSFV-E2 | (sulphate)1-(dodecanoyl)7-sucrose/squalene/L1695 [40/160/40] | 4,092 | 2,718 |
| 6 | CSFV-E2 | (sulphate)1-(dodecanoyl)7-sucrose/squalene/(sulphate)4-(dodecanoyl)4-sucrose [40/160/40] | 3,072 | 3,832 |
| 7 | CSFV-E2 | (sulphate)1-(dodecanoyl)7-sucrose/squalane/(sulphate)4-(dodecanoyl)4-sucrose [80/320/80] | 8,351 | 3,885 |
| 8 | CSFV-E2 | (sulphate)1-(dodecanoyl)7-sucrose/Markol/polysorbate 80 [40/160/40] | 7,078 | 1,428 |
| 9 | CSFV-E2 | (sulphate)1-(dodecanoyl)7-sucrose/silicon oil/polysorbate 80 [40/160/40] | 25,760 | 25,126 |
| 10 | CSFV-E2 | (sulphate)1-(dodecanoyl)7-sucrose/perfluorooctylbromide/polysorbate 80 [40/160/40] | 19,209 | 35,430 |

NT = not tested

Example #18

A (sulphate)1-(decanoyl)-7-sucrose ester was synthesized by contacting 23.9 g sucrose with 94 g decanoylchloride and 11.1 g SO3.pyridine as described in Example #1. The sucrose ester was extracted with n-hexane as described hereinabove in Example #2.

A (sulphate)-4-(decanoyl)-4-sucrose ester was synthesized by contacting 24 g sucrose with 54.4 g decanoylchloride and 45 g $SO_3$.pyridine as described in Example #1. The products obtained were analysed by TLC as described in Example #1 and the results are set forth in FIG. 18.

Several adjuvant formulations of these sucrose esters were prepared with squalane or squalene as oil, Polysorbate 80, L1695 (Mitsubishi-Kagaku) or (sulphate)-4-(decanoyl)-4-sucrose as emulsifiers and/or stabilizers and PBS-thimerosal at quantities indicated in Table #18.1. These formulations were emulsified as described above in Example #1.

TABLE #18.1

| | Composition | | | |
|---|---|---|---|---|
| Emulsion | Sucrose ester | Oil | Emulsifier/stabilizer | Aqueous phase |
| (sulphate)1-(decanoyl)7-sucrose/squalane/poilysorbate 80 [40/160/40] | 10 g (sulphate)1-(decanoyl)7-sucrose | 40 g squalane | 10 g Polysorbate 80 | 190 g PBS-thimerosal |
| (sulphate)1-(decanoyl)7-sucrose/squalane/L1695 [40/160/40] | 10 g (sulphate)1-(decanoyl)7-sucrose | 40 g squalane | 10 g L1695 | 190 g PBS-thimerosal |
| (sulphate)1-(decanoyl)7-sucrose/squalane/(sulphate)4-(decanoyl)4-sucrose [40/160/40] | 10 g (sulphate)1-(decanoyl)7-sucrose | 40 g squalane | 10 g (sulphate)4-(decanoyl)4-sucrose | 190 g PBS-thimerosal |

TABLE #18.1-continued

| Emulsion | Composition | | | |
|---|---|---|---|---|
| | Sucrose ester | Oil | Emulsifier/-stabilizer | Aqueous phase |
| (sulphate)1-(decanoyl)7-sucrose/squalene/polysorbate 80 [40/160/40] | 10 g (sulphate)1-(decanoyl)7-sucrose | 40 g squalene | 10 g Polysorbate 80 | 190 g PBS-thimerosal |
| (sulphate)1-(decanoyl)7-sucrose/squalene/L1695 [40/160/40] | 10 g (sulphate)1-(decanoyl)7-sucrose | 40 g squalene | 10 g L1695 | 190 g PBS-thimerosal |
| (sulphate)1-(decanoyl)7-sucrose/squalene/(sulphate)4-(decanoyl)4-sucrose [40/160/40] | 10 g (sulphate)1-(decanoyl)7-sucrose | 40 g squalene | 10 g (sulphate)4-(decanoyl)4-sucrose | 190 g PBS-thimerosal |

Legend to Table #18.1: Squalane (Merck), squalene (Merck), Polysorbate 80 (Merck), Polysorbate 20 (Baker), L1695 (Mitsubishi-Kagaku Foods Corp., Tokyo, Japan), WFI is water-for-injections (ID-Lelystad, Lelystad, The Netherlands).

The effect of (several of) these formulations on immune responses against CSFV-E2 was determined in pigs as described hereinabove in Example #1. Group 1 consisted of 5 pigs per group and Groups 2 and 3 consisted of 4 pigs per group. Vaccines were prepared by simple mixing one volume of adjuvant formulation with one volume of antigen formulation. The antibody titres in serum against CSFV were measured by ELISA as described hereinabove in Example #3. Results are set forth in Table #18.2.

The cell-mediated response against CSFV was measured by the lymphocyte proliferation assay as described hereinabove in Example #2. Results are set forth in Table #18.3.

TABLE #18.2

| | Vaccine | | 2-log anti-E2 ELSIA antibody titre in serum 1 week post-boost | | |
|---|---|---|---|---|---|
| Group | Antigen | Adjuvant formulation | GMT | STDEV | antilog |
| 1 | CSFV-E2 | No adjuvant | 6.4 | 2.0 | 86 |
| 2 | CSFV-E2 | (sulphate)1-(decanoyl)7-sucrose/squalene/polysorbate 80 [40/160/40] | 13.6 | 1.0 | 12,024 |
| 3 | CSFV-E2 | (sulphate)1-(decanoyl)7-sucrose/squalene/L1695 [40/160/40] | 14.6 | 0.5 | 25,063 |

TABLE #18.3

| | Vaccine | | Stimulation index 1 week post-boost | |
|---|---|---|---|---|
| Group | Antigen | Adjuvant formulation | AMT | STDEV |
| 1 | CSFV-E2 | No adjuvant | 176 | 95 |
| 2 | CSFV-E2 | (sulphate)1-(decanoyl)7-sucrose/squalene/polysorbate 80 [40/160/40] | 2,609 | 866 |
| 3 | CSFV-E2 | (sulphate)1-(decanoyl)7-sucrose/squalene/L1695 [40/160/40] | 3,353 | 2,092 |

NT = not tested

Example #19

Formulations of L195 (Mitsubishi), squalene (Merck), L1695 (Mitsubishi), and PBS-thimerosal or WFI were prepared at quantities indicated in Table #19.1. The formulations were emulsified as described above in Example #1.

TABLE #19.1

| Emulsion | Composition | | | |
|---|---|---|---|---|
| | Sucrose ester | Oil | Emulsifier-/stabilizer | Aqueous phase |
| L195/squalene/L1695 [40/160/40] | 10 g L195 | 40 g squalene | 10 g L1695 | 190 g PBS-thimerosal |
| L195/squalene/L1695 [80/320/80] | 20 g L195 | 80 g squalene | 20 g L1695 | 130 g PBS-thimerosal |
| L195/squalene/L1695 [120/480/120] | 30 g L195 | 120 g squalene | 30 g L1695 | 70 g PBS-thimerosal |
| L195/squalene/L1695 [160/640/160] | 40 g L195 | 160 g squalene | 40 g L1695 | 10 g WFI |

Squalene (Merck), L195 and L1695 (Mitsubishi-Kagaku), PBS-thimerosal and WFI (ID-Lelystad, Lelystad, The Netherlands).

The effect of two of these formulations on immune responses against CSFV-E2 was determined in pigs as described hereinabove in Example 1. Group 1 consisted of 5 pigs per group and Groups 2 and 3 consisted of 4 pigs per group. Vaccines were prepared by simple mixing one volume of adjuvant formulation with one volume of antigen formulation. The antibody titres in serum against CSFV were measured by ELISA as described hereinabove in Example #3. Results are set forth in Table #19.2.

The cell-mediated response against CSFV was measured by the lymphocyte proliferation assay as described hereinabove in Example #2. Results are set forth in Table #19.3.

TABLE #19.2

| | Vaccine | | 2-log anti-E2 ELSIA antibody titre in serum 1 week post-boost | | |
|---|---|---|---|---|---|
| Group | Antigen | Adjuvant formulation | GMT | STDEV | antilog |
| 1 | CSFV-E2 | No adjuvant | 6.4 | 2.0 | 86 |
| 2 | CSFV-E2 | L195/squalene/L1695 [40/160/40] | 13.0 | 1.5 | 8,212 |
| 3 | CSFV-E2 | L195/squalene/L1695 [80/320/80] | 13.0 | 1.5 | 7,887 |

TABLE #19.3

| | Vaccine | | Stimulation index 1 week post-boost | |
|---|---|---|---|---|
| Group | Antigen | Adjuvant formulation | AMT | STDEV |
| 1 | CSFV-E2 | No adjuvant | 176 | 95 |
| 2 | CSFV-E2 | L195/squalene/L1695 [40/160/40] | 2,949 | 2,418 |
| 3 | CSFV-E2 | L195/squalene/L1695 [80/320/80] | 7,338 | 4,515 |

NT = not tested

Example #20

A (decanoyl)-7-sucrose ester was synthesized as described in Example #1. 23.9 g finely-powdered, sucrose (Merck) was contacted with 94 g decanoylchloride (Merck). The sucrose ester was extracted with n-hexane as described hereinabove in Example #2.

The products obtained were analysed by TLC as described in Example #1.

Formulations of (decanoyl)-7-sucrose ester, squalene, polysorbate 80 and PBS-thimerosal were prepared at quantities indicated in Table #20.1 and emulsified as described above in Example #1.

TABLE #20.1

| | Composition | | | |
|---|---|---|---|---|
| Emulsion | Sucrose ester | Oil | Emulsifier/ stabilizer | Aqueous phase |
| (decanoyl)7-sucrose/squalene/polysorbate 80 [40/160/40] | 10 g (decanoyl)7-sucrose | 40 g squalene | 10 g Polysorbate 80 | 190 g PBS-thimerosal |
| (decanoyl)7-sucrose/squalene/polysorbate 80 [120/480/120] | 30 g (decanoyl)7-sucrose | 120 g squalene | 30 g Polysorbate 80 | 195 g PBS-thimerosal |

The effect of one of these formulations on immune responses against CSFV-E2 was determined in pigs as described hereinabove in Example #1. Group 1 consisted of 5 pigs per group and Group 2 of 4 pigs per group. The antibody titres in serum against CSFV were measured by ELISA as described hereinabove in Example #3. Results are set forth in Table #20.2.

The cell-mediated response against CSFV was measured by the lymphocyte proliferation assay as described hereinabove in Example #2. Results are set forth in Table #20.3.

TABLE #20.2

| | Vaccine | | 2-log anti-E2 ELSIA antibody titre in serum 1 week post-boost | | |
|---|---|---|---|---|---|
| Group | Antigen | Adjuvant formulation | GMT | STDEV | antilog |
| 1 | CSFV-E2 | No adjuvant | 6.4 | 2.0 | 86 |
| 2 | CSFV-E2 | (decanoyl)7-sucrose/squalene/polysorbate 80 [40/160/40] | 14.1 | 1.4 | 17,604 |

TABLE #20.3

| | Vaccine | | Stimulation index 1 week post-boost | |
|---|---|---|---|---|
| Group | Antigen | Adjuvant formulation | AMT | STDEV |
| 1 | CSFV-E2 | No adjuvant | 176 | 95 |
| 2 | CSFV-E2 | (decanoyl)7-sucrose/squalene/polysorbate 80 [40/160/40] | 3,023 | 2,647 |

NT = not tested

Example #21

Effect of the time interval between the first and second immunisation on the immune response was studied. Groups of pigs were immunised twice with CSFV-E2 plus (sulphate) 1-(dodecanoyl)-7-sucrose/squalene/polysorbate 80 [40/160/40] of Example #17 three (Week 0 and 3) and two (Week 1 and 3) weeks apart. The antibody titres in serum against CSFV were measured by ELISA as described hereinabove in Example #3. Results are set forth in Table #21.1.

The cell-mediated response against CSFV was measured by the lymphocyte proliferation assay as described hereinabove in Example #2. Results are set forth in Table #21.2.

TABLE #21.1

| | Vaccine: CSFV-E2 + (sulphate)1-(dodecanoyl)7-sucrose/squalene/polysorbate 80 [40/160/40] of Example #17 | | 2-log anti-E2 ELSIA antibody titre in serum 1 week post-boost | | |
|---|---|---|---|---|---|
| Group | first immunisation | second immunisation | GMT | STDEV | antilog |
| 1 | Week 0 | Week 3 | 12.3 | 1.1 | 4,897 |
| 2 | Week 1 | Week 3 | 11.2 | 1.1 | 2,327 |

NT = not tested

TABLE #21.1

| | Vaccine | | Stimulation index 1 week post-boost | |
|---|---|---|---|---|
| Group | first immunisation | second immunisation | AMT | STDEV |
| 1 | Week 0 | Week 3 | 3,072 | 3,832 |
| 2 | Week 1 | Week 3 | 3,439 | 1,803 |

Example #22

The adjuvant formulation L195/squalane/polysorbate 80 [40/160/40] prepared as described in Example #13 was mixed with a similar volume of antigen solution containing 3 µg foot-and-mouth disease virus strain O/Taiwan per ml. Groups of 3 pigs were immunised twice with 2 ml vaccine. The anti-O/Taiwan virus neutralising antibody response was measured at different time intervals by the virus neutralising antibody test described by van Maanen and Terpstra (J. Immunol. Meth. 124, pp. 111-119, 1989).

Results are set forth in Table #22.1

TABLE #22.1

| | | | 10log anti-O/Taiwan antibody titre at: | | | | | | | |
|---|---|---|---|---|---|---|---|---|---|---|
| | first | second | Day 10 | | Day 17 | | Day 24 | | Day 28 | |
| Group | immunisation | immunisation | GMT | STDEV | GMT | STDEV | GMT | STDEV | GMT | STDEV |
| 1 | Day 0 | no booster | 0.90 | 0.46 | 0.55 | 0.23 | 0.58 | 0.22 | 0.65 | 0.31 |
| 2 | Day 0 | Day 3 | 1.80 | 0.45 | 2.05 | 0.17 | 1.70 | 0.38 | 1.60 | 0.23 |
| 3 | Day 0 | Day 7 | 1.35 | 0.26 | 1.35 | 0.45 | 1.20 | 0.52 | 1.10 | 0.23 |
| 4 | Day 0 | Day 14 | 0.75 | 0.15 | 0.90 | 0.52 | 2.05 | 0.43 | 2.00 | 0.62 |
| 5 | Day 0 | Day 21 | 1.45 | 0.38 | 1.45 | 0.38 | 1.30 | 0.38 | 2.80 | 0.61 |

Example #23

An adjuvant formulation of 160 g L195, 640 g squalane, 160 g polysorbate 80 and 40 g water-for-injections (L195/squalane/polysorbate 80 [160/640/160]) was emulsified as described in Example #1. One volume of this adjuvant formulation was mixed with one volume of an antigen solution containing 3 µg foot-and-mouth disease virus strain O/Taiwan per ml. Groups of 5 pigs were immunised once with 2 ml vaccine and the antibody response was measured at different time intervals as described in Example #22. The Results are set forth in Table #23.1

TABLE #23.1

| 10log anti-O/Taiwan antibody titre at different time intervals after immunisation | | | | | | | | | |
|---|---|---|---|---|---|---|---|---|---|
| Day 0 | | Day 7 | | Day 14 | | Day 21 | | Day 28 | |
| GMT | STDEV | GMT | STDEV | GMT | STDEV | GMT | STDEV | GMT | STDEV |
| <0.3 | ND | 0.81 | 0.57 | 1.83 | 0.33 | 1.44 | 0.31 | 1.32 | 0.33 |

ND: not determined.

Example #24

The (sulphate)1-(dodecanoyl)-7-sucrose Fraction III/squalane/polysorbate 80 [40/160/40] adjuvant of Example #2 was mixed with a gonadotropin-releasing hormone peptide conjugated to ovalbumin (G6k-GnRH-tandem-dimer-OVA conjugate) prepared as described by Oonk et al. (Vaccine 16, pp 1074-1082, 1998). Ten pigs (Group 1) were immunised twice with 187 µg G6k-GnRH-tandem-dimer-OVA conjugate plus (sulphate)1-(dodecanoyl)7-sucrose Fraction III/squalane/polysorbate 80 [40/160/40] and five pigs (Group 2;

controls) with (sulphate)1-(dodecanoyl)-7-sucrose Fraction III/squalane/polysorbate 80 [40/160/40] without antigen. At different time intervals after the first immunisation at Week 10 and second immunisation at Week 17, antibody titres against GnRH in serum samples diluted 1/2000 were measured by RIA as described by Meloen et al. (Vaccine 12, pp 741-746, 1994) with iodinated GnRH purchased from Amersham Pharmacia Biotech (Buckinghamshire, England). Results are set forth in Table #24.1. The testis weight at Week 24 was determined as described by Meloen et al. (Vaccine 12, pp 741-746, 1994). Results are set forth in Table #24.2.

TABLE #24.1

| | | Anti-GnRH antibody titre at different time intervals after immunisation | | | | | | | | |
|---|---|---|---|---|---|---|---|---|---|---|
| | | Week 10 | | Week 14 | | Week 17 | | Week 20 | | Week 24 | |
| Group | Vaccine | AMT | STDEV | AMT | STDEV | AMT | STDEV | AMT | STDEV | AMT | STDEV |
| 1 | G6k-GnRH-tandem-dimer-OVA conjugate + (sulphate)1-(dodecanoyl)7-sucrose Fraction III/squalane/polysorbate 80 | 0.0 | 0.0 | 5.4 | 5.6 | 3.4 | 3.2 | 67.5 | 31.5 | 51.4 | 29.2 |
| 2 | (sulphate)1-(dodecanoyl)7-sucrose Fraction III/squalane/polysorbate 80 | NT | | NT | | NT | | 0.5 | 0.3 | NT | |

NT = not tested.

TABLE #24.2

| | | Weight of testis (g) Week 24 | |
|---|---|---|---|
| Group | Vaccine | mean | STDEV |
| 1 | G6k-GnRH-tandem-dimer-OVA conjugate + (sulphate)1-(dodecanoyl)7-sucrose Fraction III/squalane/polysorbate 80 | 77.2 | 79.1 |
| 2 | (sulphate)1-(dodecanoyl)7-sucrose Fraction III/squalane/polysorbate 80 | 227.6 | 59.2 |

Example #25

Adjuvant formulations were prepared by mixing (sulphate) 1-(dodecanoyl)-7-sucrose of Example #17, squalane, polysorbate 80 and PBS-thimerosal at quantities set forth in Table #25.1. These mixtures were emulsified as described in Example #1.

TABLE #25.1

| Emulsion | (sulphate)1-(dodecanoyl)7-sucrose (g) | squalane (g) | Polysorbate 80 (g) | PBS-thimerosal (g) |
|---|---|---|---|---|
| (sulphate)1-(dodecanoyl)7-sucrose/polysorbate 80 [40/20] | 10 | 0 | 5 | 235 |
| (sulphate)1-(dodecanoyl)7-sucrose/polysorbate 80 [40/40] | 10 | 0 | 10 | 230 |
| (sulphate)1-(dodecanoyl)7-sucrose/squalane/polysorbate 80 [40/20/20] | 10 | 5 | 5 | 230 |
| (sulphate)1-(dodecanoyl)7-sucrose/squalane/polysorbate 80 [40/20/40] | 10 | 5 | 10 | 225 |
| (sulphate)1-(dodecanoyl)7-sucrose/squalane/polysorbate 80 [40/40/40] | 10 | 10 | 10 | 220 |
| (sulphate)1-(dodecanoyl)7-sucrose/squalane/polysorbate 80 [40/80/40] | 10 | 20 | 10 | 210 |
| (sulphate)1-(dodecanoyl)7-sucrose/squalane/polysorbate 80 [40/160/40] | 10 | 40 | 10 | 190 |
| (sulphate)1-(dodecanoyl)7-sucrose/squalane/polysorbate 80 [40/320/40] | 10 | 80 | 10 | 150 |
| (sulphate)1-(dodecanoyl)7-sucrose/squalane/polysorbate 80 [40/320/80] | 10 | 80 | 20 | 140 |

Example #26

Adjuvant formulations were prepared by mixing 10 g (sulphate)1-(dodecanoyl)7-sucrose of Example #17 10 g polysorbate 80 (Baker) and 230 ml suspension of 3 w/v % aluminum hydroxide (Alhydrogel of Superfos Biosector a/s, Vedbaeck, Denmark).

REFERENCES CITED

1. Hilgers et al. Immunology 60, pp. 141-146, 1986.
2. Hilgers et al. Vaccine 12, pp. 653-660, 1994a.
3. Hilgers et al. Vaccine 12, pp. 661-665, 1994b.
4. Hilgers, et al. Vaccine 17, pp. 219-228, 1999.
5. Mashihi et al. EP-A-0 295 749.
6. Hilgers & Platenburg. EP 0549074 (EP 92/204034).
7. Hilgers, WO 96/20222 or BE95/00120 (SL-CD as novel chemical entity).
8. Hilgers, WO 96/20008 (SL-CD/squalane as adjuvant).
9. Nigam et al. Cancer Res. 38, pp. 3315-3312, 1978.
10. Nigam et al. Br. J. Cancer, 46, pp. 782-793, 1982.
11. U.S. Pat. No. 3,432,489.
12. WO 90/02133.
13. Bonaventura et al. Int. J. Immunopharm. 6, pp. 259-267, 1984.
14. Behling et al. J. Immunol. 117, pp. 847-851, 1976.
15. Azuma EP 1,572,368 (1977).
16. Nishikawa, et al. Chem. Pharm. Bull. 29, pp. 505-513, 1981.
17. Bazin, et al. Carbohydrate Res. 309, pp. 189-205, 1998.

The invention claimed is:

1. A disaccharide derivative, wherein the derivative is of formula:

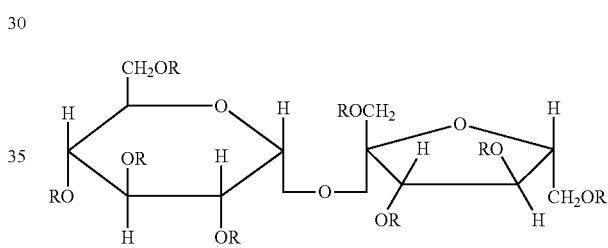

wherein
  (i) at least 3, but not more than N−1, of the groups R are fatty acid ester groups,
  wherein each of the fatty acid ester groups is represented by: a formula of —C(=O)—(CH$_2$)$_x$CH$_3$ groups, wherein x is between 6 and 14, and
  (ii) at least one, but no more than N−3, of the groups R are anionic —SO$_2$—OR$^1$ groups, wherein R$^1$ is a monovalent cation,
wherein N is the number of groups R of the disaccharide derivative and
wherein the combined number of fatty acid esters and anionic —SO$_2$—OR$^1$ groups does not exceed N and the remaining groups R are hydrogen.

2. A disaccharide derivative according to claim 1 wherein said disaccharide derivative has at least 4, but no more than N−1, fatty acid esters groups and no more than N−3, or no more than N−4, —anionic SO$_2$—OR$^1$ groups.

3. A disaccharide derivative according to claim 1 wherein the monovalent cation is independently selected from the group consisting of H$^+$, K$^+$Na$^+$, Li$^+$ and NH$_4^+$.

* * * * *